US007166463B2

(12) United States Patent
Karpen et al.

(10) Patent No.: US 7,166,463 B2
(45) Date of Patent: Jan. 23, 2007

(54) NUCLEIC ACIDS ENCODING MODIFIED OLFACTORY CYCLIC NUCLEOTIDE GATED ION CHANNELS

(75) Inventors: Jeffrey W. Karpen, Portland, OR (US); Thomas C. Rich, Mobile, AL (US); Dermot M. F. Cooper, Cambridge (GB); Jerome Schaack, Denver, CO (US); Kent Fagan, Centennial, CO (US)

(73) Assignee: The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 10/295,573

(22) Filed: Nov. 15, 2002

(65) Prior Publication Data

US 2003/0157571 A1 Aug. 21, 2003

Related U.S. Application Data

(60) Provisional application No. 60/332,494, filed on Nov. 16, 2001.

(51) Int. Cl.
*C12N 5/10* (2006.01)
*C12N 15/12* (2006.01)
*C12N 15/63* (2006.01)
*C12N 1/21* (2006.01)
*C07K 14/435* (2006.01)

(52) U.S. Cl. ................ 435/325; 435/252.3; 435/320.1; 530/350; 536/23.5

(58) Field of Classification Search ............... 435/69.1, 435/70.1, 252.3, 320.1, 325; 536/23.1, 23.5; 530/300, 350
See application file for complete search history.

(56) References Cited

U.S. PATENT DOCUMENTS

| | | | | |
|---|---|---|---|---|
| 4,683,195 A | 7/1987 | Mullis | ........................... | 435/6 |
| 4,683,202 A | 7/1987 | Mullis | ......................... | 435/91 |
| 4,965,188 A | 10/1990 | Mullis | ........................... | 435/6 |
| 5,312,928 A | 5/1994 | Goldin | ....................... | 548/495 |
| 6,183,974 B1 | 2/2001 | Bringhurst | ................. | 435/7.21 |
| 2003/0100059 A1* | 5/2003 | Yao et al. | ................. | 435/69.1 |

FOREIGN PATENT DOCUMENTS

| | | |
|---|---|---|
| CA | 2255548 | 6/2000 |
| WO | WO 98/58074 | 12/1998 |
| WO | WO 99/25384 | 5/1999 |
| WO | WO 99/35255 | 7/1999 |
| WO | WO 00/71565 | 11/2000 |

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details". Nature Biotech 15: 1222-1223, 1997.*

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Wang et al. Rapid analysis of gene expression (RAGE) facilitates universal expression profiling. Nucleic Acids Res 27(23): 4609-4618, 1999.*

Phillips, A., The challenge of gene therapy and DNA delivery. J Pharm Pharmacology 53: 1169-1174, 2001.*

Kaufman et al. Blood 94: 3178-3184, 1999.*

Bradley et al. Nomenclature for ion channel subunits. Science 294(5549): 2095-2096, 2001.*

Broillet et al. Cyclic nucleotide-gated channels. Ann N Y Acad Sci 868: 730-740, 1999.*

Gavazzo et al. A point mutation in the pore region alters gating, Ca(2+) blockage, and permeation of olfactory cyclic nucleotide-gated channels. J Gen Physiol 116 : 311-325, 2000.*

Grunwald et al. Identification of a domain on the beta-subunit of the rod cGMP-gated cation channel that mediates inhibition by calcium-calmodulin. J Biol Chem 273(15) : 9148-9157, 1998.*

Hofmann et al. International Union of Pharmacology, XLII. Compendium of voltage-gated ion channels: cyclic nucleotide-modulated channels. Pharmacol Rev 55(4): 587-589, 2003.*

Kaupp et al. Cyclic Nucleotide-gated ion channels. Physiol Rev 82 : 769-824, 2002.*

Picco et al. Co-expression of wild-type and mutant olfactory cyclic nucleotide-gated channels: restoration of the native sensitivity to Ca(2+) and Mg(2+) blockage. Neuroreport 12(11) : 2363-2367, 2001.*

Trudeau et al. Calcium/calmodulin of olfactory and rod cyclic nucleotide-gated ion channels. J Biol Chem 278(21) : 18705-18708, 2003.*

Randrianarison-Jewtoukoff et all. Recombinant adenoviruses as vaccines. Biologicals 23: 145-157, 1995.*

Luck et al., Molecular Endocrinology 1991, vol. 5(12): pp. 1880-1886.*

(Continued)

*Primary Examiner*—Christine J. Saoud
*Assistant Examiner*—Jon M Lockard
(74) *Attorney, Agent, or Firm*—Medlen & Carrol LLP

(57) ABSTRACT

The present invention provides modified cyclic nucleotide gated (CNG) channels. In particularly preferred embodiments, the modified CNG channels exhibit increased sensitivity and specificity for cAMP, as compared to wild-type CNG channels. In additional embodiments, regulation by $Ca^{2+}$-calmodulin has been removed in the modified CNG channels. Convenient optical methods for detecting changes in cAMP, taking advantage of the $Ca^{2+}$ permeability of the channel are also provided by the present invention. In addition, electrophysiological methods are further provided.

17 Claims, 22 Drawing Sheets

OTHER PUBLICATIONS

Stuart et al., Lancet. 2004, vol. 364(9442): pp. 1343-1360.*
Adams et al., "Fluorescence ratio imaging of cyclic AMP in single cells," *Nature*, 349:694-697 [1991].
Ahluawalia and Rhoads, "Selective inhibition of cyclic AMP and cyclic GMP phosphodiesterases of cardiac nuclear fraction," *Biochem. Pharmacol.*, 31:665-669 [1992].
Ahn et al., "Effects of selective inhibitors on cyclic nucleotide phospho-dieterases of rabbit aorta," *Biochem. Pharmacol.*, 38:3331-3339 [1989].
Akita and Kuba, "Functional triads consisting of ryanodine receptors, $Ca^{2+}$ -activated $K^+$ channels in bullfrog sympathetic neurons," *J. Gen. Physiol.*, 116:697-720 [2000].
Alvarez et al., "Regulation of cyclic AMP metabolism in human platelets: Sequential activation of adenylate cyclase and cyclic AMP phosphodiesterase by prostaglandins," *Mol. Pharmacol.*, 20:302-309 [1981].
Bacskai et al., Spatially resolved dynamics of cAMP and protein kinase A subunits in *Aplysia* sensory neurons, *Science*, 260:222-226 [1993].
Baylor et al., "The membrane current of single rod outer segments," *J. Physiol.*, 288:589-611 [1979].
Beavo, "Multiple isozymes of cyclic nucleotide phosphodieterase," *Adv. Second Messenger Phosphoprot. Res.*, 22:1-38 [1988].
Beavo, "Cyclic nucleotide phosphodieterases: Functional implications of multiple isoforms," *Physiol. Rev.*, 75:725-748 [1995].
Bolger et al., "Characterization of five different proteins produced by alternatively spliced mRNAs from the human cAMP-specific phosphodiesterase PDE4D gene," *Biochem. J.*, 328:539-548 [1997].
Bolger et al., "A family of human phosphodieterases homologous to the *dunce* learning and memory gene product of *Drosophila melanogaster* are potential targets for antidepressant drugs," *Mol. Cell. Biol.*, 13:6558-6571 [1993].
Boshart et al., "A very strong enhancer is located upstream of an immediate early gene of human cytomegalovirus," *Cell*, 41:521-530 [1985].
Bridge et al., "The relationship between charge movements associated with $I_{Ca}$ and $I_{Na-Co}$ in cardiac myocytes," *Science*, 248:376-378 [1990].
Broillet, "A single intracellular cysteine residue is responsible for the activation of the olfactory cyclic nucleotide-gated channel by NO," *J. Biol. Chem.*, 275:15135-15141 [2000].
Brooker, "Oscillation of cyclic adenosine monophosphate concentration during the myocardial contraction cycle," *Science*, 182:933-934 [1973].
Chen et al., "Slowed recovery of rod photoresponse in mice lacking the GTPase accelerating protein RGS9-1," *Nature*, 403:557-560 [2000].
Chen-Izu et al., "$G_1$-dependent localization of $\beta_2$-adrenergic receptor signaling to L-type $Ca^{2+}$ channels," *Biophys. J.*, 79:2547-2556 [2000].
Conti et al., "Recent progress in understanding the hormonal regulation of phosphodieterases," *Endocrine Res.*, 16:370-389 [1995].
Cooper et al., "$Ca^{2+}$ -sensitive adenylyl cyclases," *Adv. Second Messenger Phosphoprotein Res.*, 32:23-51 [1998].
Cooper et al., "Adenynyl cyclases and the interaction between calcium and cAMP signalling," *Nature*, 374:421-424 [1995].
Coste and Grondin, "Characterization of a novel potent and specific inhibitor of type V phosphodiesterase," *Biochem. Pharmacol.*, 50:1577-1585 [1995].
Davare et al., "A $\beta_2$ adrenergic receptor signaling complex assembled with the $Ca^{2+}$ channel $Ca_v1.2$," *Science*, 293:98-101 [2001].
Dhallan et al., "Primary structure and functional expression of a cyclic nucleotide-activated channel from olfactory neurons," *Nature*, 347:184-187 [1990].
Dijkema, et al., "Cloning and expression of the chromosomal immune interferon gene of the rat," *EMBO J.*, 4:761-767 [1985].
Drummond and Perrot-Yee, "Enzymatic hydrolysis of adenosine 3'-5'-phosphoric acid," *J. Biol. Chem.*, 236:1126-1129 [1961].
Epstein et al., "Catalytic and kinetic properties of purified high-affinity cyclic AMP phosphodiesterase from dog kidney," *Arch. Biochem. Biophys.*, 218:119-133 [1982].
Evans et al., "Muscarinic cholinergic receptors of two cells lines that regulate cyclic AMP metabolism by different molecular mechanisms," *Mol. Pharmacol.*, 26:395-404 [1984].
Fagan et al., "Adenovirus encoded cyclic nucleotide-gated channels: A new methodology for monitoring cAMP in living cells," *FEBS Lett.*, 500:85-90 [2001].
Fagan et al., "Functional co-localization of transfected $Ca^{2+}$ -stimulable adenylyl cyclases with capacitative $Ca^{2+}$ entry sites," *J. Biol. Chem.*, 271:12438-12444 [1996 ].
Fagan et al., "Adenovirus-mediated expression of an olfactory cyclic nucleotide-gated channel regulates the endogenous $Ca^{2+}$ -inhibitable adenylyl cyclase in C6-2B glioma cells," *J. Biol. Chem.*, 274:12445-12453 [1999].
Fagan et al., "Regulation of a $Ca^{2+}$ -sensitive adenylyl cyclase in an excitable cell," *J. Biol. Chem.*, 275:40187-40194 [2000].
Fawcett et al., "Molecular cloning and characterization of a distinct human phosphodiesterase gene family: PDE11A," *Proc. Natl. Acad. Sci. USA* 97:3702-3707 [2000].
Feliciello et al., "The biological functions of A-kinase anchor proteins," *J. Mol. Biol.*, 308:99-114 [2001].
Finch and Augustine, "Local calcium signalling by inositol-1,4,5-triphosphate in Purkinje cell dendrites," *Nature*, 396:753-756 [1998].
Finn et al., "Cyclic nucleotide-gated ion channels: an extended family with diverse functions," *Ann. Rev. Physiol.*, 58:395-426 [1996].
Fisher et al., "Isolation and characterization of PDE9A, a novel human cGMP-specific phosphodiesterase," *J. Biol. Chem.*, 273:15559-15564 [1998].
Francis and Corbin, "Cyclic nucleotide-dependent protein kinases: Intracellular receptors for cAMP and cGMP action," *Crit. Rev. Clin. Lab. Sci.*, 36:275-328 [1999].
Frings et al., "Profoundly different calcium permeation and blockage determine the specific function of distinct cyclic nucleotide-gated channels," *Neuron*, 15:169-179 [1995].
Fung et al., "Flow of information in the light-triggered cyclic nucleotide cascade of vision," *Proc. Natl. Acad. Sci. USA*, 78:152-156 [1981].
Gardner et al., "Cloning and characterization of the human and mouse PDE7B, a novel cAMP-specific cyclic nucleotide phosphodiesterase," *Biochem. Biophys. Res. Commun.*, 272:186-192 [2000].
Gautvik et al., "Relationship between stimulated prolactin release from GH cells and cyclic AMP degradation and formation," *Mol. Cell. Endocrinol.*, 26:295-308 [1982].
Gómez-Foix et al., "Adenovirus-mediated transfer of the muscle glycogen phosphorylase gene into hepatocytes confers altered regulation of glycogen metabolism," *J. Biol. Chem.*, 267:25129-25134 [1992].
Gorozyca et al., "Purification and physiological evaluation of a guanylate cyclase activating protein from retinal rods," *Proc. Natl. Acad. Sci. USA*, 91:4014-4018 [1994].
Gorman et al., "The Rous sarcoma virus long terminal repeat is a strong promoter when introduced into variety of eukaryotic cells by DNA-mediated transfection," *Proc. Natl. Acad. Sci. USA*, 79:6777-6781 [1982].
Gray et al., "Regulation of ion channels by cAMP-dependent protein kinase and A-kinase anchoring proteins," *Curr. Opin. Neurobiol.*, 8:330-334 [1998].
Harootunian et al., "Movement of the free catalytic subunit of cAMP-dependent protein kinase into and out of the nucleus can be explained by diffusion," *Mol. Biol. Cell*, 4:993-1002 [1993].
Harrison et al., "Isolation and comparison of bovine heart cGMP-inhibited and cGMP-stimulated phosphodieterases," *Meth. Enzymol.*, 15:685-702 [1988].
He et al., "RGS9, a GTPase accelerator for phototransduction," *Neuron*, 20:95-102 [1998].
He et al., "A simplified system for generating recombinant adenoviruses," *Proc. Natl. Acad. Sci. USA*, 95:2509-2514 [1998].

Hempel et al., "Spatio-temporal dynamics of cyclic AMP signals in an intact neural circuit," *Nature*, 384:166-169 [1996].
Hetman et al., "Cloning and characterization of PDE7B; a cAMP-specific phosphodiesterase," *Proc. Natl. Acad. Sci. USA*, 97:472-476 [2000].
Hoffmann et al., "The MAP kinase ERK2 inhibits the cyclic AMP-specific phosphodiesterase HSPDE4D3 by phosphorylating it at Ser579," *EMBO J.*, 18:893-903 [1999].
Holck et al., "Studies on the mechanism of positive inotropic activity of Ro 13-6438, a structurally novel cardiotonic agent with vasodilating properties," *J. Cardiovasc. Pharm.*, 6:520-530 [1984].
Houslay et al., "The multienzyme PDE4 cyclic adenosine monophosphate-specific phosphodiesterase family: intracellular targeting, regulation, and selective inhibition of compounds exerting anti-inflammatory and antidepressant actions," *Adv. Pharmacol.*, 44:225-342 [1998].
Jaggar et al., "Calcium sparks in smooth muscle," *Am. J. Physiol. Cell Physiol.*, 278:C235-C256 [2000].
Jordan et al., "Transfecting mammalian cells: optimization of critical parameters affecting calcium-phosphate precipitate formation," *Nucl. Acids Res.*, 24:596-601 [1996].
Jurevicius and Fischmeister, "cAMP compartmentation is responsible for a local activation of cardiac $Ca^{2+}$ channels by β-adrenergic agonists," *Proc. Natl. Acad. Sci. USA*, 93:295-299 [1996].
Kim et al., "Use of the human elongation factor 1α promoter as a versatile and efficient expression system," *Gene*, 91:217-223 [1990].
Koch and Stryer, "Highly cooperative feedback control of retinal rod guanylate cyclase by calcium ions," *Nature*, 334:64-66 [1988].
Koutalos et al., "Characterization of guanylate cyclase activity in single retinal rod outer segments," *J. Gen. Physiol.*, 106:863-890 [1995].
Koutalos et al., "The cGMP-phosphodiesterase and its contribution to sensitivity regulation in retinal rods," *J. Gen. Physiol.*, 106:891-921 [1995].
Lagnado and Baylor, "Signal flow in visual transduction," Neuron 8:995-1002 [1992].
Leblanc and Hume, "Sodium current-induced release of calcium from cardiac sarcoplasmic reticulum," *Science*, 248:372-376 [1990].
Leskov et al., "The gain of rod phototransduction: Reconciliation of biochemical and electrophysiological measurements," *Neuron*, 27:525-537 [2000].
Liu et al., "Calcium-calmodulin modulation of the olfactory cyclic nucleotide-gated cation channel," *Science*, 266:1348-1354 [1994].
Lorenz and Wells, "Potentiation of the effects of sodium nitroprusside and of isoproterenol by selective phosphodiesterase inhibitors," *Mol. Pharmacol.*, 23:424-430 [1993].
Loughney et al., "Isolation and characterization of cDNAs encoding PDE5A, a human cGMP-binding, cGMP-specific 3',5'-cyclic nucleotide phosphodiesterase," *Gene*, 216:139-147 [1998].
Loughney et al., "Isolation and characterization of cDNAs corresponding to two human calcium calmodulin-regulated 3',5'-cyclic nucleotide phosphodiesterases," *J. Biol. Chem.*, 271:796-806 [1996].
Ma et al., "Requirement of the inositol trisphosphate receptor for activation of store-operated $Ca^{2+}$ channels," *Science*, 287:1647-1651 [2000].
MacKenzie and Houslay, "Action of rolipram on specific PDE4 cAMP phosphodiesterase isoforms and on the phosphorylation of cAMP-response-element-binding protein (CREB) and p38 mitogen-activated protein (MAP) kinase in U937 monocytic cells," *Biochem. J.*, 347:571-578 [2000].
Macphee et al., "Phosphorylation results in activation of a cAMP phosphodiesterases in human platelets," *J. Biol. Chem.*, 263:10353-10358 [1988].
Maniatis et al., "Regulation of inducible and tissue-specific gene expression," *Science*, 236:1237 [1987].
Martens et al., "Isoform-specific localization of voltage-gated $K^1$ channels to distinct lipid raft populations," *J. Biol. Chem.*, 276:8409-8414 [2001].
Martin and Fuchs, The dependence of calcium-activated potassium currents on membrane potential, *Proc. Roy. Soc. London B. Biol. Sci.*, 250:71-76 [1992].
McPhee et al., "Association with the SRC family tyrosyl kinase LYN triggers a conformational change in the catalytic region of human cAMP-specific phosphodiesterase HSPDE4A4B," *J. Biol. Chem.*, 274:11796-11810 [1999].
Mizushima and Nagata, "pEF-BOS, a powerful mammalian expression vector," *Nucl. Acids. Res.*, 18:5322 [1990].
Molday, "Photoreceptor membrane proteins, phototransduction, and retinal degenerative diseases," *Invest. Ophthalmol. Vis. Sci.*, 39:2493-2513 [1998].
Mollard et al., "Limited accumulation of cyclic AMP underlines a modest vasoactive-intestinal-peptide-mediated increase in cytosolic [$Ca^{2+}$] transients in GH3 pituitary cells," *Biochem. J.*, 284:637-640 [1992].
Neher and Augustine, "Calcium gradients and buffers in bovine chromaffin cells," *J. Physiol.*, 450:273-301 [1992].
Nemoz et al., "Selective inhibition of one of the cyclic AMP phosphodiesterases from rat brain by the neurotropic compound rolipram," *Biochem. Pharmacol.*, 34:2997-3000 [1995].
Nikonov et al., "The role of steady phosphodieterase activity in the kinetics and sensitivity of the light-adapted salamander rod photoresponse," *J. Gen. Physiol.*, 116:795-824 [2000].
Oakes et al., "Incomplete hydrolysis of the calcium indicator precursor Fura-2 pentaacetoxymethyl ester (Fura-2 AM) by cells," *Anal. Biochem.*, 169:159-166 [1988].
Ogreid and Doskeland, "Cyclic nucleotides modulate the release of [$^3$H]adenosine cyclic 3',5'-phosphate bound to the regulatory moiety of protein kinase I by the catalytic subunit of the kinase," *Biochem.*, 22:1686-1696 [1983].
Orlicky and Schaack, "Adenovirus transduction of 3T3-L1 cells," *J. Lipid Res.*, 42:460-466 [2001].
Podzuweit et al., "Isozyme selective inhibition of the cGMP-stimulated cyclic nucleotide phosphodiesterases by erythro-9-(2-hydroxy-3-nonyl) adenine," *Cell. Signal.*, 7:733-738 [1995].
Polans et al., "Turned on by $Ca^{2+}$! The physiology and pathology of $Ca^{2+}$-binding proteins in the retina," *Trends Neurosci.*, 19:547-554.
Pugh and Lamb, "Amplication and kinetics of the activation steps in phototransduction," *Biochim. Biophys. Acta*, 1141:111-149 [1993].
Pugh et al., "Photoreceptor guanylate cyclases: A review," *Biosci. Rep.*, 17:429-473 [1997].
Rich et al., "Cyclic nucleotide-gated channels colocalize with adenylyl cyclase in regions of restricted cAMP diffusion," *J. Gen. Physiol.*, 116:147-161 [2000].
Rich et al., "*In vivo* assessment of local phosphodieterase activity using tailored cyclic nucleotide-gated channels as cAMP sensors," *J. Gen. Physiol.*, 118:63-77 [2001].
Rich et al., "A uniform extracellular stimulus triggers distinct cAMP signals in different compartments of a simple cell," *Proc. Natl. Acad. Sci. USA*, 98:13049-13054 [2001].
Roberts et al., "Colocalization of ion channels involved in frequency selectivity and synaptic transmission at presynaptic active zones of hair cells," *J. Neurosci.*, 10:3664-3684 [1990].
Rosman et al., "Isolation and characterization of human cDNAs encoding a cGMP-stimulated 3',5'-cyclic nucleotide phosphodiesterase," *Gene*, 191:89-95 [1997].
Rybin et al., "Differential targeting of β-adrenergic receptor subtypes and adenylyl cyclase to cardiomyocyte caveolae," *J. Biol. Chem.*, 275:41447-41457 [2000].
Schaack et al., "Efficient selection of recombinant adenoviruses by vectors that express β-galactosidase," *J. Virol.*, 69:3920-3923 [1995].
Schneggenburger et al., "Fractional contribution of calcium to the cation current through glutamate receptor channels," *Neuron*. 11:133-143 [1993].
Sletholt et al., "Effects of calmodulin antagonists on hormone release and cyclic AMP levels in $GH_3$ pituitary cells," *Acta. Physiol. Scand.*, 130:333-343 [1987].
Soderling et al., "Identification and characterization of a novel family of cyclic nucleotide phosphodiesterases," *J. Biol. Chem.*, 273:15553-15558 [1998].

Soderling et al., "Cloning and characterization of a cAMP-specific cyclic nucleotide phosphodiesterase," *Proc. Natl. Acad. Sci. USA*, 95:8991-8996 [1998].

Soderling et al., "Isolation and characterization of a dual-substrate phosphodiesterase gene family: PDE10A," *Proc. Natl. Acad. Sci. USA*, 96:7071-7076 [1999].

Steinberg and Brunton, "Compartmentation of G protein-coupled signaling pathways in cardia myocytes," *Annu. Rev. Pharmocol. Toxicol.*, 41:751-773 [2001].

Stryer, "Visual excitation and recovery," *J. Biol. Chem.*, 266:10711-10714 [1991].

Sunahara et al., "Complexity and diversity of mammalian adenylyl cyclases," *Ann. Rev. Pharmacol. Toxicol.*, 36:461-480 [1996].

Svoboda et al., "Direct measurement of coupling between dendritic spines and shafts," *Science*, 272:716-719 [1996].

Takechi et al., "A new class of synaptic response involving calcium release in dentric spines," *Nature*, 396:757-760 [1998].

Thomas and Hoffman, "Isoform-specific sensitization of adenylyl cyclase activity by prior activation of inhibitory receptors: Role of βγ subunits in transducing enhanced activity of the type VI isoform," *Mol. Pharmacol.*, 49:907-914 [1996].

Trivedi and Kramer, "Real-time patch-cram detection of intracellular cGMP reveals long-term suppression of responses to NO and muscarinic agonists," *Neuron*, 21:895-906 [1998].

Tsang et al., "Role for target enzyme in deactivation of photoreceptor G protein *in vivo," Science*, 282:117-121 [1998].

Uetsuki et al., "Isolation and characterization of the human chromosomal gene for polypeptide chain elongation factor-1α," *J. Biol. Chem.*, 264:5791 [1989].

Varnum et al., "Molecular mechanism for ligand discrimination of cyclic nucleotide-gated channels," *Neuron*, 15:619-625 [1995].

Voss, et al., "The role of enhancers in the regulation of cell-type-specific transcriptional control," *Trends Biochem. Sci.*, 11:287-289 [1986].

Walsh et al., "An adenosine 3',5' -monophosphate-dependent protein kinase from rabbit skeletal muscle," *J. Biol. Chem.*, 243:3763-3765 [1968].

Whalin et al., "Phosphodiesterase II, the cGMP-activatable cyclic nucleotide phosphodieterase, regulates cyclic AMP metabolism in PCI2 cells," *Mol. Pharmacol.*, 39:711-717 [1991].

Yarfitz and Hurley, "Transduction mechanisms of vertebrate and invertebrate photoreceptors," *J. Biol. Chem.*, 269:14329-14332 [1994].

Yau, "Phototransduction mechanism in retinal rods and cones," *Invest. Ophthalmol. Vis. Sci.*, 35:9-32 [1994].

Zaccolo et al., "A genetically encoded, fluorescent indicator for cyclic AMP in living cells," *Nat. Cell. Biol.*, 2:25-29 [2000].

Zolle et al., "Activation of the particulate and not the soluble guanylate cyclase leads to the inibition of $Ca^{2+}$ extrusion through localized elevation of cGMP," *J. Biol. Chem.*, 275:25892-25899 [2000].

Adams et al., "Imaging of cAMP signals and A-kinase translocation in single living cells," *Adv. Second Messenger Phosphoprotein Res.*, 28:167-170 [1993].

Brown et al., "Movement of gating machinery during the activation of rod cyclic nucleotide-gated channels," *Biophys. J.*, 75:825-833 [1998].

Finn and Yau, "C-terminus involvement in the gating of cyclic nucleotide-activated channels as revealed by $Ni^{2+}$ and NEM," abstract presented at the 39th Annual Biophysical Society Meeting and published in the *Biophys. J.*, 68:A253 Abstract No. W-PM-C6 [1995].

Gordon et al., "Direct interaction between amino- and carboxyl-terminal domains of cyclic nucleotide-gated channels," *Neuron*, 19:431-441 [1997].

Pugh "Transfected cyclic-nucleotide-gated channels as biosensors," *J. Gen. Physiol.*, 116:143-145 [2000].

Rich et al., "Localized, single-cell measure of cyclic AMP using cyclic nucleotide-gated channels," abstract presented at the 53rd Annual Meeting of the Society of General Physiologists and published in *J. Gen. Phsyiol.*, 114:16a Abstract No. 52 [1999].

Rich et al., "Regulation of cAMP within diffusionally-restricted microdomains," abstract presented at the 44th Annual Meeting of the Biophysical Society and published in *Biophy. J.*, 78:391A Abstract No. 2305-Plat [2000].

Rich et al., "Improved single-cell measurement reveals distinct cAMP signals in different cellular compartments," abstract presented at the 40th American Society of Cell Biology Annual Meeting and published in *Molecular Biology of the Cell* (*Supplement*), 11:249a Abstract No. 1298 [2000].

Rich et al., "The role of phosphodiesterase in shaping cAMP signals near the plasma membrane," abstract presented at the 45th Annual Meeting of the Biophysical Society and published in *Biophys. J.*, 80:250a [2001].

Rich et al., "Measurement of localized, transient cAMP signals in single cells," abstract presented at the 45th Annual Meeting of the Biophysical Society and published in *Biophys. J.*, 80:345a [2001].

Zong et al., "Three amino acids in the C-linker are major determinants of gating in cyclic nucleotide-gated channels," *EMBO J.*, 17:353-362 [1998].

* cited by examiner

```
1 aattccaaca ttgaagatgg cttctccagg ggccggggca ccctgatagg ctctcaagct
61 cacctagctg tgttatgtgc tccattgggc ctctgtcagc tgctatcaga cagcgtgggc
121 tagatctctg attgggaagc tgctgctgtt tgttggggtc tcagagaacc ttccctggct
181 ggacaacaga agaaacagga aatctcttca gctttcagtg ctcatgagct cccaagagct
241 tctctttgat tggagctggt gtggacagaa caacagatgt tgactgtgac ctcaggactc
301 tgaaaccatc tgactggtga gagccctgga tttacatgga tgatgaccga aaaatccaat
                                           *
361 ggtgtgaaaa gctctccagc taataaccat aaccatcatc ctcctccttc tatcaaggcc
421 aatggcaaag atgaccacag ggcaggaagc agaccacagt ctgtggcagc tgatgatgac
481 acttctccag aactacaaag gctggcagag atggataccc ctcggagggg gaggggtggc
541 ttccaaagga ttgttcgcct ggtgggggtc atcagggact gggccaacaa gaatttccgt
601 gaagaggaac caaggcctga ctccttccta gagcgtttcc gtgggccaga actccagact
661 gtgacaaccc atcaggggga tgacaaaggc ggcaaggacg gcgagggaaa gggcaccaaa
721 aagaaatttg aactgtttgt tttggaccca gccggagact ggtattaccg ttggttgttt
781 gtcattgcca tgcctgttct ttacaactgg tgcctgttgg tggccagagc ctgcttcagt
841 gatctacaga gaaactattt tgtggtatgg ctggtgctgg actacttctc agacactgtc
901 tatatcgcag acctcatcat tcggctgcgc acaggcttcc tagaacaggg gctcttggtc
961 aaagatccca agaaattgcg agacaactat attcacactt tgcagttcaa attggatgtg
1021 gcttctatca ttcccactga ccttatctat tttgctgtgg gtatccacag ccctgaggta
1081 cgcttcaacc gtctattaca ctttgcccgt atgtttgagt tctttgaccg cactgagaca
1141 cgcaccagct accccaacat cttccgaatc agcaatctgg tcctttacat cttggtcatc
1201 atccactgga atgcttgtat ttattatgtt atttctaagt ccattggctt tggagttgac
1261 acctgggttt accccaacat tactgaccct gaatatggct acctggctag agagtacatt
1321 tactgtcttt actggtccac actgaccctc accaccattg gagagacacc acccccctgta
1381 aaggatgagg agtacctatt tgtcatcttt gacttcttga ttggtgtcct catctttgcc
1441 actattgtgg gaaatgtggg ctccatgatc tccaacatga atgccacacg agcagagttc
1501 caggccaaga ttgatgctgt caaacactac atgcagttcc gaaaggtcag caaagacatg
1561 gaagccaagg tcatcaaatg gtttgactac ttgtggacca ataagaagac agtagatgaa
1621 cgagaagtcc tcaagaacct gccagcaaag ctcagggctg agatagccat taatgttcac
```

FIGURE 1 (cont.)

```
1681 ttgtccactc tgaagaaagt gcgcatattc caggattgtg aagctggcct actggtggaa
1741 ctggtactga agcttcgtcc tcaggtcttt agtcctggag attatatttg ccgtaagggg
1801 gacattggca aggaaatgta catcatcaag gagggcaagt tggcagtggt agctgatgat
1861 ggcgtgactc agtatgcctt gctctcagct gggagctgct ttggtgagat tagtatcctt
1921 aacattaagg gtagcaaaat gggcaatcga cgtactgcta atatccgtag cctgggctac
1981 tcagatctct tctgcttgtc caaggacgat cttatggaag ctgtaactga gtatcctgat
2041 gccaagaagg tcctggagga acggggtagg gagatcctga tgaagatggg tctactggat
2101 gagaatgaag tggcagctag tatggaggta gatgttcagg agaagctgga acagttggag
2161 acaaacatgg ataccttgta cactcgcttt gcccgcctgc tggctgagta cactggggcc
2221 cagcagaagc tcaagcaacg catcacagtg ctagagacca agatgaaaca gaaccatgag
2281 gatgattatc tatcagatgg gataaacact cctgagccaa ctgctgctga ataaccataa
                                                             *
2341 gtgactatcc agccttggtc tgactccagg agttagaagt gctgtataga actttacatt
2401 tacacacatt atgctcatgt ccctctgaac tctccccaaa gccatgctga ggcttaaggt
2461 tttgactaca tcttgaagtc cccctctaag tccagctaac agtcaagctt gtggacaatg
2521 cagatcatgt gggttgaatt tccaagagct tgacctccta tgtctgaaaa gggatcagag
2581 actagctaaa ttgtccttcc tggggctttt ctggtactag atacctagac agtgttctct
2641 gaagaacact gtgcacaatg cctgactccc tttagtttct ttatatctag tcactcccta
2701 ctgtattctg ccccaaatac ctttttaat gtgttctcta agcagcctgt ttccatgtac
2761 atgtataaat ttaagaattg gctgcaaaca ctgggccccc taaactgtct cccaaggcat
2821 gcaagggccg tgaggggagt ggtagggtgg gtttgagtgt gtgtgctcag ggtcatactt
2881 ccttgtcaga caatgtcact atgagaagag gtggctggca gctttggcca tcacaccttt
2941 atgcacacaa gttctgaaga gtttgtgaat gctgagatac tgtgaattag agccacttaa
3001 aagttaataa attcttttca gctaaaa
```

```
1 aattccaaca ttgaagatgg cttctccagg ggccggggca ccctgatagg ctctcaagct
61 cacctagctg tgttatgtgc tccattgggc ctctgtcagc tgctatcaga cagcgtgggc
121 tagatctctg attgggaagc tgctgctgtt tgttggggtc tcagagaacc ttccctggct
181 ggacaacaga agaaacagga aatctcttca gctttcagtg ctcatgagct cccaagagct
241 tctctttgat tggagctggt gtggacagaa caacagatgt tgactgtgac ctcaggactc
301 tgaaaccatc tgactggtga gagccctgga tttacatgga tgatgaccga aaaatccaat
                                              *
361 ggtgtgaaaa gctctccagc taataaccat aaccatcatc ctcctccttc tatcaaggcc
421 aatggcaaag atgaccacag ggcaggaagc agaccacagt ctgtggcagc tgatgatgac
481 acttctccag aactacaaag gctggcagag atggataccc ctcggagggg gaggggtggc
541 ttccaaagga ttgttcgcct ggtgggggtc atcagggact gggccaacaa gaatttccgt
601 gaagaggaac caaggcctga ctccttccta gagcgtttcc gtgggccaga actccagact
661 gtgacaaccc atcaggggga tgacaaaggc ggcaaggacg gcgagggaaa gggcaccaaa
721 aagaaatttg aactgtttgt tttggaccca gccggagact ggtattaccg ttggttgttt
781 gtcattgcca tgcctgttct ttacaactgg tgcctgttgg tggccagagc ctgcttcagt
841 gatctacaga gaaactattt tgtggtatgg ctggtgctgg actacttctc agacactgtc
901 tatatcgcag acctcatcat tcggctgcgc acaggcttcc tagaacaggg gctcttggtc
961 aaagatccca agaaattgcg agacaactat attcacactt tgcagttcaa attggatgtg
1021 gcttctatca ttcccactga ccttatctat tttgctgtgg gtatccacag ccctgaggta
1081 cgcttcaacc gtctattaca ctttgcccgt atgtttgagt tctttgaccg cactgagaca
1141 cgcaccagct accccaacat cttccgaatc agcaatctgg tcctttacat cttggtcatc
1201 atccactgga atgcttgtat ttattatgtt atttctaagt ccattggctt tggagttgac
1261 acctgggttt accccaacat tactgaccct gaatatggct acctggctag agagtacatt
1321 tactgtcttt actggtccac actgaccctc accaccattg gagagacacc accccctgta
1381 aaggatgagg agtacctatt tgtcatcttt gacttcttga ttggtgtcct catctttgcc
1441 actattgtgg gaaatgtggg ctccatgatc tccaacatga atgccacacg agcagagttc
1501 caggccaaga ttgatgctgt caaacactac atgcagttcc gaaaggtcag caaagacatg
1561 gaagccaagg tcatcaaatg gtttgactac ttgtggacca ataagaagac agtagatgaa
1621 cgagaagtcc tcaagaacct gccagcaaag ctcagggctg agatagccat taatgttcac
```

FIGURE 2 (cont.)

```
1681 ttgtccactc tgaagaaagt gcgcatattc caggattggg aagctggcct actggtggaa
1741 ctggtactga agcttcgtcc tcaggtcttt agtcctggag attatatttg ccgtaagggg
1801 gacattggca aggaaatgta catcatcaag gagggcaagt tggcagtggt agctgatgat
1861 ggcgtgactc agtatgcctt gctctcagct gggagctgct ttggtgagat tagtatcctt
1921 aacattaagg gtagcaaaat gggcaatcga cgtactgcta atatccgtag cctgggctac
1981 tcagatctct tctgcttgtc caaggacgat cttatggaag ctgtaactga gtatcctgat
2041 gccaagaagg tcctggagga acggggtagg gagatcctga tgaagatggg tctactggat
2101 gagaatgaag tggcagctag tatggaggta gatgttcagg agaagctgga acagttggag
2161 acaaacatgg ataccttgta cactcgcttt gcccgcctgc tggctgagta cactggggcc
2221 cagcagaagc tcaagcaacg catcacagtg ctagagacca agatgaaaca gaaccatgag
2281 gatgattatc tatcagatgg gataaacact cctgagccaa ctgctgctga ataaccataa
                                                           *
2341 gtgactatcc agccttggtc tgactccagg agttagaagt gctgtataga actttacatt
2401 tacacacatt atgctcatgt ccctctgaac tctccccaaa gccatgctga ggcttaaggt
2461 tttgactaca tcttgaagtc cccctctaag tccagctaac agtcaagctt gtggacaatg
2521 cagatcatgt gggttgaatt tccaagagct tgacctccta tgtctgaaaa gggatcagag
2581 actagctaaa ttgtccttcc tggggctttt ctggtactag atacctagac agtgttctct
2641 gaagaacact gtgcacaatg cctgactccc tttagtttct ttatatctag tcactcccta
2701 ctgtattctg ccccaaatac ctttttttaat gtgttctcta agcagcctgt ttccatgtac
2761 atgtataaat ttaagaattg gctgcaaaca ctgggccccc taaactgtct cccaaggcat
2821 gcaagggccg tgaggggagt ggtagggtgg gtttgagtgt gtgtgctcag ggtcatactt
2881 ccttgtcaga caatgtcact atgagaagag gtggctggca gctttggcca tcacaccttt
2941 atgcacacaa gttctgaaga gtttgtgaat gctgagatac tgtgaattag agccacttaa
3001 aagttaataa attcttttca gctaaaa
```

```
1 aattccaaca ttgaagatgg cttctccagg ggccggggca ccctgatagg ctctcaagct
61 cacctagctg tgttatgtgc tccattgggc ctctgtcagc tgctatcaga cagcgtgggc
121 tagatctctg attgggaagc tgctgctgtt tgttggggtc tcagagaacc ttccctggct
181 ggacaacaga agaaacagga aatctcttca gctttcagtg ctcatgagct cccaagagct
241 tctctttgat tggagctggt gtggacagaa caacagatgt tgactgtgac ctcaggactc
301 tgaaaccatc tgactggtga gagccctgga tttacatgga tgatgaccga aaaatccaat
                                                *
361 ggtgtgaaaa gctctccagc taataaccat aaccatcatc ctcctccttc tatcaaggcc
421 aatggcaaag atgaccacag ggcaggaagc agaccacagt ctgtggcagc tgatgatgac
481 acttctccag aactacaaag gctggcagag atggatacc
541
601 c ctaggcctga ctccttccta gagcgtttcc gtgggccaga actccagact
661 gtgacaaccc atcaggggga tgacaaaggc ggcaaggacg gcgagggaaa gggcaccaaa
721 aagaaatttg aactgtttgt tttggaccca gccggagact ggtattaccg ttggttgttt
781 gtcattgcca tgcctgttct ttacaactgg tgcctgttgg tggccagagc ctgcttcagt
841 gatctacaga gaaactattt tgtggtatgg ctggtgctgg actacttctc agacactgtc
901 tatatcgcag acctcatcat tcggctgcgc acaggcttcc tagaacaggg gctcttggtc
961 aaagatccca agaaattgcg agacaactat attcacactt tgcagttcaa attggatgtg
1021 gcttctatca ttcccactga ccttatctat tttgctgtgg gtatccacag ccctgaggta
1081 cgcttcaacc gtctattaca ctttgcccgt atgtttgagt tctttgaccg cactgagaca
1141 cgcaccagct accccaacat cttccgaatc agcaatctgg tcctttacat cttggtcatc
1201 atccactgga atgcttgtat ttattatgtt atttctaagt ccattggctt tggagttgac
1261 acctgggttt accccaacat tactgaccct gaatatggct acctggctag agagtacatt
1321 tactgtcttt actggtccac actgaccctc accaccattg gagagacacc accccctgta
1381 aaggatgagg agtacctatt tgtcatcttt gacttcttga ttggtgtcct catctttgcc
1441 actattgtgg gaaatgtggg ctccatgatc tccaacatga atgccacacg agcagagttc
1501 caggccaaga ttgatgctgt caaacactac atgcagttcc gaaaggtcag caaagacatg
1561 gaagccaagg tcatcaaatg gtttgactac ttgtggacca ataagaagac agtagatgaa
1621 cgagaagtcc tcaagaacct gccagcaaag ctcagggctg agatagccat taatgttcac
```

FIGURE 3 (cont.)

```
1681 ttgtccactc tgaagaaagt gcgcatattc caggattggg aagctggcct actggtggaa
1741 ctggtactga agcttcgtcc tcaggtcttt agtcctggag attatatttg ccgtaagggg
1801 gacattggca aggaaatgta catcatcaag gagggcaagt tggcagtggt agctgatgat
1861 ggcgtgactc agtatgcctt gctctcagct gggagctgct ttggtgagat tagtatcctt
1921 aacattaagg gtagcaaaat gggcaatcga cgtactgcta atatccgtag cctgggctac
1981 tcagatctct tctgcttgtc caaggacgat cttatggaag ctgtaactga gtatcctgat
2041 gccaagaagg tcctggagga acggggtagg gagatcctga tgaagatggg tctactggat
2101 gagaatgaag tggcagctag tatggaggta gatgttcagg agaagctgga acagttggag
2161 acaaacatgg ataccttgta cactcgcttt gcccgcctgc tggctgagta cactggggcc
2221 cagcagaagc tcaagcaacg catcacagtg ctagagacca agatgaaaca gaaccatgag
2281 gatgattatc tatcagatgg gataaacact cctgagccaa ctgctgctga ataaccataa
                                                               *
2341 gtgactatcc agccttggtc tgactccagg agttagaagt gctgtataga actttacatt
2401 tacacacatt atgctcatgt ccctctgaac tctccccaaa gccatgctga ggcttaaggt
2461 tttgactaca tcttgaagtc cccctctaag tccagctaac agtcaagctt gtggacaatg
2521 cagatcatgt gggttgaatt tccaagagct tgacctccta tgtctgaaaa gggatcagag
2581 actagctaaa ttgtccttcc tggggctttt ctggtactag atacctagac agtgttctct
2641 gaagaacact gtgcacaatg cctgactccc tttagtttct ttatatctag tcactcccta
2701 ctgtattctg ccccaaatac ctttttttaat gtgttctcta agcagcctgt ttccatgtac
2761 atgtataaat ttaagaattg gctgcaaaca ctgggccccc taaactgtct cccaaggcat
2821 gcaagggccg tgaggggagt ggtagggtgg gtttgagtgt gtgtgctcag ggtcatactt
2881 ccttgtcaga caatgtcact atgagaagag gtggctggca gctttggcca tcacaccttt
2941 atgcacacaa gttctgaaga gtttgtgaat gctgagatac tgtgaattag agccacttaa
3001 aagttaataa attcttttca gctaaaa
```

FIGURE 4

```
   1 aattccaaca ttgaagatgg cttctccagg ggccggggca ccctgatagg ctctcaagct
  61 cacctagctg tgttatgtgc tccattgggc ctctgtcagc tgctatcaga cagcgtgggc
 121 tagatctctg attgggaagc tgctgctgtt tgttggggtc tcagagaacc ttccctggct
 181 ggacaacaga agaaacagga aatctcttca gctttcagtg ctcatgagct cccaagagct
 241 tctctttgat tggagctggt gtggacagaa caacagatgt tgactgtgac ctcaggactc
 301 tgaaaccatc tgactggtga gagccctgga tttacatgga tgatgaccga aaaatccaat
 361 ggtgtgaaaa gctctccagc taataaccat aaccatcatc ctcctccttc tatcaaggcc
 421 aatggcaaag atgaccacag ggcaggaagc agaccacagt ctgtggcagc tgatgatgac
 481 acttctccag aactacaaag gctggcagag atggataccc ctcggagggg gaggggtggc
 541 ttccaaagga ttgttcgcct ggtgggggtc atcagggact gggccaacaa gaatttccgt
 601 gaagaggaac caaggcctga ctccttccta gagcgtttcc gtgggccaga actccagact
 661 gtgacaaccc atcaggggga tgacaaaggc ggcaaggacg gcgagggaaa gggcaccaaa
 721 aagaaatttg aactgtttgt tttggaccca gccggagact ggtattaccg ttggttgttt
 781 gtcattgcca tgcctgttct ttacaactgg tgcctgttgg tggccagagc ctgcttcagt
 841 gatctacaga gaaactattt tgtggtatgg ctggtgctgg actacttctc agacactgtc
 901 tatatcgcag acctcatcat tcggctgcgc acaggcttcc tagaacaggg gctcttggtc
 961 aaagatccca agaaattgcg agacaactat attcacactt tgcagttcaa attggatgtg
1021 gcttctatca ttcccactga ccttatctat tttgctgtgg gtatccacag ccctgaggta
1081 cgcttcaacc gtctattaca ctttgcccgt atgtttgagt tctttgaccg cactgagaca
1141 cgcaccagct accccaacat cttccgaatc agcaatctgg tcctttacat cttggtcatc
1201 atccactgga atgcttgtat ttattatgtt atttctaagt ccattggctt tggagttgac
1261 acctgggttt accccaacat tactgaccct gaatatggct acctggctag agagtacatt
1321 tactgtcttt actggtccac actgaccctc accaccattg gagagacacc acccctgta
1381 aaggatgagg agtacctatt tgtcatcttt gacttcttga ttggtgtcct catctttgcc
1441 actattgtgg gaaatgtggg ctccatgatc tccaacatga atgccacacg agcagagttc
1501 caggccaaga ttgatgctgt caaacactac atgcagttcc gaaaggtcag caaagacatg
1561 gaagccaagg tcatcaaatg gtttgactac ttgtggacca ataagaagac agtagatgaa
1621 cgagaagtcc tcaagaacct gccagcaaag ctcagggctg agatagccat taatgttcac
1681 ttgtccactc tgaagaaagt gcgcatattc caggattgtg aagctggcct actggtggaa
1741 ctggtactga agcttcgtcc tcaggtcttt agtcctggag attatatttg ccgtaagggg
1801 gacattggca aggaaatgta catcatcaag gagggcaagt tggcagtggt agctgatgat
1861 ggcgtgactc agtatgcctt gctctcagct gggagctgct ttggtgagat tagtatcctt
1921 aacattaagg gtagcaaaat gggcaatcga cgtactgcta atatccgtag cctgggctac
1981 tcagatctct tctgcttgtc caaggacgat cttatggaag ctgtaactga gtatcctgat
2041 gccaagaagg tcctggagga acggggtagg gagatcctga tgaaggaagg tctactggat
2101 gagaatgaag tggcagctag tatggaggta gatgttcagg agaagctgga acagttggag
2161 acaaacatgg ataccttgta cactcgcttt gcccgcctgc tggctgagta cactggggcc
2221 cagcagaagc tcaagcaacg catcacagtg ctagagacca agatgaaaca gaaccatgag
2281 gatgattatc tatcagatgg gataaacact cctgagccaa ctgctgctga ataaccataa
2341 gtgactatcc agccttggtc tgactccagg agttagaagt gctgtataga actttacatt
2401 tacacacatt atgctcatgt ccctctgaac tctccccaaa gccatgctga ggcttaaggt
2461 tttgactaca tcttgaagtc cccctctaag tccagctaac agtcaagctt gtggacaatg
2521 cagatcatgt gggttgaatt tccaagagct tgacctccta tgtctgaaaa gggatcagag
2581 actagctaaa ttgtccttcc tggggctttt ctggtactag atacctagac agtgttctct
2641 gaagaacact gtgcacaatg cctgactccc tttagtttct ttatatctag tcactcccta
2701 ctgtattctg ccccaaatac ctttttttaat gtgttctcta agcagcctgt ttccatgtac
2761 atgtataaat ttaagaattg gctgcaaaca ctgggccccc taaactgtct cccaaggcat
2821 gcaagggccg tgaggggagt ggtagggtgg gtttgagtgt gtgtgctcag ggtcatactt
2881 ccttgtcaga caatgtcact atgagaagag gtggctggca gctttggcca tcacaccttt
2941 atgcacacaa gttctgaaga gtttgtgaat gctgagatac tgtgaattag agccacttaa
3001 aagttaataa attcttttca gctaaaa
```

NUCLEIC ACIDS ENCODING MODIFIED OLFACTORY CYCLIC NUCLEOTIDE GATED ION CHANNELS

This application claims benefit of provisional patent application U.S. Ser. No. 60/332,494, filed on Nov. 16, 2001.

This invention was made with government support under grants GM32438, NS28389, HL58344, DC00385, EY09275, from the National Institutes Health. The United States Government has certain rights in the invention.

FIELD OF THE INVENTION

The present invention provides modified cyclic nucleotide gated (CNG) channels. In particularly preferred embodiments, the modified CNG channels exhibit increased sensitivity and specificity for cAMP, as compared to wild-type CNG channels. In additional embodiments, regulation by $Ca^{2+}$-calmodulin has been removed in the modified CNG channels. Convenient optical methods for detecting changes in cAMP, taking advantage of the $Ca^{2+}$ permeability of the channel are also provided by the present invention. In addition, electrophysiological methods are further provided.

BACKGROUND OF THE INVENTION

Cyclic AMP (cAMP) is a ubiquitous intracellular second messenger that coordinates diverse cellular functions. It is produced in response to a large variety of extracellular stimuli, including hormones and neurotransmitters. Typically, these agents bind to receptors on the extracellular surface, the receptors activate G-proteins on the intracellular surface and the G-proteins in turn activate adenylyl cyclase, the enzyme that produces cAMP.

cAMP signals are considered to be complex, as evidenced by cAMP's differential regulation of over 200 cellular targets. In addition, the enzymes involved in cAMP metabolism are known to be regulated by numerous other signaling pathways. Unfortunately, as discussed further below, an understanding of cAMP signals has been elusive, due to the fact that current methods for measuring cAMP lack both temporal and spatial resolution. Thus, what is needed are high-resolution means that provided the requisite resolution in order to measure intracellular cAMP.

For example, the standard method for measuring cAMP accumulation within cells is to treat cells with [$^3$H]-adenine to label the ATP pool, and then measure the conversion of [$^3$H]ATP to [$^3$H]cAMP at different time points (See e.g., Evans et al., Mol. Pharmacol., 26:395–404 [1984]). This method is typically done on hundreds of thousands to millions of cells. As a consequence, the method has no spatial resolution and it cannot be used to assess cell-to-cell variability within a population. In addition, it is labor-intensive because cAMP accumulation can be measured only at discrete time points (i.e., in contrast to fluorescence or electrophysiological techniques, it does not provide a continuous readout). This is an important consideration in screening applications. In addition, the method has low temporal resolution, as it is impractical to measure cAMP accumulation in less than 5 second increments. Thus, it is likely that rapid changes in cAMP will be missed when this technique is used.

A second method currently used in the art involves measuring the changes in fluorescence energy transfer between labeled subunits of cAMP-dependent protein kinase, which dissociate upon binding of cAMP. Fluorescent subunits are either prepared biochemically and microinjected (See, Adams et al., Nature 349:694–697 [1991]), or are genetically encoded (See, Zaccolo et al., Nat. Cell. Biol., 2:25–29 [2000]). Although this method does allow for detection of cAMP changes in single cells, it has very low spatial resolution due to limitations in the wavelength utilized (i.e., it is limited by the wavelengths of visible light; 400–800 nm). It also has low temporal resolution, due to the slow reassociation of labeled subunits (i.e., a half-time of 100–200 seconds at typical subunit concentrations; See, Ogreid and Doskeland, Biochem., 22:1686–1696 [1983]), and the tendency of catalytic subunits that catalyze phosphorylation to accumulate in the nucleus (See, Harootunian et al., Mol. Cell. Biol., 4:993–1002 [1993]). In addition, in order to overwhelm endogenous kinase, several micromolar labeled subunits are usually introduced into the test system. This strongly buffers natural cAMP signals, and causes functional alterations of cellular targets due to extensive phosphorylation. Thus, there remains a need in the art for methods and compositions that further elucidate the activities of receptors, G-proteins, phosphodiesterases (PDEs), adenylyl cyclases, and other proteins important in cAMP signalling.

SUMMARY OF THE INVENTION

The present invention provides modified CNG channels, in which the sensitivity and specificity for cAMP are increased. In addition, regulation by $Ca^{2+}$-CaM is removed in the modified CNG channels. Convenient optical methods for detecting changes in cAMP, taking advantage of the $Ca^{2+}$ permeability of the channel are also provided by the present invention.

In particular, the present invention provides isolated nucleic acids encoding a modified olfactory cyclic nucleotide-gated ion channel, wherein the channel comprises mutations which together impart increased cAMP sensitivity, decreased cGMP sensitivity, decreased nitric oxide sensitivity and decreased calcium-calmodulin sensitivity.

The present invention also provides isolated nucleic acids encoding a modified olfactory cyclic nucleotide-gated ion channel, in which the channel comprises at least one mutation selected from the group consisting of a C460W mutation and a E583M mutation. In some embodiments, the channel comprises a E583M mutation; a C460W mutation and a E583M mutation; or a 61-90 deletion, a C460W mutation, and a E583M mutation. In a subset of these embodiments, the channel comprises an amino acid sequence selected from the group consisting of SEQ ID NO:5, SEQ ID NO:6, and SEQ ID NO:7. Also provided in some embodiments are polypeptides encoded by the isolated nucleic acids, and expression vectors comprising the isolated nucleic acids. In preferred embodiments, the vector is a recombinant adenovirus vector. Furthermore, the invention provides host cells comprising the expression vectors, in which the host cell is selected from the group consisting of a prokaryotic cell and a eukaryotic cell. In preferred embodiments, the eukaryotic cell is selected from the group consisting of a human embryonic kidney-293 cell, a GH4C1 pituitary cell, and a rat C6-2B glioma cell.

The present invention also provides methods for determining local intracellular cAMP concentration within an eukaryotic cell, comprising the steps of providing: at least one eukaryotic cell, and a nucleic acid encoding a modified olfactory cyclic nucleotide-gated ion channel, in which the channel comprises at least one mutation selected from the group consisting of a C460W mutation and a E583M mutation; and contacting the eukaryotic cell with the nucleic acid under conditions suitable for expressing the modified olfactory cyclic nucleotide-gated ion channel in the eukaryotic cell; measuring intracellular calcium concentration in the eukaryotic cell; and determining local intracellular cAMP concentration based upon the intracellular calcium concentration. In some embodiments, the contacting step comprises infecting the eukaryotic cell with a recombinant adenovirus comprising the nucleic acid. In some preferred embodiments, the measuring step comprises contacting the eukaryotic cell with a stimulus. In a subset of these embodiments, the stimulus is selected from the group consisting of an adenylate cyclase activator, a G-protein activator, and a phosphodiesterase inhibitor. In particularly preferred embodiments, the measuring step comprises monitoring calcium flux with a fluorescent calcium indicator. Appropriate fluorescent calcium indicators include but are not limited to fura-2, indo-1, quin-2, fluo-3 and rhod-2.

Moreover, the present invention provides methods for determining local intracellular cAMP concentration within an eukaryotic cell, comprising the steps of providing: at least one eukaryotic cell, and a nucleic acid encoding a modified olfactory cyclic nucleotide-gated ion channel, wherein the channel comprises at least one mutation selected from the group consisting of a C460W mutation and a E583M mutation; and contacting the eukaryotic cell with the nucleic acid under conditions suitable for expressing the modified olfactory cyclic nucleotide-gated ion channel in the eukaryotic cell; measuring the electric current across the plasma membrane of the eukaryotic cell; and determining local intracellular cAMP concentration based upon the electric current. In some embodiments, contacting step comprises infecting the eukaryotic cell with a recombinant adenovirus comprising the nucleic acid. In some preferred embodiments, the measuring step comprises contacting the eukaryotic cell with a stimulus. In a subset of these embodiments, the stimulus is selected from the group consisting of an adenylate cyclase activator, a G-protein activator, and a phosphodiesterase inhibitor. In some embodiments, the measuring step comprises monitoring the electric current with a patch-clamp technique selected from the group consisting of perforated patch-clamp technique and a whole-cell patch-clamp technique. In related embodiments, the determining step comprises calibrating the electric current with respect to cAMP concentration by obtaining a cAMP-dose response curve for the modified cyclic nucleotide-gated ion channel with an inside-outside patch clamp technique.

Also provided by the present invention are methods for determining whether a candidate compound is capable of modulating local intracellular cAMP concentration within a eukaryotic cell, comprising the steps of providing: at least one eukaryotic cell expressing a modified olfactory cyclic nucleotide-gated ion channel, wherein the channel comprises at least one mutation selected from the group consisting of a C460W mutation and a E583M mutation, and a drug candidate; and determining local intracellular cAMP concentration within the eukaryotic cell in the presence and absence of the drug candidate. In some embodiments, the expressing of the modified olfactory cyclic nucleotide-gated ion channel is accomplished by infection of the eukaryotic cell with a recombinant adenovirus. In some preferred embodiments, the determining of the local intracellular cAMP concentration is accomplished by measuring intracellular calcium concentration in the eukaryotic cell in the presence and absence of the drug candidate. In other preferred embodiments, the determining of the local intracellular cAMP concentration is accomplished by measuring the electric current the plasma membrane of the eukaryotic cell in the presence and absence of the drug candidate.

DESCRIPTION OF THE FIGURES

FIG. 1 provides the nucleotide sequence of a modified rat olfactory cyclic nucleotide-gated ion channel containing the E583M mutation (SEQ ID NO:1). The corresponding amino acid sequence is disclosed as SEQ ID NO:5.

FIG. 2 provides the nucleotide sequence of a modified rat olfactory cyclic nucleotide-gated ion channel containing the C460W/E583M mutation (SEQ ID NO:2). The corresponding amino acid sequence is disclosed as SEQ ID NO:6.

FIG. 3 provides the nucleotide sequence of a modified rat olfactory cyclic nucleotide-gated ion channel containing the Δ61-90/C460W/E583M mutation (SEQ ID NO:3). The corresponding amino acid sequence is disclosed as SEQ ID NO:7.

FIG. 4 provides the nucleotide sequence of the wild-type rat olfactory cyclic nucleotide gated channel (SEQ ID NO:4), GenBank Accession No. NM 012928. The corresponding amino acid sequence is disclosed as SEQ ID NO:8.

Panel D provides a graph showing forskolin-induced responses in cells expressing the Δ61-90/C460W/E583M channel, saturating at 20 μM. For each construct, the variability in the response between batches of cells was <25% (n=4).

Figure 7:
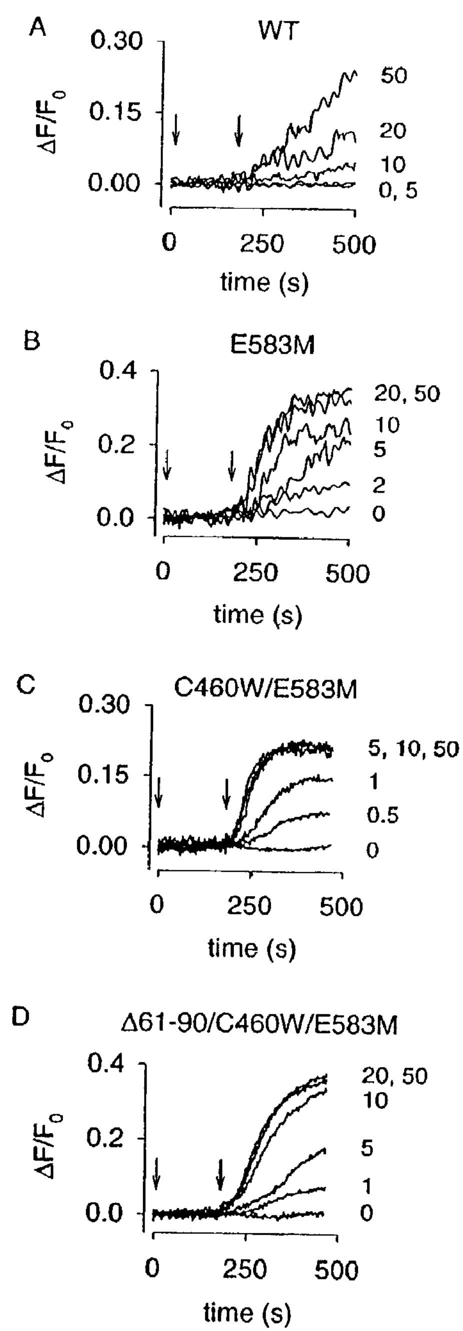
FIG. 7 provides data showing forskolin-induced cAMP accumulation in HEK-293 cells monitored using $Ca^{2+}$ influx through expressed CNG channels. In these experiments, 100 μM IBMX was added at time zero and different forskolin concentrations were added at 180 s (indicated by the arrows); concentrations (in micromolar) are indicated at the end of each trace. Panel A provides a graph showing the forskolin-induced $Ca^{2+}$ influx was observed in cells expressing the WT channel; the cAMP response (slope) did not saturate in the forskolin range tested (0–50 μM). Panel B provides a graph showing that the forskolin-induced $Ca^{2+}$ influx was larger in cells expressing the E583M channel than WT channel (Panel A). More importantly, the responses saturated at 20 μM. Panel C provides a graph showing that the forskolin-induced responses in cells expressing the C460W/E583M channels saturated at a lower forskolin concentration than the E583M channels (Panel B), at 5 μM.
Figure 8:
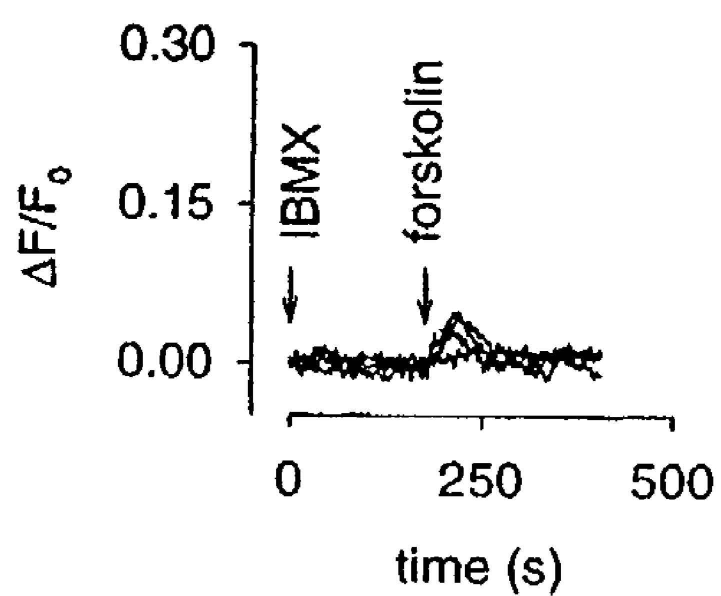

FIG. 8 provides a graph showing the typical forskolin-induced $Ca^{2+}$ influx in control HEK-293 cells. HEK-293 cells not expressing CNG channel constructs were treated in the same manner as those described above for FIG. 7. Forskolin (0, 0.5, 5 or 50 μM) was added 180 s after treatment with 100 μM IBMX. As indicated, little or no $Ca^{2+}$ influx was observed in control HEK-293 cells under any of the experimental conditions described herein.

Figure 9:
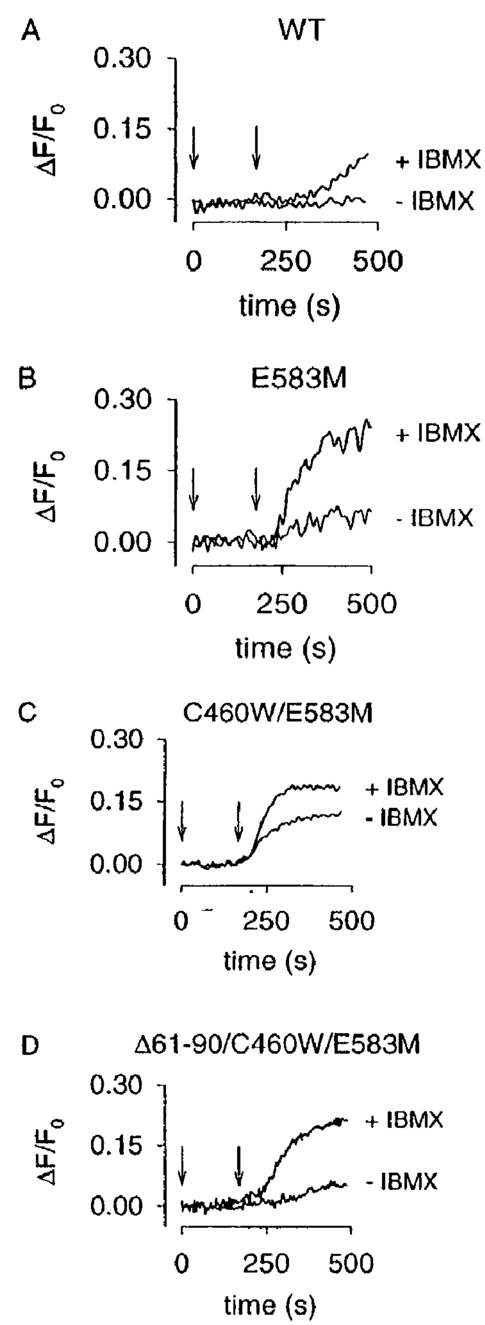

FIG. 9 provides data showing that PDE activity reduces forskolin-induced $Ca^{2+}$ influx through CNG channels in HEK-293 cells. $Ca^{2+}$ influx through WT (Panel A), E583M (Panel B), C460W/E583M (Panel C), and Δ61-90/C460W/E583M (Panel D) CNG channels in response to 10 μM forskolin (180 s, indicated by arrows), after a 3 minute pre-treatment with either vehicle (-IBMX) or 100 μM IBMX. Note that a robust forskolin-induced response was easily monitored in the absence of IBMX using C460W/E583M channels as cAMP sensors (Panel C).

Figure 10:
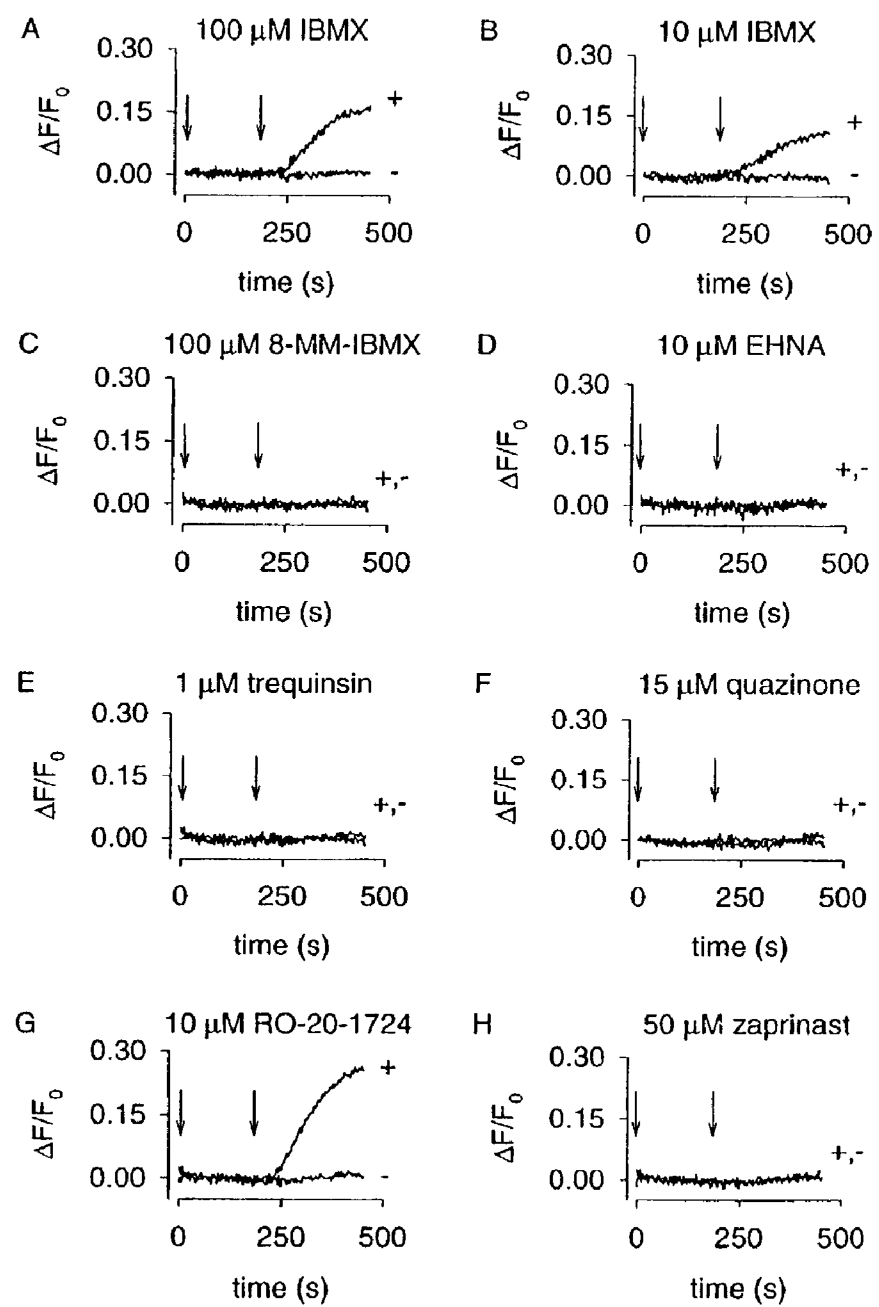

FIG. 10 provides data showing the effects of different PDE inhibitors on forskolin-induced $Ca^{2+}$ influx in HEK-293 cells. C460W/E583M channels were used to monitor cAMP accumulation in the presence and absence of PDE inhibitors: A) 100 μM IBMX; B) 10 μM IBMX; C) 100 μM 8-MM-IBMX; D) 10 μM EHNA; E) 1 μM trequinsin; F) 15 μM quazinone; G) 10 μM RO-20-1724; and H) 50 μM zaprinast. PDE inhibitors were added at time zero, and 1 μM forskolin was added at 180 s (indicated by arrows). The $IC_{50}$ for each PDE inhibitor is provided in Table 3. As indicated in this Figure, only the non-specific PDE inhibitor IBMX (Panels A and B) and the PDE type IV-specific inhibitor RO-20-1724 (Panel G) influenced the time course of forskolin-induced $Ca^{2+}$ influx. In general, there was little variability in responses within a single batch of cells.

Figure 11:
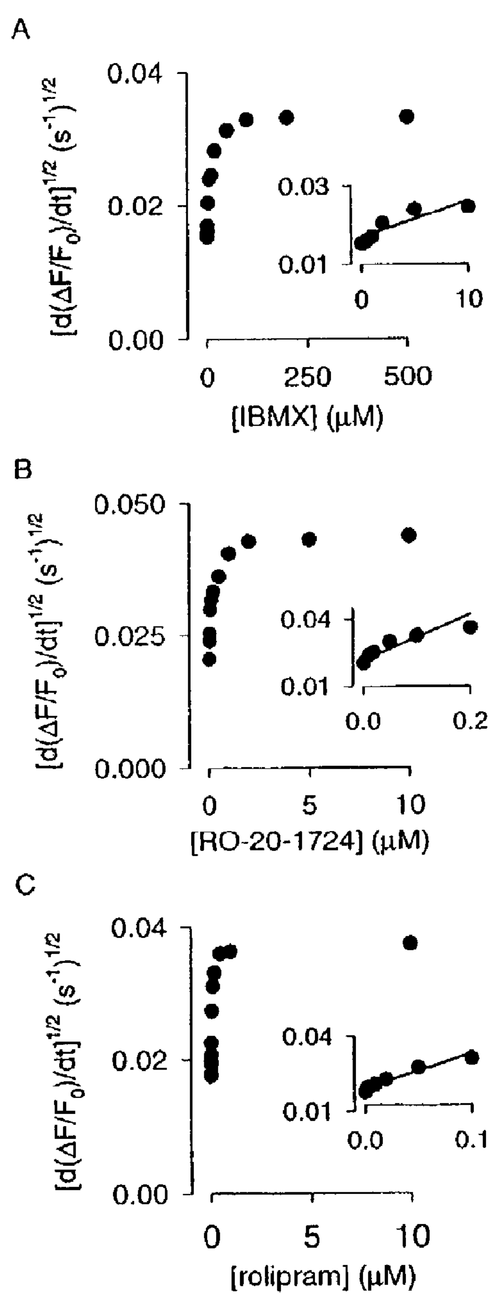

FIG. 11 provides data showing estimates of $K_I$ for three different PDE inhibitors. As indicated, the results reveal that PDE type IV regulates local cAMP levels in HEK-293 cells. C460W/E583M channels were used to monitor cAMP accumulation triggered by 0.5 μM forskolin (180 s) in the presence and absence of PDE inhibitors (0 s). The $d(\Delta F/F_0)/dt$ values were determined as described below for FIG. 12. The linear fits used to estimate $K_I$ values are shown in the insets. The $K_I$s of the PDE inhibitors were 10 μM (IBMX; Panel A), 0.14 μM (RO-20-1724; Panel B), and 0.09 μM (rolipram; Panel C) for the experiments shown.

Figure 12:
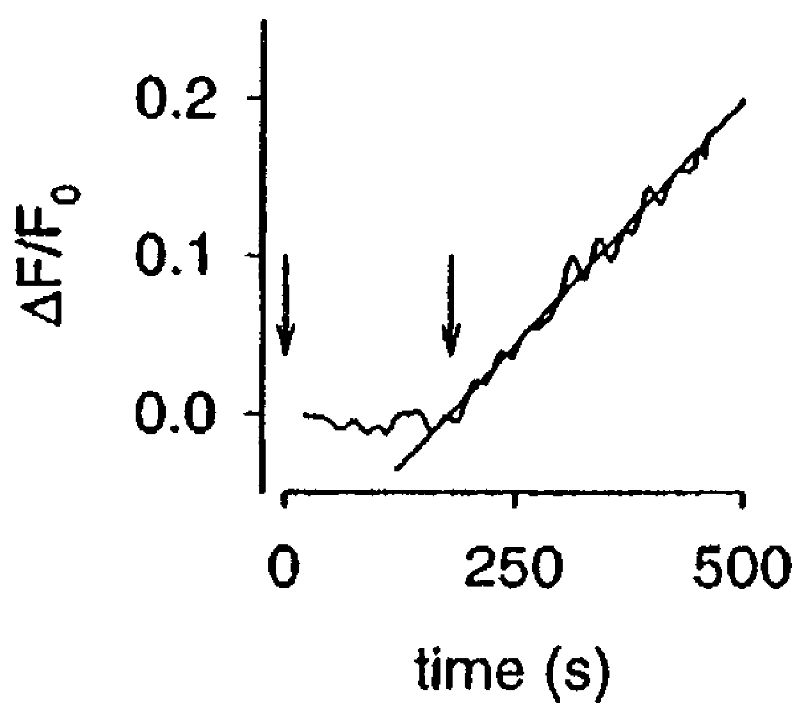

FIG. 12 provides a graph showing the measurement of $Ca^{2+}$ through CNG channels in response to a rise in cAMP. $Ca^{2+}$ influx caused a decrease in fluorescence (ΔF), which was expressed relative to the pre-stimulus fluorescence ($F_0$). In these experiments, HEK-293 cells expressing C460W/E583M CNG channels responded to increased cAMP levels caused by exposure to 50 nM rolipram added at 0 s (first arrow) and 0.5 μM forskolin added at 180 s (second arrow). After a brief lag, ΔF changed in a linear fashion (slope=$6.2\times10^{-4}s^{-1}$). Slopes were used to assess relative $Ca^{2+}$ influx rates, for estimating the $K_I$ of PDE inhibitors (See, Eqs. 4 and 5).

Figure 13:
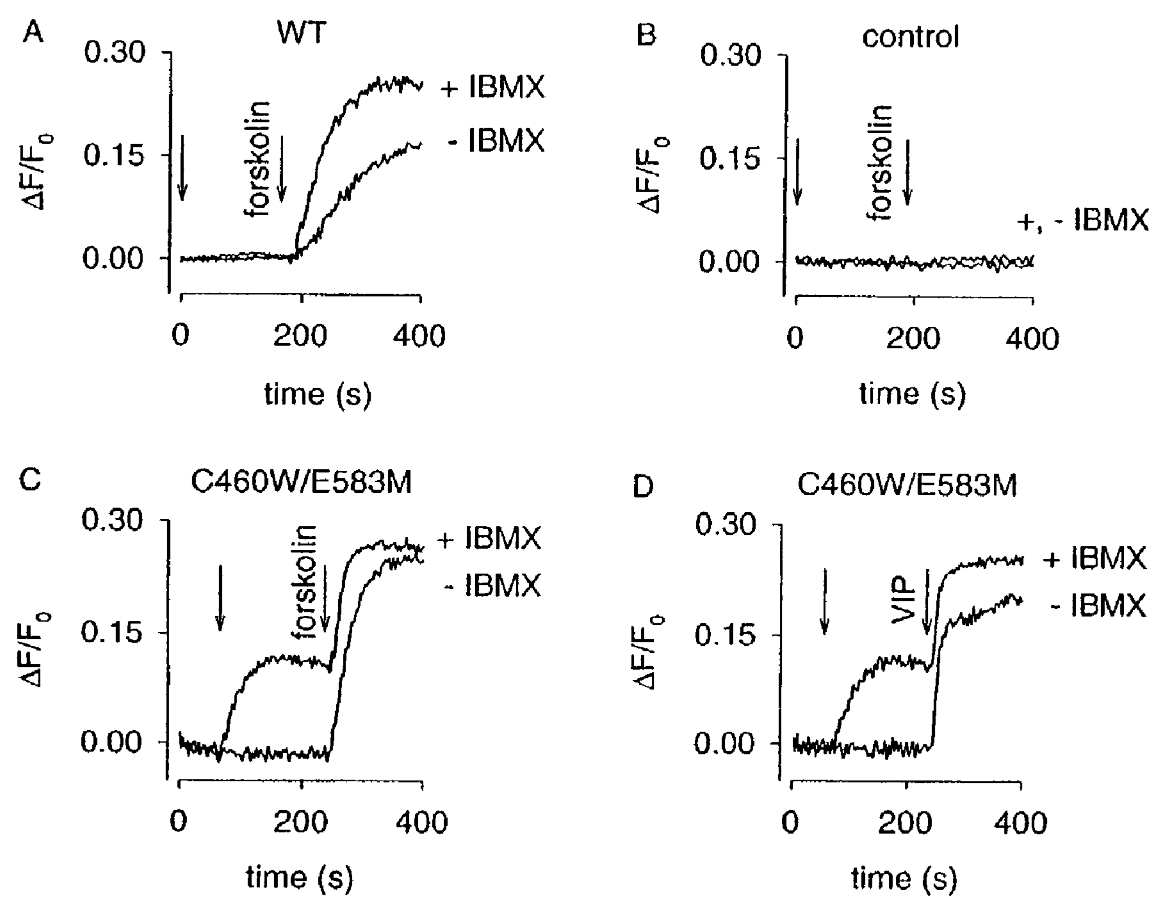

FIG. 13 provides data showing detection of AC and PDE activity in GH4C1 cells. Panel (A) provides data for GH4C1 cells expressing WT CNG channels. Either 100 μM IBMX or vehicle (-IBMX; control) were added at time zero. Then, 50 μM forskolin was added at 180 s. Panel B provides data for control cells (i.e., cells not expressing CNG channels). No forskolin-induced $Ca^{2+}$ influx was observed under these conditions, or any of the experimental conditions presented. Panels C and D provide results for GH4C1 cells expressing C460W/E583M channels. IBMX or vehicle (-IBMX; control) was added at 60 s (first arrow). Either 10 μM forskolin (Panel C) or 100 nM VIP (Panel D) were added at 240 s (second arrow). In the absence of IBMX, large forskolin- or VIP-induced increases in $Ca^{2+}$ influx were observed. When the local PDE activity was inhibited by 100 μM IBMX, substantial basal AC activity was revealed. This level of basal AC activity was quite different from that observed in HEK-293 cells (See, FIGS. 9 and 10). In these experiments, 1 μM nimodipine was added at time 0 to block endogenous voltage-gated $Ca^{2+}$ channels.

Figure 14:
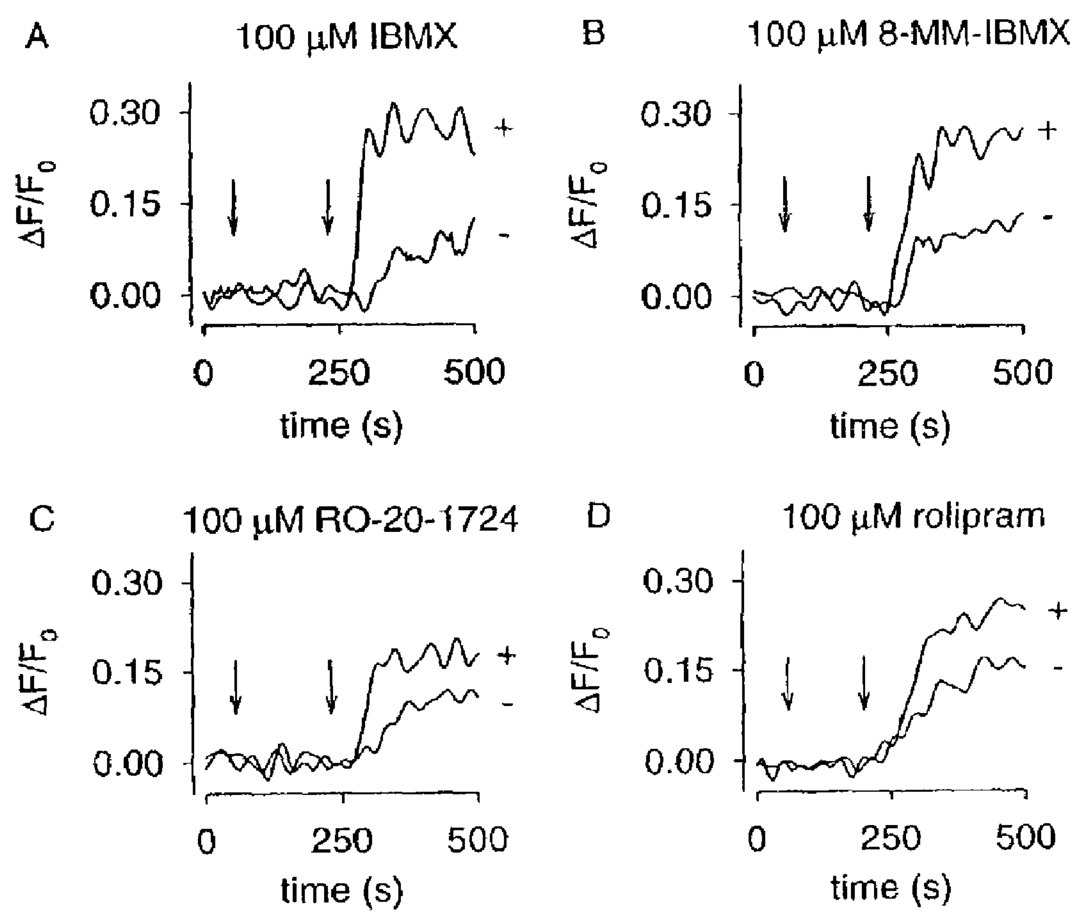

FIG. 14 provides data showing that PDE type IV is responsible for localized, high $K_m$ PDE activity in GH4C1 cells. In these experiments, Δ61-90/C460W/E583M channels were used to detect changes in cAMP accumulation in the presence and absence of PDE inhibitors. Inhibitors were added at 60 s, 10 μM forskolin was added at 240 s, and 1 μM nimodipine was added at time zero (to block voltage-gated $Ca^{2+}$ channels). As indicated, the non-specific PDE inhibitor IBMX (Panel A), the PDE type 1-specific inhibitor 8-methoxymethyl-IBMX (8-MM-IBMX) (Panel B), the PDE type IV-specific inhibitors RO-20-1724 (Panel C), and rolipram (Panel D) were shown to increase forskolin-induced $Ca^{2+}$ influx through CNG channels.

Figure 15:
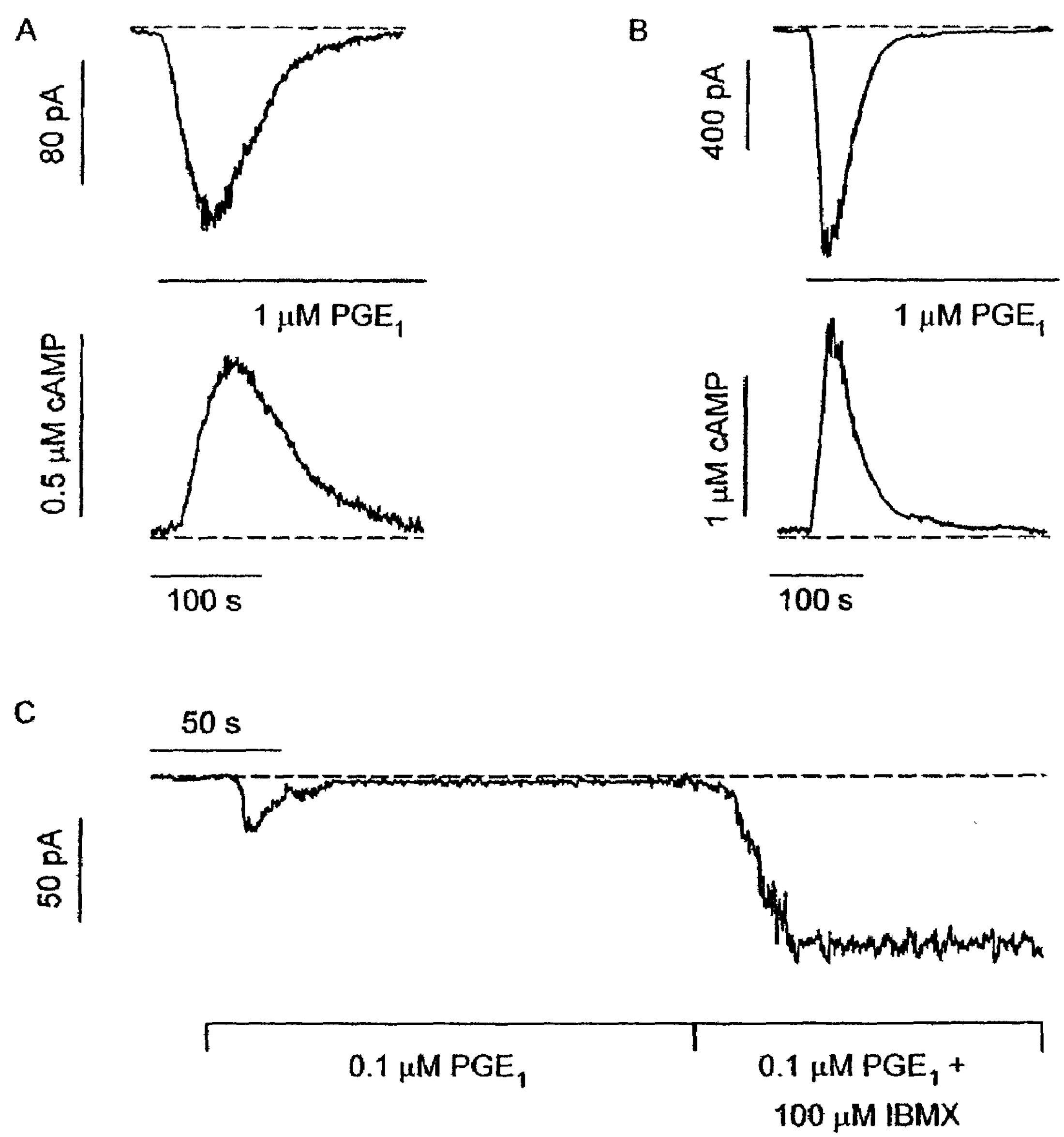

FIG. 15 provides results from experiments to determine single-cell measurements of local cAMP signals. Upper portions of Panels A and B show that rapid application of $PGE_1$ triggered transient inward currents through CNG channels (−20 mV). Two different cells were monitored in perforated patch configuration. The lower portions of Panels A and B the corresponding cAMP signals calibrated as described herein. Panel C provides results showing that rapid application of $PGE_1$ triggered a transient inward current (whole cell configuration, −20 mV). Subsequent application of $PGE_1$ and IBMX triggered an inward current that rose to a plateau. This current was blocked by 10 mM $MgCl_2$ (characteristic of CNG channels). Dashed lines indicate either zero cyclic nucleotide-induced current (the current in 10 mM $MgCl_2$) or zero cAMP. No $PGE_1$-induced currents were observed in cells not expressing CNG channels. Several additional controls were done to ensure that the $PGE_1$-induced signal was due to a rise and fall in cAMP. $PGE_1$ had no direct effect on channels in excised membrane patches, and when it was applied to cells it did not affect the cAMP sensitivity, the conductance, nor the number of active channels. In addition, treatment of CNG-channel-expressing cells with $PGE_1$ triggered little or no release of $Ca^{2+}$ from internal stores and no measurable increases in cGMP, as shown in FIGS. 18 and 19.

Figure 16:
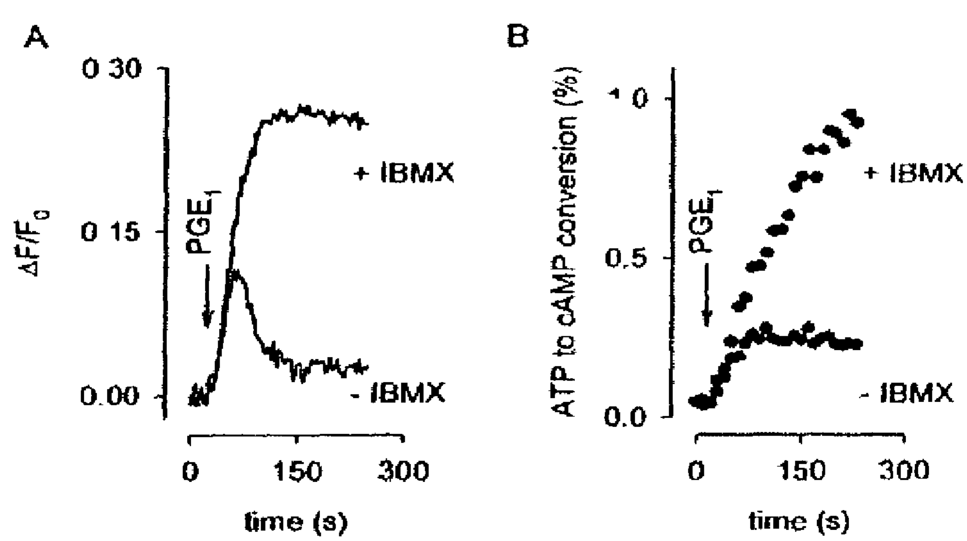

FIG. 16 provides a comparison of membrane-localized (A) and total cAMP (B) levels in cell populations. In Panel A, shows that sustained application of 10 μM $PGE_1$ in the absence of PDE inhibitor caused an increase in $Ca^{2+}$ influx, followed by a decline in $Ca^{2+}$. Little or no increase in $Ca^{2+}$ was observed in cells not expressing the channel. The initial interpretation was that $PGE_1$ triggered a rise and fall in local cAMP concentration: the rise caused an increase in $Ca^{2+}$ influx through CNG channels; the subsequent fall in cAMP led to reduced $Ca^{2+}$ influx; and, $Ca^{2+}$ pumping mechanisms caused the decline in $Ca^{2+}$ levels. In support of this interpretation, $PGE_1$ in the presence of the PDE inhibitor IBMX caused $Ca^{2+}$ to rise along a similar time-course, but the decay phase was abolished. These results indicate that the underlying cause of the decay phase was hydrolysis of cAMP. In populations of cells expressing C460W/E583M channels, $PGE_1$ caused total cellular cAMP accumulation, assessed as the conversion of [$^3$H]ATP to [$^3$H]cAMP, to rise to a plateau in the absence of IBMX (See, FIG. 16, Panel B). This is in marked contrast to the transient increase in cAMP inferred from FIG. 16, Panel A.

Figure 17:
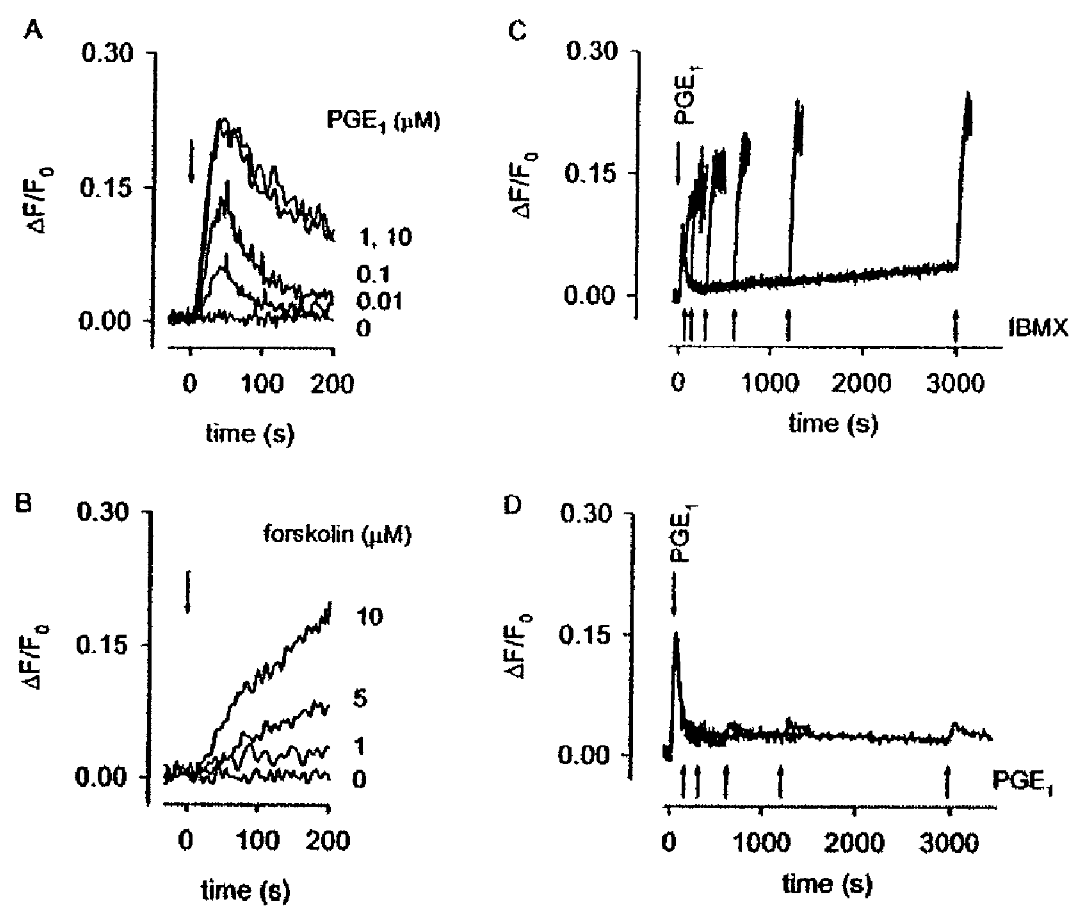

FIG. 17 provides results showing that $PGE_1$ triggers sustained AC and PDE activity. Panels A and B show local cAMP changes in response to AC stimulation, monitored by $Ca^{2+}$ influx through C460W/E583M channels. $PGE_1$ (Panel A) or forskolin (Panel B) were applied at the indicated concentrations. Panel C shows rises in cAMP (monitored by $Ca^{2+}$ influx) caused by 100 nM $PGE_1$ (t=0) and subsequent addition of 100 μM IBMX (1, 2, 5, 10, 20, or 50 min; superimposed traces). The slopes of the IBMX-induced responses (0.0044±0.0008 $s^{-1}$) were similar to each other and to the slopes of the initial $PGE_1$-induced responses (0.0038±0.0003 $s^{-1}$). IBMX and RO-20-1724 had no effect on channel activity in excised membrane patches (Rich et al. [2001], supra). Panel D provides results showing that the second additions of 100 nM $PGE_1$ (2, 5, 10, 20, or 50 min; superimposed traces) following the initial addition of 100 nM $PGE_1$ (t=0) gave little or no response.

Figure 18:
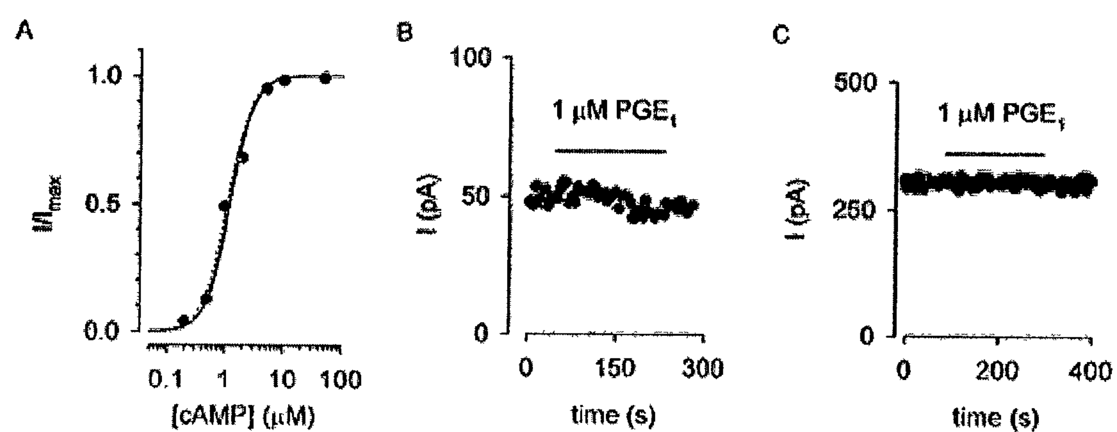
Figure 19:
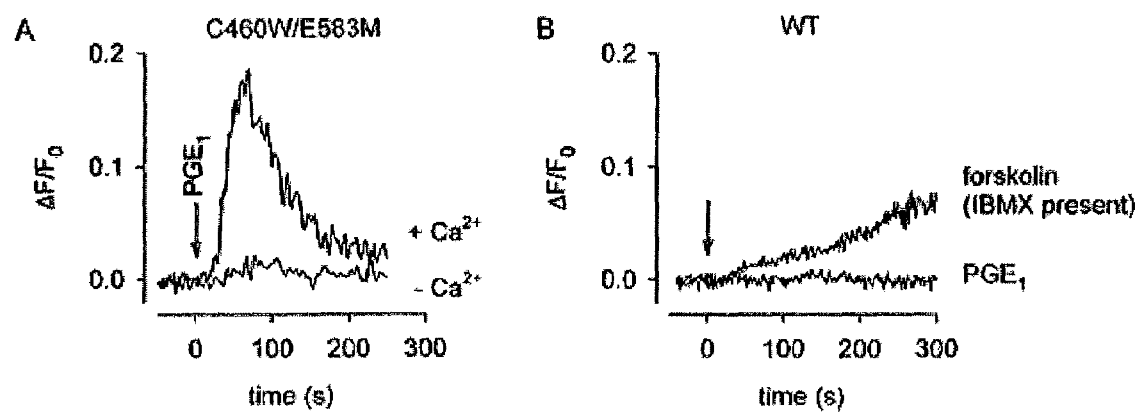

FIG. 18 provides data showing that $PGE_1$ treatment of HEK-293 cells does not alter CNG channel properties. To ensure that $PGE_1$ was not altering the number of channels, conductance, or cAMP sensitivity, several control experiments were performed on cells expressing C460W/E583M channels. Panel A provides results indicating a typical cAMP dose-response relation in an excised membrane patch, from a cell that was treated with 1 μM $PGE_1$ for >5 min prior to patch excision (circles). Patches were excised directly into a solution containing 1 μM cAMP (a subsaturating concentration). Currents were monitored for >30 min after patch excision, and no change in channel activity was observed. There was no significant difference in cAMP sensitivity between patches excised from cells pretreated with $PGE_1$ ($K_{1/2}$=1.2 μM, solid line) and those excised from control cells (i.e., cells not pretreated with $PGE_1$; $K_{1/2}$=1.1 μM, dotted line). To test whether $PGE_1$ directly modulated channel properties, excised, inside out patches were exposed to $PGE_1$. A typical example is shown in Panel B. A patch exposed to 1 μM cAMP was treated for the indicated period with 1 μM $PGE_1$; no change in current was observed (+50 mV). Panel C provides results from experiments to determine whether $PGE_1$ could alter the number of active channels. In these experiments, currents were monitored in the whole cell configuration (+50 mV) with 100 μM 8-(p-chlorophenylthio)-cGMP (a saturating concentration of a hydrolysis-resistant cGMP analog) in the patch pipette. In order to ensure that the nucleotide had equilibrated throughout the cell, there was a waiting period of more than 10 min after break-in to ensure that the nucleotide had equilibrated throughout the cell. Currents were unaffected by extracellular application of 1 μM $PGE_1$. The leak current was determined by blocking the channels with 10 mM $MgCl_2$.

FIG. 19 provides results showing that $PGE_1$ does not trigger significant $Ca^{2+}$ release from internal stores nor production of membrane localized cGMP, in HEK-293 cells expressing CNG channels. Changes in internal $Ca^{2+}$ were monitored using fura-2 as described herein. Panel A provides results for cells expressing C460W/E583M CNG channels that were resuspended in nominally $Ca^{2+}$ free solution ($-Ca^{2+}$ trace) one minute prior to the addition of 100 mM $PGE_1$ (arrow). $PGE_1$ caused little or no rise in $Ca^{2+}$, indicating negligible release from internal stores. As a positive control for CNG channel expression, the experiment was repeated in the presence of 1 mM $Ca^{2+}$ using an aliquot from the same batch of cells ($+Ca^{2+}$ trace) a large transient $Ca^{2+}$ influx through CNG channels was observed. Panel B provides results showing that cGMP did not contribute to the observed transient responses in experiments which monitored $Ca^{2+}$ influx (1 mM external $Ca^{2+}$) through wild-type (WT) olfactory CNG channels (which have a significantly higher sensitivity to cGMP and a significantly lower sensitivity to cAMP than C460W/E583M channels (Rich et al. [2001] supra). After the addition of 100 nM $PGE_1$ there was no observable $Ca^{2+}$ influx. This demonstrates that cGMP made no contribution to the $PGE_1$-induced responses measured with the high-cAMP-affinity C460W/E583M channels. As a positive control for WT CNG channel expression, (100 μM) forskolin-induced $Ca^{2+}$ influx was monitored following a 3-min pretreatment with 100 μM IBMX.

DESCRIPTION OF THE INVENTION

The present invention provides modified cyclic nucleotide gated (CNG) channels. In particularly preferred embodiments, the modified CNG channels exhibit increased sensitivity and specificity for cAMP, as compared to wild-type CNG channels. In additional embodiments, regulation by $Ca^{2+}$-calmodulin has been removed in the modified CNG channels. Convenient optical methods for detecting changes in cAMP, taking advantage of the $Ca^{2+}$ permeability of the channel are also provided by the present invention. In addition, electrophysiological methods are further provided.

In some preferred embodiments, the present invention provides genetically-modified cyclic nucleotide-gated ion channels. This class of channels is directly opened by the binding of cyclic nucleotides. These channels were discovered in retinal photoreceptor cells and olfactory receptor neurons, where they generate the electrical response to light and odorants. The native retinal channel is cyclic GMP (cGMP) specific, while the native olfactory channel is equally sensitive to cAMP and cGMP. Native channels consist of both and subunits, both of which bind cyclic nucleotides. Open channels allow cations ($Na^+$, $K^+$, $Ca^{2+}$, $Mg^{2+}$) to pass through the cell membrane. Thus, the activation of channels is readily detected with both electrophysiological and $Ca^{2+}$-imaging techniques, as known in the art.

As discussed in greater detail herein, cyclic nucleotide-gated (CNG) channels have several properties that make them attractive as cAMP sensors. First, they incorporate into discrete regions of the surface membrane where adenylyl cyclase is known to reside. Second, several hundred channels in a cell give a robust signal without significantly buffering the cAMP being measured. Third, cyclic nucleotide-gated channels respond rapidly to changes in cyclic nucleotide concentration. Fourth, the sensor can be calibrated in different cell types by measuring the apparent cAMP affinity in excised membrane patches. This controls for the possible modulation of CNG channels by endogenous proteins.

Retinal and olfactory α subunits form functional channels on their own, and the rat olfactory α subunit was previously used to measure cAMP accumulation under strong stimulus conditions. However, the wild-type α subunit has several drawbacks for measuring physiologic cAMP signals. First, wild-type channels (See, FIG. 4, and SEQ ID NO:4) have a low apparent affinity for cAMP, which makes it difficult to detect the low cAMP concentrations that activate protein kinase A (PKA), a crucial effector of cAMP signals. Second, these channels are much more sensitive to cGMP than cAMP. The $K_{1/2}$ values (i.e., the concentrations that half-maximally activate the channel) are 1.6 and 36 μM, respectively (See, Table 1, below). Third, they can also be activated directly by nitric oxide. Fourth, the binding of the $Ca^{2+}$-calmodulin ($Ca^{2+}$-CaM) complex to these channels strongly inhibits channel opening. To overcome these limitations, the present invention provides novel CNG channels with improved cAMP-sensing capabilities.

In some embodiments of the present invention, a mutant rat olfactory channel α subunit is used. In order to create the mutant, modifications were made to the rat olfactory channel α subunit to increase its sensitivity and specificity for cAMP and to remove regulation by $Ca^{2+}$-CaM. In particular, new mutations, designated as "C460W" and "E583M" were used to produce a channel with significantly increased sensitivity and specificity for cAMP. The resultant C460W/E583M channel has $K_{1/2}$ values of 1.2 and 12 μM for cAMP and cGMP (See, Table 1, below). To remove regulation of the channel by $Ca^{2+}$-CaM binding residues 61 through 90 were deleted.

The Δ61-90/C460W/E583M channel has two important advantages. First, it is virtually insensitive to cGMP. The current elicited by a saturating concentration of cGMP is 16% of the current elicited by saturating cAMP (See, Table 1, below). In addition, 36 μM cGMP is required to elicit half of that tiny response. Second, the channel is not inhibited by $Ca^{2+}$-CaM. The sensitivity to cAMP is reduced ($K_{1/2}$=14.5 μM), which allows cAMP to be measured in the upper end of the physiologic range. The use of both mutant channels allows cAMP to be measured over the entire physiologic range (0.1 to 50 μM).

As described in greater detail herein, the effects of modifications to CNG channels were assessed using the Hill equation, $I/I_{max}=[cNMP]^N/([cNMP]^N+K_{1/2}{}^N)$, where $I/I_{max}$ is the fraction of maximal current, cNMP represents cyclic nucleotide, $K_{1/2}$ is the concentration that gives half-maximal current, and N is the Hill coefficient, an index of cooperativity. $I'_{max}{}^{cGMP}/I_{max}{}^{cAMP}$ is the current induced by saturating cGMP divided by the current induced by saturating cAMP. Data (mean±standard deviation of three experiments) were obtained from excised membrane patches using standard patch clamp techniques.

In particularly preferred embodiments, the coding sequence of the channels have been incorporated into adenovirus constructs, which allow for efficient expression in a variety of cell types. The adenovirus constructs of preferred embodiments of the present invention are deleted for the E3 region and have the E1 region replaced by the CNG channel alleles under the control of the cytomegalovirus major intermediate promoter. The channels have been used to measure cAMP in two different assay designs.

One assay system involves a convenient, optical method for detecting changes in cAMP, which takes advantage of the $Ca^{2+}$ permeability of the channel. There are several advantages of measuring $Ca^{2+}$ influx through CNG channels as a way to monitor changes in cAMP. Importantly, this assay is very simple to implement in either cell populations or single cells. In addition, the measurement has a high signal-to-noise ratio. Furthermore, it is sensitive to small changes in adenylyl cyclase activity. In contrast to the present invention, in traditional assays, strong stimuli and phosphodiesterase (PDE) inhibitors are often required to detect cAMP accumulation. Natural cAMP signals are severely distorted by the necessity to inhibit PDE, the enzyme responsible for degrading cAMP. In contrast to the currently used means, the novel channels described herein readily detect changes in cAMP in response to physiologic stimuli, and in the absence of PDE inhibitors. This assay is particularly well-suited as an initial screen for changes in cAMP.

Another assay system that finds use with the present invention involves the use of electrophysiological assays, in which either perforated patch or whole-cell configurations of the patch clamp technique are used to measure currents through the ion channels. This assay is particularly appropriate when more precise measurements of local cAMP are required. These measurements take advantage of the fast response of CNG channels to changes in cAMP concentration, without the distortions that arise from the $Ca^{2+}$ handling properties of the cell. The higher dynamic range, increased temporal resolution, and more accurate measurement of cAMP concentration provided by these methods find use in providing information regarding cAMP signals and signalling systems. The increased sensitivity of the novel CNG channels of the present invention were confirmed using in vivo assays by monitoring cAMP-induced $Ca^{2+}$ influx through the channels in cell populations and by measuring cAMP-induced currents in the whole-cell patch clamp configuration.

Further, as discussed herein, the present invention provides methods and compositions for measuring changes in intracellular cAMP. A very large number of natural agents (e.g., hormones, neurotransmitters, odorants) and drugs bind to G-protein coupled receptors and cause changes in cAMP levels. As the present invention provides a system with demonstrated robust expression of the adenovirus-encoded sensor in several cell types, the present invention provides means for both high-throughput pharmacological screens as well as for many research purposes.

Indeed, the compositions of the present invention have been used: 1) to demonstrate the existence of distinct cAMP signals in different regions of a simple cell; 2) to probe the interplay between stimulatory and inhibitory G-protein regulation of adenylyl cyclase; 3) to identify the phosphodiesterase (PDE) subtypes that shape cAMP levels in non-excitable and excitable cells (these experiments also provided the inhibition constants of several PDE inhibitors in the intact cell). The present invention provides sensors that have a high signal-to-noise ratio over most of the physiologic range of cAMP concentrations (100 nM to 100 μM). However, it is contemplated that additional sensors of the present invention will find use over the entire range of physiological cAMP concentrations (i.e., down to 20 nM).

As discussed in greater detail elsewhere herein, in some particularly preferred embodiments, the present invention provides compositions comprising several modifications to the WT olfactory CNG channel that significantly enhance its utility as a cAMP sensor. Testing of three novel constructs is described herein. As discussed in greater detail herein, in comparison with WT CNG channels, the E583M channel (SEQ ID NO:5) is more sensitive to cAMP and less sensitive to cGMP. However, two additional mutations produced channels that make even better cAMP sensors. The C460W/E583M channel (SEQ ID NO:6) has a high affinity for cAMP, allowing it to detect cAMP at levels which activate PKA. The Δ61-90/C460W/E583M channel (SEQ ID NO:7) is almost as sensitive to cAMP as the E583M channel. However, the Δ61-90/C460W/E583M channel has two important advantages: it is not inhibited by $Ca^{2+}$-CaM, and it is barely activated by cGMP. Thus, the mutant CNG channels provided by the present invention provide the first ion channels that have been tailored for measurement of cAMP.

The present invention also provides convenient assay systems for detecting changes in local cAMP concentrations and examining PDE activities. PDEs, the crucial terminators of cAMP and cGMP signals, were discovered almost 40 years ago (Drummond and Perrot-Yee, J. Biol. Chem., 236:1126–1129 [1961]). Since then, PDEs have been classified into eleven families according to substrate specificity, regulation, pharmacology, and more recently, amino acid homology (Beavo, Adv. Second Messenger Phosphoprot. Res., 22:1–38 [1988]; Beavo, Physiol. Rev., 75:725–748 [1995]; Conti et al., Endocrine Res., 16:370–389 [1995]). Studies have confirmed differential regulation of PDE families by $Ca^{2+}$-calmodulin ($Ca^{2+}$-CaM), G-proteins, phosphorylation, and cyclic nucleotides. The diversity of PDE families has led to the realization that PDE activity is a central element in the control of second messenger signaling, as important as adenylyl and guanylyl cyclase activity in shaping cyclic nucleotide signals. Yet, little is known about how PDE regulates cyclic nucleotide signals in vivo or how cyclic nucleotide signals differentially regulate hundreds of cellular targets because, outside of specialized cells, there are few convenient real-time measures of cyclic nucleotide concentration. However, the present invention provides the means to address these questions and obtain real-time measurements of cyclic nucleotide concentrations.

In some particularly preferred embodiments, both WT and modified CNG channels are used. There are several advantages provided by the methods and compositions of the present invention involving measuring $Ca^{2+}$ influx through CNG channels as a way to monitor changes in cAMP. First, this assay is very simple to implement in either cell populations or single cells. Second, the measurement has a high signal-to-noise ratio. Third, it is sensitive to small changes in AC activity. This is due, in part, to the fact that CNG channels detect local rather than total cellular cAMP. With traditional assays, high agonist and PDE inhibitor concentrations are often required to detect cAMP accumulation. In contrast, the channels provided by the present invention readily detect changes in cAMP caused by subsaturating agonist concentration in the absence of PDE inhibitors. In addition to being easy to use, the present invention provides improved spatial and temporal resolution, as well as means for calibration to provide precise measures of cAMP concentrations. Thus, among other utilities, the assay systems presented herein find use as initial screens for changes in cAMP in response to physiological stimuli and/or pharmacological agents.

The present invention provides significant improvements in assay systems. However, in some cases, it is difficult to extract the precise cAMP concentration from these assay systems because the responses cannot be calibrated (i.e., with known intracellular cAMP), and because $Ca^{2+}$ handling and depletion of free fura-2 become issues at high $Ca^{2+}$ influx rates. Nonetheless, any of these limitations can be overcome when more precise measurements of local cAMP are required, by determining the cAMP concentration using electrophysiological methods as known in the art (Rich et al. [2000], supra).

During the development of the present invention, observations were made using HEK-293 and C6-2B glioma cells, as well as GH4C1, that CNG channels measure cAMP produced in subcellular compartments or microdomains near the plasma membrane, and that diffusion of cAMP between the microdomains and the bulk cytosol is severely hindered (See, Rich et al. [2000], supra). This conclusion was based on several lines of evidence. First, forskolin-induced increases in cAMP concentration measured using CNG channels (>25 μM) were much greater than the increases in cAMP concentration averaged throughout the accessible cell volume (1–2 μM). Second, forskolin-induced cAMP accumulation was easily detected by CNG channels in the rapidly-dialyzed, whole-cell patch clamp configuration. Third, the wash-in of cAMP from the patch pipette to the CNG channels was much slower than would be expected based upon the rapid exchange of the bulk cytosol. All of these results were described by a three-compartment model (microdomain, cytosol, whole-cell pipette) in which the transfer rates between compartments were determined using data from the wash-in experiments.

During the development of the present invention, much was learned about the two dimensional localization of proteins involved in cellular signaling. For example, certain isoforms of PDE are differentially distributed between particulate (membrane-localized) and supernatant (cytosolic) cellular fractions. In addition, PDE kinetics may vary with cellular localization (See, Bolger et al., Biochem. J., 328: 539–548 [1997]). Elements of G-protein signaling pathways have been shown to preferentially localize within caveolae (i.e., distinct regions of the plasma membrane; See e.g., Rybin et al., J. Biol. Chem., 275:41447–41457 [2000]). Furthermore, a recent report has described the localization of different voltage-gated $K^+$ channels to distinct populations of lipid rafts (Martens et al., J. Biol. Chem., 276:8409–8414 [2001]).

However, two dimensional localization within the plasma membrane does not account for the three dimensional compartmentalization of cAMP signals. Data obtained during the development of the present invention show that proximity to AC does not provide sufficient cAMP concentrations for activation of effector proteins because, in essence, each cAMP molecule diffuses away more rapidly than the next molecule is synthesized. Thus, PDE activity alone is unlikely to be responsible for compartmentalized cAMP signals, because PDE activity only lowers cAMP levels. Thus, it is contemplated that PDEs regulating cAMP levels detected by CNG channels are localized within the same three dimensional compartment as AC and CNG channels. Importantly, by regulating cAMP concentration within this compartment, PDE activity affects the rate of cAMP flux between compartments. This PDE is contemplated to be a component of the particulate PDE fractions. In addition, cytosolic PDE is contemplated to regulate cAMP in other cellular compartments.

During the development of the present invention, $Ca^{2+}$ influx through CNG channels was used to detect changes in cAMP concentration in both nonexcitable HEK-293 cells and excitable pituitary GH4C1 cells. One goal was to assess the PDE subtypes responsible for shaping cAMP signals near the plasma membrane. In order to study the effects of PDEs, it is important to be able to first detect cAMP changes in the absence of PDE inhibitors. There was no difficulty with this in either cell type, despite the modest levels of cAMP accumulation in response to forskolin or VIP stimulation reported previously (Mollard et al., Biochem. J., 284:637–640 [1992]; Fagan et al., J. Biol. Chem., 271: 12438–12444 [1996]; and Fagan et al., J. Biol. Chem., 275:40187–40194 [2000]). In HEK-293 cells, only nonselective and PDE-type-IV selective inhibitors decreased PDE activity. The in vivo estimates of $K_I$ for three PDE inhibitors (IBMX, RO-20-1724, and rolipram) described herein, are consistent with $IC_{50}$ values estimated in vitro for PDE type IV. These data are also consistent with a previous report that identified two isoforms of PDE type IV (PDE4D3 and PDE4D5) in HEK-293 cells based on Western blot analysis (Hoffmann et al., EMBO J., 18:893–903 [1999]). Inhibition of PDE activity did not reveal basal AC activity in HEK-293 cells. In GH4C1 cells, inhibitors selective to PDE types I and IV decreased PDE activity. Using the high cAMP affinity CNG channels, inhibition of PDE type I activity led to a rise in local cAMP concentration in the absence of AC stimulation. This increase revealed substantial basal AC activity in GH4C1 cells. Under the same conditions, no change in cAMP level was observed when PDE type IV inhibitors were added. However, using the lower cAMP affinity, Δ61-90/C460W/E583M channels, inhibition of either PDE type I or type IV increased forskolin-induced cAMP accumulation. These observations point to the presence of two different PDE types: a low $K_m$, PDE type I, and a higher $K_m$, PDE type IV. Based on the apparent cAMP affinities of the two channel constructs, the two $K_m$ values were estimated to be <1 μM and >5 μM.

Interestingly, the data in GH4C1 cells indicate the presence of a futile cycle of cAMP synthesis and hydrolysis. Restricting this phenomenon to subcellular compartments would be advantageous energetically, but the question remains as to why the additional energy is expended by the cells. One possibility is that constant AC and PDE activity allow the system to respond rapidly to a stimulus. In essence, the enzymes are poised to respond to changes in active G-protein or changes in internal $Ca^{2+}$, allowing for rapid increases or decreases in cAMP levels. A similar situation exists in light-adapted photoreceptor cells (See e.g., Nikonov et al., J. Gen. Physiol., 116:795–824 [2000]). Nonetheless, an understanding of the mechanism(s) is not necessary in order to use the present invention.

The existence of PDE type I in GH4C1 cells is consistent with observations showing that CaM antagonists inhibit the hydrolysis of cAMP (Sletholt et al., Acta. Physiol. Scand., 130:333–343 [1987]). Furthermore, a high $K_m$ (28.6 μM) and a low $K_m$ (0.66 μM) PDE have been identified in both GH3 and GH4C1 cells, each PDE with a different $IC_{50}$ for theophylline (Gautvik et al., Mol. Cell. Endocrinol., 26:295–308 [1982]). These $K_m$ values are consistent with the in vivo estimates of the $K_m$ values for PDEs that regulate local cAMP levels discussed herein. The presence of both high and low $K_m$ PDEs offers two possibilities for the shaping of cAMP signals: (1) that both PDE types regulate cAMP levels within a single compartment, or (2) that they differentially regulate cAMP levels in different cellular compartments.

If the two PDE types coexist in the same subcellular compartment then the low $K_m$ PDE would be likely to regulate cAMP levels under basal conditions. Upon further activation of AC, this PDE would be overwhelmed, and large concentrations of cAMP would accumulate locally. The high $K_m$ PDE would be able to efficiently hydrolyze cAMP at these elevated concentrations. Furthermore, it is contemplated that these PDE types are differentially regulated, allowing different feedback mechanisms to control cAMP levels within this compartment.

If the activity of the two PDE types is compartmentalized, it is contemplated that distinct cyclic nucleotide signals are capable of occurring simultaneously in different regions of the cell. Indeed, this possibility seems likely because cAMP can be excluded from areas of the cell by PDE activity (See, Jurevicius and Fischmeister, Proc. Natl. Acad. Sci. USA 93:295–299 [1996]), cAMP is produced in microdomains with restricted diffusional access to the bulk cytosol and different pools of cGMP have different functional effects in ECV304 epithelial cells (Zolle et al., J. Biol. Chem., 275: 25892–25899 [2000]).

It is contemplated that the present invention will find use in measuring local cAMP signals in response to a variety of extracellular stimuli. Indeed, the present invention provides means to investigate how cAMP is capable of differentially regulating more than 200 cellular targets. This requires a quantitative knowledge of how cAMP signals are initiated and terminated. In addition, different PDE subtypes are likely to play crucial roles in shaping the signals in different cellular compartments. Within these compartments, cAMP levels are likely to vary dynamically (Brooker, Science 182:933–934 [1973]; Cooper et al., Nature 374:421–424 [1995]; and Cooper et al., Adv. Second Messenger Phosphoprotein Res., 32:23–51 [1998]), particularly in excitable cells, where $Ca^{2+}$ levels oscillate during a train of action potentials. For example, it is contemplated that modulation of PDE type I by $Ca^{2+}$-CaM in excitable GH4C1 cells contributes to transient or oscillating cAMP signals. In general, dynamic cAMP signals would escape detection with conventional techniques.

DETAILED DESCRIPTION OF THE INVENTION

The present invention provides modified cyclic nucleotide gated (CNG) channels. In particularly preferred embodiments, the modified CNG channels exhibit increased sensitivity and specificity for cAMP, as compared to wild-type CNG channels. In additional embodiments, regulation by $Ca^{2+}$-calmodulin has been removed in the modified CNG channels. Convenient optical methods for detecting changes in cAMP, taking advantage of the $Ca^{2+}$ permeability of the channel are also provided by the present invention. In addition, electrophysiological methods are further provided.

Retinal rod outer segments are the most closely examined second messenger signaling system, in part because the endogenous cyclic nucleotide-gated (CNG) channels have been used as real-time detectors of cGMP concentration (Baylor et al., J. Physiol., 288:589–611 [1979]). Information from biochemical measurements of guanylyl cyclase and cGMP-specific PDE have been combined with real-time measurements of cGMP concentration to characterize the relationship between these enzymes in regulating cGMP levels (See e.g., Fung et al., Proc. Natl. Acad. Sci. USA 78:152–156 [1981]; Koch and Stryer, Nature 334:64–66 [1988]; Gorczyca et al., Proc. Natl. Acad. Sci. USA 91:4014–4018 [1994]; Koutalos et al., J. Gen. Physiol., 106:891–921 [1995a]; Koutalos et al., J. Gen. Physiol., 106:863–890 [1995b]; He et al., Neuron 20:95–102 [1998b]; Tsang et al., Science 282:117–121 [1998]; Chen et al., Nature 403:557–560 [2000]Leskov et al., Neuron 27:525–537 [2000]; and Nikonov et al., J. Gen. Physiol., 116:795–824 [2000]). The convergence of different approaches has led to an unprecedented understanding of feedback signaling within this model system (See e.g., Stryer, J. Biol. Chem., 266:10711–10714 [1991]; Lagnado and Baylor, Neuron 8:995–1002 [1992]; Pugh and Lamb, Biochim. Biophys. Acta 1141:111–149 [1993]; Yarfitz and Hurley, J. Biol. Chem., 269:14329–14332 [1994]; Yau, Invest. Ophthalmol. Vis. Sci., 35:9–32 [1994]; Polans et al., Trends Neurosci., 19:547–554 [1996]; Pugh et al., Biosci. Rep., 17:429–473 [1997]; and Molday, Invest. Ophthalmol. Vis. Sci., 39:2493–2513 [1998], for review). Nonetheless, an understanding of the mechanism(s) is not necessary in order to use the present invention.

During the development of the present invention, it was determined that cAMP concentration can be measured accurately with the rat wild-type (WT) olfactory cyclic nucleotide-gated (CNG) channel (See, FIG. 4 and SEQ ID NO:4), encoded by an adenovirus vector (See, Rich et al., J. Gen.

Physiol., 116:147–161 [2000]). An important finding in multiple cell types was that cAMP is produced in subcellular compartments near the plasma membrane. Diffusion between these compartments and the bulk cytosol is severely restricted. These regions likely allow for rapid and energetically-efficient activation of cAMP-dependent processes, and it is contemplated that these relationships help explain how cAMP can differentially regulate large numbers of cellular targets. However, as indicated above, an understanding of the mechanism(s) is not necessary in order to use the present invention.

As described in greater detail herein, the present invention provides modified CNG channels to increase its sensitivity and specificity for cAMP and to remove regulation by $Ca^{2+}$-CaM. The present invention further provides convenient optical methods for detecting changes in cAMP, taking advantage of the $Ca^{2+}$ permeability of the channel. Using the modified CNG channels, this assay is sensitive to cAMP in the physiologic range (0.1–50 μM). As described herein, this approach has been used to probe the interactions between adenylyl cyclase (AC) and PDE in regulating local cAMP concentration in two cell types, nonexcitable HEK-293 and excitable GH4C1 pituitary cells.

cAMP and Signalling

Much has been learned about the enzymes involved in the generation and breakdown of cAMP (Sunahara et al., Ann. Rev. Pharmacol. Toxicol., 36:461–480 [1996]; and Beavo, Physiol. Rev., 75:725–748 [1995]), and the proteins that mediate the downstream effects of cAMP (Walsh et al., J. Biol. Chem., 243:3763–3765 [1968]; Gray et al., Curr. Opin. Neurobiol., 8:330–334 [1998]; Francis and Corbin, Crit. Rev. Clin. Lab. Sci., 36:275–328 [1999]; and Finn et al., Ann. Rev. Physiol., 58:395–426 [1996]). However, conventional methods have, by and large, been unable to resolve the spatial and temporal features of cAMP signals. Creative attempts to use protein kinase A (PKA) or L-type $Ca^{2+}$ channels to assess changes in cAMP levels have yielded some information. In large invertebrate neurons gradients in cAMP between the processes and the soma have been inferred (Bacskai et al., Science 260:222–226 [1993]; and Hempel et al., Nature 384:166–169 [1996]). Gradients in cAMP have also been deduced in studies of cardiac myocytes, in which only part of the cell was stimulated with isoproterenol (Jurevicius and Fischmeister, Proc. Natl. Acad. Sci. USA 93:295–299 [1996]). Unfortunately, these methods have limited resolution. It has been shown previously that heterologously-expressed, cyclic nucleotide-gated (CNG) channels are able to detect changes in membrane-localized cAMP concentration (Rich et al., J. Gen. Physiol., 116: 147–161 [2000]; Rich et al., J. Gen. Physiol., 118:63–77; and Fagan et al., FEBS Lett., 500:85–90 [2001]) and, using the patch-cram technique, cytosolic cGMP (Trivedi and Kramer, Neuron 21:895–906 [1998]) in real time.

In contrast, in some embodiments of the present invention, the properties of CNG channels are tailored for the measurement of submicromolar cAMP concentrations (Rich et al. [2001], supra). These methodological advances allow the measurement of cAMP produced by low levels of adenylyl cyclase (AC) activity without the need to inhibit phosphodiesterase (PDE) (Rich et al. [2001], supra; and Fagan et al., supra).

During the development of the present invention, comparisons of the measurements of membrane-localized and total cellular cAMP levels in response to prostaglandin $E_1$ ($PGE_1$) stimulation were made. The olfactory CNG channel α subunit containing two mutations, C460W and E583M, were used to monitor cAMP levels near the surface membrane in both cell populations and single cells. These mutations make it possible to measure cAMP concentrations in the 100 nM range, while rendering the channel relatively insensitive to cGMP. Total cAMP accumulation in cell populations was investigated by measuring the conversion of [$^3$H]ATP into [$^3$H]cAMP. The difference between the two measured cAMP signals was striking: a rise and fall in cAMP near the membrane and an increase to a steady level throughout the cell. The segregation of signals helps to explain how cAMP can differentially regulate cellular targets.

Indeed, results provided herein indicate that cAMP signals near the channels are distinct from those in other parts of the cell. Several lines of evidence presented previously suggest that cAMP is produced in subcellular compartments near the surface membrane, and that diffusion between these domains and a cytosolic compartment is significantly impeded (Rich et al., [2000], supra). At a minimum, it is necessary to invoke the same two compartments to explain the current data. With no restriction on diffusion: 1) cAMP concentrations right next to AC are not high enough to activate PKA (Rich et al. [2000], supra), let alone the CNG channels used here (unless the entire cell filled with cAMP); and 2) cAMP would diffuse across a 15–20 μm cell in <0.2 s, which would 'wash out' any spatial differences on a time-scale of tens to hundreds of seconds. The inset to FIG. 5, Panel A shows the two compartment model presented before, with two important additions: a $PGE_1$-induced increase in PDE activity in compartment 1, and a constitutively active PDE in compartment 2. The system is described by the following equations:

$$\frac{dC_1}{dt} = E_{AC} + \frac{J_{12}}{V_1}(C_2 - C_1) - \frac{A \cdot E_1 \cdot C_1}{K_{MI} + C_1} \quad \text{(Eq. 1)}$$

$$\frac{dC_2}{dt} = \frac{J_{12}}{V_2}(C_1 - C_2) - \frac{E_2 \cdot C_2}{K_{M2} + C_2} \quad \text{(Eq. 2)}$$

$$\frac{dA}{dt} = k_A I - k_I A \quad \text{(Eq. 3)}$$

where $V_1$ and V2 are the volumes of compartments 1 and 2, $C_1$ and $C_2$ are the cAMP concentrations, $J_{12}$ is the flux coefficient between compartments, $E_{AC}$ is the synthesis rate of cAMP, $E_1$ and $E_2$ are the maximal cAMP hydrolysis rates, $K_{M1}$ and $K_{M2}$ are the Michaelis constants for PDE activity, A and I are the fraction of active and inactive PDE in compartment 1 (A+I=1), and $k_A$ and $k_I$ are the rate constants of PDE activation and inactivation. The parameters $J_{12}=8.0\times10^{-16}$L/s, $V_1$=0.040 pL, and $V_2$=2.0 pL are the same as those used previously (Rich et al., [2000], supra). AC activity is considered constant, with $E_{AC}$=0.13 μM/s. $K_{M1}$, $E_1$, $KM_2$, and $E_2$ are 0.30 μM, 0.83 μM/s, 1.0 μM, and 0.0020 μs. The rate constants $k_A$ and $k_1$ are 0.0015 $s^{-1}$ and 0.0010 $s^{-1}$. The initial and final (300 s) values of A are 0.10 and 0.36. The parameters used here reflect similar total PDE activities near the plasma membrane and throughout the cytosol, in broad agreement with experiments on PDE type IV in several cell types (Houslay et al., Adv. Pharmacol., 44:225–342 [1998]).

Figure 5:
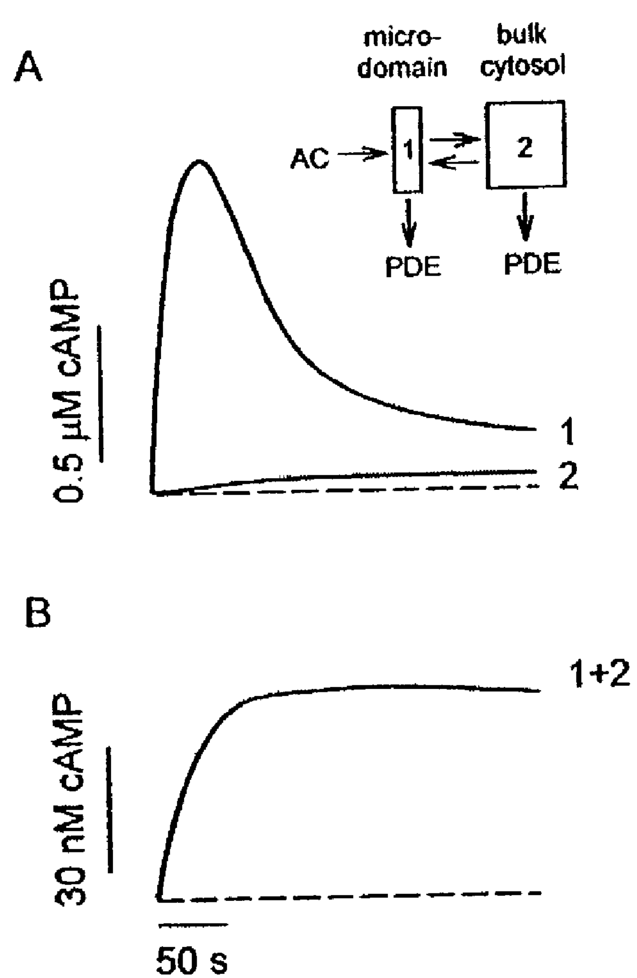
FIG. 5 provides a quantitative description of the localized transient cAMP response and the total cellular cAMP accumulation. The inset of this Figure shows the two compartment model of the cell with a diffusional restriction between the membrane-localized microdomain (compartment 1) and the bulk cytosol (compartment 2). Panel A shows that the rapid activation of AC and slower activation of PDE shape the transient signal in the microdomain. The slow flux of cAMP from the microdomain allows low levels to accumulate in the cytosol. Note that even in the small volume of the microdomain, the concentration of CNG channels would be low (~40 nM), and would not be expected to buffer the measured cAMP signal. Panel B provides results showing that total cAMP levels (microdomain and cytosol) reach a plateau. In this Figure, dashed lines indicate zero cAMP.

Simulations of the model successfully reproduce the local transient change in cAMP, as well as the rise in total cAMP to a plateau (See, FIG. 5). A $PGE_1$-induced increase in PDE activity within compartment 1 is required to explain the data. Slow efflux of cAMP from the microdomain is ultimately balanced by low rates of hydrolysis within the bulk cytosol.

Thus, different relative PDE activities within more than one diffusionally-restricted compartment can explain the generation of distinct cAMP signals, even in a simple, nonexcitable cell.

In morphologically-complex cells like neurons, dendritic spines and other subcellular structures have been shown to be diffusionally isolated compartments (Svoboda et al., Science 272:716–719 [1996]; Bridge et al., Science 248: 376–378 [1990]; Leblanc and Hume, Science 248:372–376 [1990]; Finch and Augustine, Nature 396:753–756 [1998]; and Takechi et al., Nature 396:757–760 [1998]). Surprisingly, results obtained during the development of the present invention indicate that the concept of three-dimensional barriers to diffusion may be generalized to simple cells, which are usually considered to contain a single homogeneous cytosolic compartment. The exact nature of the diffusional barrier is unclear, but it is likely to be formed, at least in part, by ER membrane that is known to come in close apposition to the plasma membrane (Ma et al., Science 287:1647–1651 [2000]; Akita and Kuba, J. Gen. Physiol., 116:697–720 [2000]; and Martin and Fuchs, Proc. Roy. Soc. London B. Biol. Sci., 250:71–76 [1992]). Although localized $Ca^{2+}$ signals have been measured (Roberts et al., J. Neurosci., 10:3664–3684 [1990]; and Jaggar et al., Am. J. Physiol. Cell Physiol., 278:C235–C256 [2000]), these have been attributed primarily to proximity to high-throughput $Ca^{2+}$ sources and the delimiting effects of high-capacity cellular buffers, rather than diffusional barriers. However, it is contemplated that the diffusional barriers to cAMP described herein also influence local $Ca^{2+}$ signals. Regardless, an understanding of the mechanism(s) is not necessary in order to use the present invention.

Thus, experiments conducted during the development of the present invention have resolved distinct cAMP signals in different compartments of a simple, nonexcitable cell: a transient signal in microdomains near the surface membrane and a signal that rises to a plateau throughout the cell. Diffusional restrictions between the microdomains and the cytosol, as well as differential regulation of PDE activity, are required to generate such distinct signals. Segregated cAMP signals allow for differential regulation of cAMP effector proteins like PKA. This may explain a long-standing observation in cardiac myocytes: two agents that both trigger rises in cAMP ($PGE_1$ and isoproterenol) have markedly different downstream effects (Steinberg and Brunton, Ann. Rev. Pharmacol. Toxicol., 41:751–773 [2001]). Similar observations have been made in comparing the effects of $\beta_1$- and $\beta_2$-adrenergic agonists (Steinberg and Brunton, Ann. Rev. Pharmacol. Toxicol., 41:751–773 [2001]; Chen-Izu et al., Biophys. J., 79:2547–2556 [2000]; and Davare et al., Science 293:98–101 [2001]). In this context, it is interesting to reconsider the possible functions of A-kinase anchoring proteins (AKAPs), the scaffolds that tether PKA to cellular targets (Feliciello et al., J. Mol. Biol., 308:99–114 [2001]; and Gray et al., Curr. Opin. Neurobiol., 8:330–334 [1998]). In addition to creating two-dimensional protein arrays that help to ensure the phosphorylation of certain proteins, AKAPs are likely to direct PKA to diffusionally isolated cellular regions in which distinct cAMP signals are produced. The transient nature of the signals measured here limits the diffusional spread of cAMP. However, these signals should still allow for a prolonged activation of PKA because the reassociation of PKA subunits is slow (Ogried and Doskeland, Biochem., 22:1686–1696 [1983]; and Harootunian et al., Mol. Biol. Cell 4:993–1002 [1993]).

Improving the cAMP-Sensing Capabilities of CNG Channels

Figure 6:
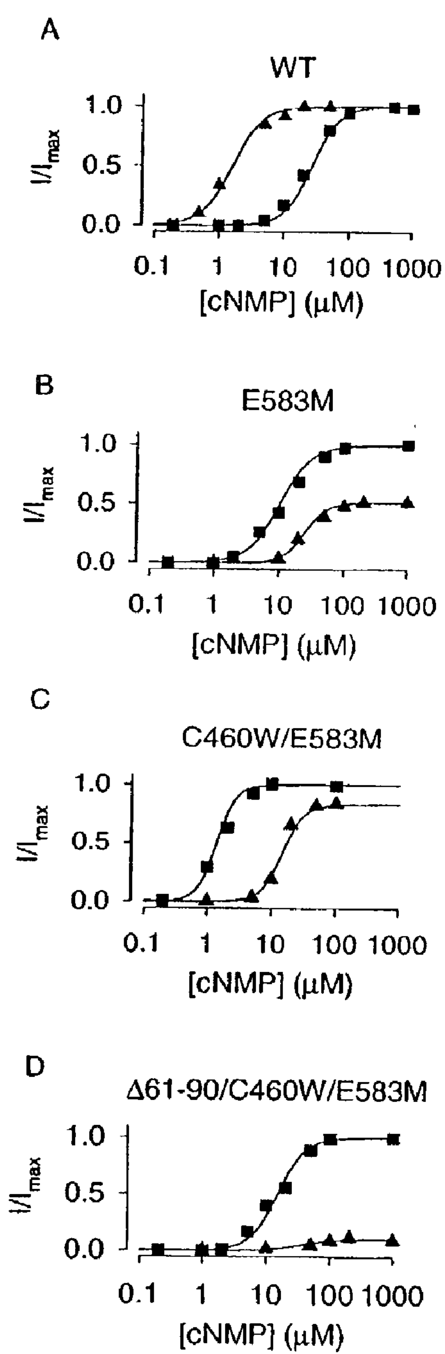
FIG. 6 provides a comparison of CNG channel constructs. Dose-response relations of subunit homomultimers of WT (Panel A), E583M (Panel B), C460W/E583M (Panel C), and Δ61-90/C460W/E583M (Panel D) rat olfactory CNG channels for cAMP (squares) and cGMP (triangles), evaluated at a membrane potential of +50 mV are shown. As indicated, the modified CNG channels are more sensitive to cAMP than WT channels, and less sensitive to cGMP. Solid lines are fits to the Hill equation. For the experiments shown, $K_{1/2}^{cAMP}$=30, 10.3, 1.4, and 15 μM; $K_{1/2}^{cGMP}$=1.6, 25, 11, and 36 μM for WT, E583M, C460W/E583M, and Δ61-90/C460W/E583M channels, respectively. Other fit parameters are included in Table 1, below.

During the development of the present invention, experiments indicated that adenovirus-expressed rat olfactory cyclic CNG channels have several properties that make them excellent cAMP sensors. These properties include their location at the plasma membrane, rapid gating kinetics, and lack of desensitization. Furthermore, these channels appear to co-localize with AC in discrete regions of the membrane, which allows the measurement of localized cAMP signals. However, there are several limitations to the use of WT CNG channels to detect changes in cAMP. First, WT channels have a low apparent affinity for cAMP (Table 1, below and FIG. 6, Panel A), which makes it difficult to detect the low cAMP concentrations that activate protein kinase A (PKA). Second, these channels are activated more readily by cGMP than cAMP (See, FIG. 6, Panel A; See also, Dhallan et al., Nature 347:184–187 [1990]). Third, they can also be activated directly by nitric oxide (NO; Broillet, J. Biol. Chem., 275:15135–15141 [2000]). Fourth, the binding of the $Ca^{2+}$-CaM complex to these channels strongly inhibits channel opening (Liu et al., Science 266:1348–1354 [1994]). To overcome these limitations, the properties of the WT channel were modified, so as to provide the improvements of the present invention.

First, the mutation E583M was introduced into the rat olfactory CNG channel α subunit (See, FIG. 1 and SEQ ID NO:1). Vamum et al. (Varnum et al, Neuron 15:619–625 [1995]) showed that mutation of the corresponding residue in the alpha subunit of the bovine retinal rod CNG channel (D604M) increased the sensitivity to cAMP and decreased the sensitivity to cGMP. As the olfactory channel has a higher overall sensitivity to cyclic nucleotides than the rod channel, the results of these experiments were not predictable. However, in excised patches, the E583M channel displayed increased sensitivity for cAMP and decreased sensitivity for cGMP (Table 1; compare FIG. 6, Panels A and B). Furthermore, cGMP was only a partial agonist of the E583M channel. The current elicited by saturating cGMP was ~40% of the current elicited by saturating cAMP (See, Table 1, and FIG. 6, Panel B).

To further increase the sensitivity to cAMP, a novel second mutant, C460W/E583M, was constructed (See, FIG. 2 and SEQ ID NO:2). As indicated in Table 1, and FIG. 6, Panel C, the double mutant was considerably more sensitive to cAMP than the E583M channel (~10-fold lower $K_{1/2}$).

TABLE 1

Characteristics of CNG Channels Used as cAMP Sensors

| Channel | Membrane Potential (mV) | $K_{1/2}$ cAMP (μM) | $N^{cAMP}$ | $K_{1/2}$ cGMP (μM) | $N^{cGMP}$ | $I_{max}$ cGMP/ $I_{max}$ cAMP |
|---|---|---|---|---|---|---|
| WT | +50 | 36 ± 5 | 2.2 ± 0.1 | 1.6 ± 0.1 | 2.3 ± 0.1 | 1.0 |
| E583M | | 10.5 ± 0.2 | 2.4 ± 0.2 | 28 ± 2 | 2.4 ± 0.12 | 0.40 ± 0.10 |

TABLE 1-continued

Characteristics of CNG Channels Used as cAMP Sensors

| Channel | Membrane Potential (mV) | $K_{1/2}^{cAMP}$ (μM) | $N^{cAMP}$ | $K_{1/2}^{cGMP}$ (μM) | $N^{cGMP}$ | $I_{max}^{cGMP}/I_{max}^{cAMP}$ |
|---|---|---|---|---|---|---|
| C460W/E583M | | 1.2 ± 0.3 | 2.7 ± 0.2 | 12 ± 2 | 2.8 ± 0.3 | 0.84 ± 0.10 |
| Δ61-90/C460W/E583M | | 14.5 ± 1.8 | 2.1 ± 0.1 | 36 ± 4 | 1.8 ± 0.2 | 0.16 ± 0.08 |
| WT | −50 | 36 ± 5 | 2.2 ± 0.1 | 1.3 ± 0.4 | 2.5 ± 0.4 | 1.0 |
| E583M | | 9 ± 2 | 2.2 ± 0.1 | 32 ± 4 | 1.9 ± 0.2 | 0.35 ± 0.16 |
| C460W/E583M | | 0.89 ± 0.23 | 2.2 ± 0.3 | 6.2 ± 1 | 2.7 ± 0.1 | 0.50 ± 0.10 |
| Δ61-90/C460W/E583M | | 10.5 ± 0.1 | 2.2 ± 0.1 | 16 ± 1 | 2.6 ± 0.2 | 0.09 ± 0.06 |

Data are presented as mean ± SEM of three experiments. Hill equation parameters are defined herein. $I_{max}^{cGMP}/I_{max}^{cAMP}$ is the current induced by saturating cGMP divided by the current induced by saturating cAMP.

To remove regulation of the channel by $Ca^{2+}$-CaM binding residues 61 through 90 were deleted using method previously described (Liu et al., Science 266:1348–1354 [1994]). This channel, ΔA61-90/C460W/E583M (See, FIG. 3 and SEQ ID NO:3), is almost as sensitive to cAMP as the E583M channel (See, Table 1, and FIG. 6, Panel D), yet it is virtually insensitive to cGMP. In fact, the current elicited by saturating cGMP was <20% of the current elicited by saturating cAMP (See, Table 1, and FIG. 6, Panel D). Thus, two very useful channel constructs were generated during the development of the present invention for the measurement of cAMP, namely the ΔA61-90/C460W/E583M channel that is sensitive to cAMP at the upper end of the physiological range (~1 to 50 μM); and the C460W/E583M channel that is sensitive to cAMP at the lower end of the physiological range (~0.1 to 5 μM).

In sum, the modified CNG channels of the present invention provide the first ion channels that have been tailored for the measurement of cAMP, as they are primarily activated by cAMP. Although other mutations have been previously made at C460, the present invention provides mutations that exhibit greater changes in cAMP sensitivity. Furthermore, mutations at these positions have apparently never been combined. As little is known about the three-dimensional structure of CNG channels, there is no way to predict the effects of the combined mutations. In addition, the deletion of residues 61–90, which results in the removal of $Ca^{2+}$-CaM sensitivity, dramatically lowers cyclic nucleotide sensitivity (i.e., 10- to 20-fold). Thus, the prior art teaches away from the mutations of the present invention and their use in assay systems with increased sensitivity for cAMP measurements.

Assessment of the Relative cAMP Sensitivity of Channel Constructs In Vivo

Next, experiments were conducted to assess the ability of each channel construct to detect increases in local cAMP concentration. Changes in cAMP concentration were detected using fura-2 to monitor $Ca^{2+}$ influx through CNG channels, as described in the Examples. $Ca^{2+}$ influx induced by different concentrations of forskolin, an AC activator, in the presence of 100 μM IBMX, a nonselective PDE inhibitor was measured. This approach allowed comparisons to be made between the cAMP sensitivities of the different channels to changes in cAMP, regardless of variations in expression levels between experiments. In HEK-293 cells expressing the WT channel, addition of forskolin was followed by a brief delay and an increase in $Ca^{2+}$ influx (See, FIG. 7, Panel A). The delay decreased and the rate of $Ca^{2+}$ influx increased in a dose-dependent manner. Neither effect was saturated at 50 μM forskolin. In cells expressing the E583M channel, addition of forskolin was also followed by a brief delay and an increase in $Ca^{2+}$ influx (FIG. 7, Panel B). As with the WT channel, the delay and the initial rate of $Ca^{2+}$ influx were dose-dependent. However, both effects saturated at 20 μM forskolin, as the 20 and 50 μM forskolin traces overlap, as indicated in FIG. 7, Panel B. In cells expressing the C460W/E583M channel, both the delay and the rate of $Ca^{2+}$ influx were saturated at 5 μM forskolin (FIG. 7, Panel C). In cells expressing the Δ61-90/C460W/E583M channel, addition of forskolin caused similar increases in $Ca^{2+}$ influx as the E583M channel, including saturation of the delay and rate of influx at 20 μM (compare FIG. 7, Panel B with FIG. 7, Panel D). The increased response of the modified channels to forskolin treatment is consistent with the apparent cAMP affinities measured in excised patches in the absence of $Ca^{2+}$-CaM (C460W/E583M>E583M~Δ61-90/C460W/E583>WT channels). There are several factors that may have contributed to the apparent lack of a $Ca^{2+}$-CaM effect on the channels. As indicated in the Examples, the concentrations of fura-2 being used are likely overwhelming high-affinity cellular $Ca^{2+}$ buffers, in terms of the fraction of incoming $Ca^{2+}$ that is bound, and therefore fura-2 is probably significantly reducing the effects of $Ca^{2+}$-CaM. It is also contemplated that other possibilities include: HEK-293 cells do not produce enough CaM to regulate heterologously expressed CNG channels, or that the CaM concentration within microdomains is too low to significantly regulate the channels. Very small forskolin-induced changes in $Ca^{2+}$ influx were observed in HEK-293 cells not expressing CNG channel constructs (See, FIG. 8).

PDE Activity in HEK-293 Cells

As discussed herein, CNG channels monitor cAMP produced in subcellular compartments near the plasma membrane. To assess the extent to which PDE activity affects cAMP levels, forskolin-induced $Ca^{2+}$ influx in the presence and absence of PDE inhibitors was measured. Initially the effects of the nonselective PDE inhibitor, IBMX, were examined using each CNG channel construct as a cAMP sensor. In cells expressing the WT channel, there was little or no change in $Ca^{2+}$ influx in response to an intermediate forskolin concentration (10 μM; See, FIG. 9, Panel A). After a three minute pretreatment with 100 μM IBMX only a modest forskolin-induced increase in $Ca^{2+}$ influx was observed (See, FIG. 9, Panel A), arising from $Ca^{2+}$ entry through WT channels. In cells expressing the E583M channel, a moderate forskolin-induced increase in $Ca^{2+}$ influx was observed in the absence of PDE inhibitors (See, FIG. 9, Panel B). After pretreatment with IBMX, forskolin caused a robust increase in $Ca^{2+}$ influx. In cells expressing the C460W/E583M channel, forskolin-induced increases in $Ca^{2+}$ influx were readily observable, even in the absence of PDE inhibitors (See, FIG. 9, Panel C). Thus, as indicated by a comparison with FIG. 9, Panels B and D, this channel is capable of detecting cAMP in cells with low AC activity. Using the 61-90/C460W/E583M channel as a sensor gave similar forskolin-induced changes in $Ca^{2+}$ influx as the E583M channel, both in the absence and presence of IBMX. These results demonstrate that, in HEK-293 cells, basal PDE activity limits the accumulation of cAMP following a moderate stimulus. However, even in the absence of PDE inhibitors, following stimulation of AC with high concentrations of forskolin (50–100 μM), cAMP reaches levels high enough to activate WT CNG channels (data not shown).

Next, experiments were conducted to pharmacologically identify the PDE type(s) that regulates cAMP levels near CNG channels. The C460W/E583M channels were used to monitor forskolin-stimulated cAMP accumulation in the presence and absence of a series of PDE inhibitors. The reported $IC_{50}$ values of inhibitors used in this study for each PDE type are given in Table 3. The PDE inhibitor concentrations used were typically at least 5-fold higher than the most potent $IC_{50}$. Either vehicle or PDE inhibitors were added at 0 s and 1 μM forskolin was added at 180 s (See, FIG. 10). As indicated in this Figure, in the absence of PDE inhibitors little or no forskolin-induced $Ca^{2+}$ influx was observed; whereas, in the presence of IBMX (10 or 100 μM), or the PDE-type-IV specific inhibitor RO-20-1724 (10 μM) significant forskolin-induced $Ca^{2+}$ influx was observed (See, FIG. 10, Panels A, B and G). Two other PDE type IV inhibitors significantly increased the forskolin-induced $Ca^{2+}$ influx, rolipram (FIG. 11, Panel C) and etazolate (not shown). Inhibitors specific to other PDE families did not affect forskolin-induced $Ca^{2+}$ influx. Similar results were obtained in HEK-293 cells expressing either the WT or Δ61-90/C460W/E583M channels by stimulating cAMP production with higher forskolin concentrations (10 μM, not shown), or when prostaglandin $E_1$ (1 μM) was used to stimulate AC activity (not shown). In these experiments, inhibitor concentrations were used at which specific PDE types should be inhibited. However, many PDE inhibitors are not completely specific (See, Table 3). Also, PDE types VIII and IX are insensitive to IBMX as well as most PDE inhibitors (See, references listed for Table 3). Unfortunately, dipyridamole, the inhibitor to which they are most sensitive, fluoresces and, as such, cannot be used in this assay.

In Vivo Estimates of PDE Inhibitor $K_I$

To further establish that PDE type IV is responsible for the observed IBMX-sensitive PDE activity, the $K_I$'s (inhibition constants) of IBMX and two PDE type IV inhibitors (RO-20-1724 and rolipram) were estimated in vivo. This required developing a quantitative framework to assess the relationship between cAMP synthesis, hydrolysis, and redistribution throughout the cell. Thus, the following formalism was adopted:

$$\frac{d[cAMP]}{dt} = C - \frac{V_{\max} \cdot [cAMP]}{K_m \cdot \left(1 + \frac{[I]}{K_I}\right) + [cAMP]} - k_f \cdot [cAMP] \quad \text{(Eq. 4)}$$

where C is the steady-state rate of cAMP synthesis by AC, $V_{max}$ is the maximal rate of cAMP hydrolysis, $K_m$ is the Michaelis constant for PDE, and $k_f$ is the rate constant of cAMP flux out of the microdomain. In order to estimate $K_I$ for the PDE inhibitors two assumptions were made. First, it was assumed that at low levels of AC stimulation and PDE inhibition, the concentration of local cAMP is low and diffusion of cAMP out of the microdomain is negligible. Second, the assumption was made that cAMP levels reach steady-state shortly after AC stimulation (i.e., equal rates of synthesis and hydrolysis). With these assumptions, Eq. 4 can be simplified to:

$$[cAMP] = \frac{C \cdot K_m}{V_{\max} - C} \cdot \left(1 + \frac{[I]}{K_I}\right) \quad \text{(Eq. 5)}$$

Interestingly, this equation reveals that when the inhibitor concentration is equal to $K_I$ the cAMP concentration is twice that in the absence of inhibitor. At low cAMP concentrations (<$K_{1/2}$ for the channel), the cAMP concentration is proportional to the square root of the $Ca^{2+}$ influx rate (the Hill coefficient for channel activation is approximately 2). Thus, $K_I$ can be estimated using a linear fit to the square root of the slopes of the fluorescence traces as a function of inhibitor concentration (See, FIG. 11).

The high cAMP affinity C460W/E583M channels were used to detect changes in cAMP concentration following pretreatment with PDE inhibitors (added at 0 s) and modest forskolin stimulation (0.5 μM added at 180 s). IBMX, RO-20-1724, and rolipram were completely equilibrated across the plasma membrane of HEK-293 cells in <180 s (data not shown). The assumption that cAMP levels reach steady-state is supported by the long-lasting linear rise in $Ca^{2+}$ concentration following forskolin stimulation (a steady $Ca^{2+}$ influx rate reflects a constant cAMP level; See, FIG. 12). Dose response relations for the three PDE inhibitors are shown in FIG. 11. Based upon fits to this data with Eq. 5 (See, insets in FIG. 11, Panels A–C), the $K_I$ values were estimated to be 11±2 μM (IBMX), 0.13±0.02 μM (RO-20-1724), and 0.07±0.02 μM (rolipram), n=4, which are consistent with published $IC_{50}$ values from in vitro experiments (See, Table 3). To ensure that the results were independent of channel construct, the $K_I$ for RO-20-1724 using the lower cAMP affinity Δ61-90/C460W/E583M channels was also estimated. The $K_I$ (0.15±0.02 μM, n=3) was indistinguishable from that estimated using C460W/E583M channels. These data strongly indicate that PDE type IV is primarily responsible for the IBMX-sensitive component of PDE activity monitored using CNG channels and, thus, for regulating localized cAMP concentration in HEK-293 cells.

At higher PDE inhibitor concentrations, the square root of $Ca^{2+}$ influx rate, which is proportional to cAMP concentration, deviates from linearity (See, FIG. 11). It is contemplated that at higher inhibitor concentrations, cAMP may reach levels ≧ $K_{1/2}$ of the channel. At these concentrations, the relationship between $Ca^{2+}$ influx rate and cAMP concentration deviates from a simple square law. This does not explain why at high levels of PDE inhibition the $Ca^{2+}$ influx rate reaches a plateau. When PDE activity is completely inhibited, forskolin-stimulated cAMP accumulation would continually increase in a confined region of free diffusion. This, in turn, would lead to higher $Ca^{2+}$ influx rates. To ensure that the plateau was not primarily due to channel saturation or $Ca^{2+}$ homeostatic mechanisms, $Ca^{2+}$ influx rates induced by 50 μM forskolin and maximal PDE inhibition were measured in the same experiment. Under these conditions, the $Ca^{2+}$ influx rate greatly exceeded the influx rates induced by 0.5 μM forskolin with PDE inhibition. At increased cAMP concentrations, cAMP efflux from the microdomain is expected to increase; this increased efflux could create the observed plateau. This would be consistent with the diffusionally restricted microdomain model (See, Rich et al. [2000], supra).

PDE Activity in GH4C1 Cells

To further test the utility of this approach, PDE activity in excitable GH4C1 pituitary cells was examined. In all of the experiments shown (See, FIGS. 13–14, and Table 2), 1 μM nimodipine was added at time zero to block $Ca^{2+}$ influx though voltage-gated $Ca^{2+}$ channels (triggered by membrane depolarization due to $Ca^{2+}$ and $Na^{+}$ influx through CNG channels). This concentration of nimodipine was sufficient to block $Ca^{2+}$ influx through voltage-gated $Ca^{2+}$ channels activated by membrane depolarization in 24 mM external KCl, and did not alter forskolin or pCPT-cGMP induced $Ca^{2+}$ influx through CNG channels expressed in HEK-293 cells (data not shown). FIGS. 13 and 14 each depict experiments done on a single batch of cells. As before, similar results were obtained on three other batches. In the experiments that produced the data shown in Table 2, cAMP concentrations were monitored using $Ca^{2+}$ influx through C460W/E583M channels. In these experiments, cells expressing WT CNG channels, as well as control cells (i.e., cells that did not express CNG channels) were used. Either 100 μM IBMX or vehicle (–IBMX; control) were added at time zero. Then, 50 μM forskolin were added at 180 seconds. $d(\Delta F/F_0)/dt$, which is proportional to the $Ca^{2+}$ influx rate, was estimated as described in the Examples. Data are provided as mean±standard error. IBMX or vehicle was added at 60 seconds (first arrow in FIG. 13). Either 10 μM forskolin or 100 nM VIP were added at 240 seconds (second arrow in FIG. 13). In the absence of IBMX, large forskolin or VIP-induced increases in $Ca^{2+}$ influx were observed. When the local PDE activity was inhibited by 100 μM IBMX, substantial basal activity was revealed. This level of basal AC activity was quite different from that observed in HEK-293 cells (See, FIGS. 9 and 10). 1 μM nimodipine was added at time 0 to block endogenous voltage-gated $Ca^{2+}$ channels.

TABLE 2

Effect of PDE Inhibitors on Basal cAMP Levels in GH4C1 Cells

| Inhibitor (μM) | $d(\Delta F/F_0)/dt$ | No. of Experiments |
|---|---|---|
| 100 IBMX | $s^{-1}$ | 5 |
| 100 8-methoxymethyl-IBMX | 0.0025 ± 0.0009 | 4 |
| 10 EHNA | 0.0029 ± 0.0011 | 3 |
| 1 Trequinsin | 0 | 3 |
| 15 Quazinone | 0 | 3 |
| 100 RO-20-1724 | 0 | 4 |
| 100 Rolipram | 0 | 4 |
| 50 Zaprinast | 0 | 3 |

FIG. 13, Panel A shows the forskolin-induced responses of cells expressing WT channels. Either vehicle or 100 μM IBMX was added at 0 s, and 50 μM forskolin was added at 180 s. After the addition of forskolin, there was a short delay followed by an increased $Ca^{2+}$ influx. The slope of the $Ca^{2+}$ influx was greater in the presence of IBMX, indicating higher cAMP levels. In control cells (i.e., cells not expressing CNG channel constructs), no forskolin-induced $Ca^{2+}$ influx was observed in either the presence or absence of IBMX (See, FIG. 13, Panel B). This was true of controls done for all experimental protocols.

Next, forskolin-induced responses and the effects of IBMX in cells expressing the high cAMP affinity construct, C460W/E583M were examined. In these experiments either vehicle or 100 μM IBMX was added at 60 s (FIG. 13, Panels C, D). Interestingly, the addition of IBMX triggered $Ca^{2+}$ influx that was not observed in either control cells or cells expressing the WT channel. Subsequent addition of 10 μM forskolin (See, FIG. 13, Panel C) or 100 nM vasoactive intestinal peptide (VIP; FIG. 13, Panel D) caused additional cAMP accumulation and $Ca^{2+}$ influx. A comparison of responses measured with the WT and C460W/E583M channels indicates that the IBMX-induced response was not due to an increase in local cGMP concentration. Moreover, 100 μM IBMX did not alter CNG channel activity monitored in excised patches (data not shown). Thus, these data indicate that the IBMX-induced $Ca^{2+}$ influx was due primarily to an increase in cAMP arising from basal AC activity.

To identify the PDE family or families that regulate the local cAMP concentration in GH4C1 cells, cAMP accumulation was monitored in the presence and absence of PDE inhibitors (See, Table 2). Again, the high cAMP affinity C460W/E583M channels were used. PDE inhibitors were added at 60 s. Although the addition of IBMX alone triggered $Ca^{2+}$ influx, 10 μM forskolin were added at 240 s as a positive control for CNG channel activity. Only the nonspecific PDE inhibitor, IBMX, and the PDE-type-I specific inhibitor, 8-methoxymethyl-IBMX, induced $Ca^{2+}$ influx through CNG channels (Table 2). This PDE is likely to have a low $K_m$ for cAMP because it is capable of regulating cAMP at concentrations too low for the WT or Δ61-90/C460W/E583M channels to detect. Thus, it is contemplated that a $Ca^{2+}$-CaM stimulated PDE (type I) is primarily responsible for controlling basal cAMP signals in GH4C1 cells.

In addition, PDE activity was monitored using ΔA61-90/C460W/E583M channels to detect changes in cAMP concentration (See, FIG. 14). PDE inhibitors and forskolin were added as described above. With this construct, it was not possible to observe changes in cAMP concentration due to inhibition of PDE activity alone. However, PDE inhibitors caused an increase in forskolin-induced $Ca^{2+}$ influx. As observed using the high cAMP affinity C460W/E583M channels, both IBMX and the PDE-type-I specific inhibitor 8-methoxymethyl-IBMX significantly inhibited PDE activity (See, FIG. 14, Panels A and B). Interestingly, the PDE-type-IV specific inhibitors, RO-20-1724 and rolipram, also inhibited PDE activity (See, FIG. 14, Panels C and D). Inhibitors specific to other PDE types had no effect on the forskolin-induced $Ca^{2+}$ influx (data not shown). No RO-20-1724- or rolipram-sensitive PDE was observed using the high cAMP affinity channel (See, Table 2). It is contemplated that $Ca^{2+}$ influx through the C460W/E583M channels was saturated at cAMP concentrations below the $K_m$ for this PDE. Thus, it is contemplated that there are two different PDE types that regulate local cAMP signals in GH4C1 cells: a low $K_m$, 8-methoxymethyl-IBMX sensitive PDE (type I); and a high $K_m$, RO-20-1724-, rolipram-sensitive PDE (type IV).

The methods described herein are suitable for determination of whether an unknown compound modulates PDE activity or adenylyl cyclase activity. Known inhibitors of PDE (either type-specific inhibitors described above or non-type-specific inhibitors such as IBMX) are mixed, at saturating concentrations, with the unknown compound. If the known PDE inhibitors (particularly type-specific ones) block the effect of the unknown compound (e.g., a rise in cAMP detected as described herein), then the unknown compound is categorized as a candidate PDE modulator. If a series of PDE inhibitors do not prevent the effect of the unknown compound, then the compound is categorized as a candidate adenylyl cyclase modulator. These initial determinations are then verified by using more difficult and time-consuming assays with purified proteins. Thus, the methods described herein provide very useful initial screening tools for compounds that are capable of modulating PDE or adenylyl cyclase activity in living cells.

Definitions

As used herein, the terms "patch clamp" and "patch clamp recording methods" refer to methods that involve sealing the tip of a small (e.g., about 1 micron) orifice glass pipette to the membrane of a cell. Under optimal conditions, a seal resistance of greater than one billion ohms is formed around the rim of the pipette tip between the cell membrane and the glass. When the pipette is connected to an appropriate amplifier, small currents across the patch of membrane inside the pipette tip can be recorded. This initial configuration is referred to as a "cell-attached patch." When such a patch is pulled from the cell, an "excised inside-out patch" forms, with the cytoplasmic face of the patch membrane facing the bathing solution. Alternatively, in the cell-attached configuration, the membrane inside the patch pipette can be ruptured with light suction to provide access to the cell cytoplasm. In this condition, currents are recorded from the entire cell (i.e., "whole-cell configuration"). In the "perforated patch configuration," a pore-forming antimicrobial (e.g., nystatin) is added to the pipette solution to gain electrical access to the cell's interior. This allows currents to be recorded from the entire cell, while retaining divalent cations and larger molecules (e.g., cAMP) in the cell.

As used herein, the term "adenoviruses" (Ad) refers to the double-stranded DNA viruses of the Adenoviridae. The genome of adenoviruses (~36 kb) is complex and contains over 50 open reading frames (ORFs). These ORFs are overlapping and genes encoding one protein are often embedded within genes coding for other Ad proteins. Expression of Ad genes is divided into an early and a late phase. Early genes are those transcribed prior to replication of the genome while late genes are transcribed after replication. The early genes comprise E1a, E1b, E2a, E2b, E3 and E4. The E1a gene products are involved in transcriptional regulation, while the E1b gene products are involved in the shut-off of host cell functions and mRNA transport. E2a encodes the a DNA-binding protein (DBP), while E2b encodes the viral DNA polymerase and preterminal protein (pTP). The E3 gene products are not essential for viral growth in cell culture. The E4 region encodes regulatory protein involved in transcriptional and post-transcriptional regulation of viral gene expression, and subset of the E4 proteins are essential for viral growth. The products of the late genes (e.g., L1–5) are predominantly components of the virion as well as proteins involved in the assembly of virions. The VA genes produce VA RNAs which block the host cell from shutting down viral protein synthesis.

Adenoviruses or recombinant Ad vectors have been exploited for the delivery of foreign genes to cells for a number of reasons including the fact that Ad vectors have been shown to be highly effective for the transfer of genes into a wide variety of tissues in vivo and the fact that Ad infects both dividing and non-dividing cells.

As used herein, the term "virus" refers to obligate, ultra microscopic, intracellular parasites incapable of autonomous replication (i.e., replication requires the use of the host cell's machinery). Adenoviruses, as noted above, are double-stranded DNA viruses. The left and right inverted terminal repeats (ITRs) are short elements located at the 5' and 3' termini of the linear Ad genome, respectively and are required for replication of the viral DNA. The two ITRs are inverted repeats of each other. The "adenovirus packaging sequence" refers to the sequence which comprises five (AI–AV) Packaging signals and is required for encapsulation of the mature linear genome; the packaging signals are located from ~194 to 358 bp in the Ad genome (about 0.5–1.0 mu).

As used herein, the term "primary cell" refers to a cell which is directly obtained from a tissue or organ of an animal whether or not the cell is in culture.

As used herein, the term "cultured cell" refers a cell which has been maintained and/or propagated in vitro. Cultured cells include primary cultured cells and cell lines.

As used herein, the term "primary cultured cells" refers to primary cells which are cultured in vitro and which preferably, though not necessarily, are capable of undergoing ten or fewer passages in in vitro culture before senescence and/or cessation of proliferation.

As used herein, the terms "cell line" and "immortalized cell" refer to a cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Cell lines may be generated spontaneously or by transformation. A "spontaneous cell line" is a cell line which arises during routine culture of cells. A "transformed cell line" refers to a cell line which is generated by the introduction of a "transgene" comprising nucleic acid (usually DNA) into a primary cell or into a finite cell line by means of human intervention Cell lines include, but are not limited to, finite cell lines and continuous cell lines. As used herein, the term "finite cell line" refers to a cell line which is capable of a limited number (from about 1 to about 50, more preferably from about 1 to about 40, and most preferably from about 1 to about 20) of cell divisions prior to senescence. The term "continuous cell line" refer to a cell line which is capable of more than about 50 (and more preferably, an infinite number of) cell divisions. A continuous cell line generally, although not necessarily, also has the general characteristics of a reduced cell size, higher growth rate, higher cloning efficiency, increased tumorigenicity, and/or a variable chromosomal complement as compared to the finite cell line or primary cultured cells from which it is derived.

The term "transgene" as used herein refers to any nucleic acid sequence which is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

As used herein, the term "detection signal" refers to an indicator of the presence or absence of a compound of interest. For example, in some methods of the present invention, fluorescence (i.e., the detection signal) is measured at particular excitation and emission wavelengths, to detect $Ca^{2+}$ influx. In these methods, $Ca^{2+}$ influx was found to cause a decrease in fluorescence ($\Delta F$), which was expressed relative to the pre-stimulus fluorescence ($F_0$) to correct for variations in dye concentration, and to allow for comparison of results on different batches of cells. Although fluorescence was used in the Examples described herein, it is not intended that the present invention be limited to systems that rely upon use of a fluorescent signal. Indeed, assay systems utilizing other signals find use in the present invention, including but not limited to chemiluminescence, bioluminescence, etc., as known in the art.

As used herein, the term "second messenger" refers to small molecules or ions that are generated in the cytoplasm of cells in response to binding of a signal molecule to its receptor on the outer surface of the cell membrane. Two major classes of second messengers are known, including one in which cAMP is involved and one which involves a combination of calcium ions and either inositol triphosphate or diacylglycerol.

As used herein, the term "ion channel" refers to a pathway (i.e., a channel) through the cell membrane, which allows ions to enter and/or exit cells.

As used herein, the term "gated ion channel" refers to ion channels that exhibit selectivity in the timing and/or properties of ions that are allowed to pass through an ion channel and enter or exit a cell. Typically, these channels have a structure which determines the particles that are allowed to enter and/or exit the cell.

The terms "functional calcium channel" and "biologically active calcium channel" interchangeably refer to a calcium channel which allows entry into a cell of a calcium ion in response to a stimulus. Such entry may be determined by measuring the amount of current which flows through the calcium channel in response to the stimulus. Alternatively, a functional calcium channel refers to a calcium channel which binds ligands that have affinity for a calcium channel. For ligand binding assays of a recombinant calcium channel, it is preferred that the host cell which is used for testing the function of the recombinant calcium channel not produce endogenous calcium channel subunits that are of a type or in an amount that interferes with the detection of the recombinant calcium channel. Methods for determining the function of a calcium channel are known in the art.

The term "compound that modulates calcium channel activity" and grammatical equivalents thereof refers to a compound that alters (i.e., reduces or increases) the ability of a calcium channel to pass calcium ions as measured by, for example, the current flowing through the calcium channel. Such compounds include, but are not limited to, calcium channel agonists (e.g., Goldin et al., U.S. Pat. No. 5,312,928, herein incorporated by reference) and antagonists, and compounds that exert their effect on the activity of the calcium channel directly or indirectly.

As used herein, the term "permeant" refers to molecules which are capable of entering cells by means of ion channels or other mechanisms. "Permeant" includes, but is not limited to ions such as chloride, potassium, sodium, and thiocyanate.

The term "biologically active" as used herein, refers to a protein or other biologically active molecules (e.g., catalytic RNA) having structural, regulatory, or biochemical functions of a naturally occurring molecule. Likewise, immunologically active refers to the capability of the natural, recombinant, or synthetic human protein, or any oligopeptide or polynucleotide thereof, to induce a specific immune response in appropriate animals or cells and to bind with specific antibodies.

As used herein, the term "agonist" refers to molecules or compounds which mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. Agonists may include proteins, nucleic acids, carbohydrates, or any other molecules which bind or interact with gated ion channels.

As used herein, the terms "antagonist" and "inhibitor" refer to molecules or compounds which inhibit the action of a "native" or "natural" compound. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist (e.g., prevent opening of the chloride ion channel). Or, antagonists may prevent the function of the agonist (e.g., by blocking the passage of chloride ions in the channels). In contrast to the agonists, antagonistic compounds do not result in physiologic and/or biochemical changes within the cell such that the cell reacts to the presence of the antagonist in the same manner as if the natural compound was present. Antagonists and inhibitors may include proteins, nucleic acids, carbohydrates, or any other molecules which bind or interact with gated ion channels. As used herein, the term modulate, refers to a change or an alteration in the biological activity. Modulation may be an increase or a decrease in protein activity, a change in binding characteristics, a change in ion passage through a gated channel, or any other change in the biological, functional, or immunological properties associated with the activity of a protein or other structure of interest.

As used herein, the term "transformation" refers to the introduction of foreign genetic material into a cell or organism. Transformation may be accomplished by any method known in the art which permits the successful introduction of nucleic acids into cells and which results in the expression of the introduced nucleic acid. For example, transformation may be used to introduce cloned DNA encoding a normal or mutant cyclic nucleotide gated ion channel into a cell which normally does not express this ion channel. Transformation may be accomplished through use of any expression vector. For example, the use of baculovirus to introduce foreign nucleic acid into insect cells is contemplated. The term "transformation" also includes methods such as P-element mediated germline transformation of whole insects. As used herein, the term "transformation" also includes but is not limited to methods such as "transfection" and "transduction."

The term "transfection" generally refers to the introduction of foreign DNA into eukaryotic cells, but may also be used to refer to the introduction of foreign DNA into prokaryotic cells. Transfection may be accomplished by a variety of means known to the art including but not limited to calcium phosphate-DNA co-precipitation, DEAE-dextran-mediated transfection, polybrene-mediated transfection, electroporation, microinjection, liposome fusion, lipofection, protoplast fusion, viral infection (transduction), and biolistics.

As used herein, the term "gene" refers to the deoxyribonucleotide sequences comprising the coding region of a structural gene and including sequences located adjacent to the coding region on both the 5' and 3' ends for a distance of several kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. A genomic form or clone of a gene contains coding sequences, termed exons, alternating with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein, the term "coding region," when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, enhancer elements, etc. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements [i.e., promoters], are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 [1986]; and Maniatis, et al., Science 236:1237 [1987]). For example, the SV40 early gene enhancer is very active in a wide variety of cell types from many mammalian species and has been widely used for the expression of proteins in mammalian cells (Dijkema, et al., EMBO J. 4:761 [1985]). Other examples of promoter/enhancer elements active in a broad range of mammalian cell types are those from the human elongation factor 1 gene (Uetsuki et al., J. Biol. Chem., 264:5791 [1989]; Kim et al., Gene 91:217 [1990]; and Mizushima and Nagata, Nucl. Acids. Res., 18:5322 ([990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

The terms "promoter element" and "promoter" as used herein refer to a DNA sequence that is located at the 5' end of (i.e., precedes) a gene in a DNA polymer and provides a site for initiation of the transcription of the gene into mRNA.

The terms "gene of interest" and "nucleotide sequence of interest" refer to any gene or nucleotide sequence, respectively, the manipulation of which may be deemed desirable for any reason by one of ordinary skill in the art.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are mutations, mismatches, strand breaks, as well as covalent and non-covalent interactions between a nucleic acid sequence (which contains unmodified and/or modified nucleic acids) and other molecules. Illustrative of a covalent interaction between a nucleic acid sequence and another molecule are changes to a nucleotide base (e.g., formation of thymine glycol) and covalent cross-links between double-stranded DNA sequences which are introduced by, for example, ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribonucleic acid sequence. The present invention contemplates modifications which cause changes in a fuinctional property (or properties), such changes manifesting themselves at a variety of time points.

The term "allelic series" when made in reference to a gene refers to wild-type sequences of the gene. An "allelic series of modifications" as used herein in reference to a gene refers to two or more nucleic acid sequences of the gene, where each of the two or more nucleic acid sequences of the gene contains at least one modification when compared to the wild-type sequences of the gene.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch is present.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

The term "modified cell" refers to a cell which contains at least one modification in the cell's genomic sequence.

The term "nucleic acid sequence-modifying agent" refers to an agent which is capable of introducing at least one modification into a nucleic acid sequence. Nucleic acid sequence-modifying agents include, but are not limited to, chemical compounds (e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6MP), mitomycin-C (MMC), procarbazine (PRC), N-methyl-N'-nitro-N-nitrosoguanidine (MNNG), $^3H_2O$, and urethane (UR)), and electromagnetic radiation (e.g., X-ray radiation, gamma-radiation, ultraviolet light).

The term "wild-type" when made in reference to a gene refers to a gene which has the characteristics of that gene when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

A "variant of CNG" is defined as an amino acid sequence which differs by one or more amino acids from the wild-type CNG sequence. The variant may have conservative changes, wherein a substituted amino acid has similar structural or chemical properties (e.g., replacement of leucine with isoleucine). More rarely, a variant may have nonconservative changes (e.g., replacement of a glycine with a tryptophan). Similar minor variations may also include amino acid deletions or insertions (i.e., additions), or both. A variant CNG can be engineered using any number of molecular biology techniques known in the art including but not limited tosite-directed mutagenesis of a CNG clone. Variant CNG channels suitable for use with the methods and compositions of the present invention include but are not limited to homologues of the rat olfactory CNG channel (e.g., CNG channles of other species such as mouse and man).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co. [1981]). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

The terms "targeting vector" and "targeting construct" are used interchangeably to refer to oligonucleotide sequences comprising a gene encoding a cyclic nucleotide gated ion channel. It is preferred that the targeting vector also comprise a selectable marker gene. The targeting vector contains gene sequences sufficient to permit the homologous recombination of the targeting vector into at least one allele of the gene resident in the chromosomes of the target or recipient cell (e.g., ES) cells. Typically, though not necessarily, the targeting vector contains 2 kb to 10 kb of DNA homologous to the gene. This 2 kb to 10 kb of DNA maybe located downstream or upstream of the selectable marker gene, or may be divided on each side of the selectable marker gene. In a preferred embodiment, the selectable marker gene is located upstream of the gene. The targeting vector may contain more than one selectable maker gene. When more than one selectable marker gene is employed, the targeting vector preferably contains a positive selectable marker (e.g., the neo gene) and a negative selectable marker (e.g., the diphtheria toxin (dt gene) or Herpes simplex virus tk (HSV-tk) gene). The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e., which has integrated by virtue of homologous recombination into the target site); cells which survive when grown in medium which selects against the expression of the negative selectable marker do not contain a copy of the negative selectable marker.

In some embodiments, the targeting vectors of the present invention are of the "replacement-type;" integration of a replacement-type vector results in the insertion of a selectable marker into the target gene. Replacement-type targeting vectors may be employed to disrupt a gene resulting in the generation of a null allele (i.e., an allele incapable of expressing a functional protein; null alleles may be generated by deleting a portion of the coding region, deleting the entire gene, introducing an insertion and/or a frameshift mutation, etc.) or may be used to introduce a modification (e.g., one or more point mutations) into a gene.

The terms "selectable marker" or "selectable gene product" as used herein refer to the use of a gene which encodes an enzymatic activity that confers resistance to an antibiotic or drug upon the cell in which the selectable marker is expressed. Selectable markers may be "positive"; positive selectable markers typically are dominant selectable markers (i.e., genes which encode an enzymatic activity which can be detected in any mammalian cell or cell line [including ES cells]). Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin and (3) the bacterial xanthine-guanine phosphoribosyl transferase gene (also referred to as the gpt gene) which confers the ability to grow in the presence of mycophenolic acid. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the diphtheria toxin;

An animal whose genome "comprises a heterologous selectable marker gene" is an animal whose genome contains a selectable marker gene not naturally found in the animal's genome which is introduced by means of molecular biological methods. A heterologous selectable marker is distinguished from an endogenous gene naturally found in the animal's genome in that expression or activity of the heterologous selectable marker can be selected for or against.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "an oligonucleotide having a nucleotide sequence encoding a gene" means a nucleic acid sequence comprising the coding region of a gene (i.e. the nucleic acid sequence which encodes a gene product). The coding region may be present in either a cDNA, genomic DNA or RNA form. When present in a DNA form, the oligonucleotide may be single-stranded (i.e., the sense strand) or double-stranded. Suitable control elements (e.g., enhancers, promoters, splice junctions, polyadenylation signals, etc.) may be placed in close proximity to the coding region of the gene, if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, or other sequences, or a combination of both endogenous and exogenous control elements.

The term "an oligonucleotide sequence comprising at least a portion of a cyclic nucleotide gated ion channel gene" refers to a polynucleotide sequence (i.e., a nucleic acid sequence) containing a nucleotide sequence derived from the cyclic nucleotide gated ion channel gene. This sequence may encode a portion of the cyclic nucleotide gated ion channel gene (i.e., not the entire sequence); alternatively, this sequence may encode the entire sequence or may simply contain non-coding regions derived from the gene or a combination of coding and non-coding regions. The oligonucleotide may be RNA or DNA and may be of genomic or synthetic origin.

As used herein the term "portion" when in reference to a gene refers to fragments of that gene. The fragments may range in size from 10 nucleotides to the entire gene sequence minus one nucleotide. Thus, "an oligonucleotide comprising at least a portion of a gene" may comprise small fragments of the gene or nearly the entire gene.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein, the term "polymerase chain reaction" ("PCR") refers to the methods described in U.S. Pat. Nos. 4,683,195, 4,683,202 and 4,965,188, hereby incorporated by reference, which describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded nucleic acid at or near a specific nucleotide sequence.

The terms "compound" and "drug candidate" refers to any chemical or biological entity (e.g., including pharmaceuticals, drugs, and the like) that can be used to treat or prevent a disease, illness, sickness, or disorder of bodily function. Compounds comprise both known and potential therapeutic compounds. A compound can be determined to be therapeutic by screening, e.g., using the screening methods of the present invention. A "known therapeutic compound" refers to a therapeutic compound that has been shown (e.g., through animal trials or prior experience with administration to humans) to be effective in such treatment or prevention.

A compound is said to be "in a form suitable for administration" when the compound may be administered to an animal by any desired route (e.g., oral, intravenous, subcutaneous, intramuscular, etc.) and the compound or its active metabolites appear in the desired cells, tissue or organ of the animal in an active form.

As used herein, the term "therapeutic amount" refers to that amount of a compound required to neutralize undesirable pathologic effects in a subject.

As used herein, the term "C460W mutation" refers to the replacement of cysteine residue with a tryptophan residue at position 460 of the amino acid sequence of the rat olfactory cyclic nucleotide-gated ion channel. Similar mutations are contemplated to be useful in the context of the present invention, including but not limited to C460F and C460Y substitutions. In fact, any mutation(s) which also serves to decrease the NO sensitivity of the channel and increase the cAMP sensitivity of the channel find use with the methods and compositions of the present invention. Decreased NO sensitivity of a mutant channel can be determined by examining channel function in the presence and absence of a NO donor such as S-nitrosocysteine using published methods (Broillet, J. Biol. Chem., 275:15135–15141 [2000]), and increased cAMP sensitivity of a mutant channel can be determined by generating dose response curves for cAMP using the methods disclosed herein and in Rich et al. (J. Gen. Physiol., 118:63–77 [2001]).

As used herein, the term "E583M mutation" refers to the replacement of the glutamic acid residue with a methionine residue at position 583 of the amino acid sequence of the rat olfactory cyclic nucleotide-gated ion channel. Similar mutations are contemplated to be useful in the context of the present invention, including but not limited to E583V, E583L, and E583I substitutions. In fact, any mutation(s), which also serves to increase cAMP sensitivity and/or decrease cGMP sensitivity finds use with the methods and compositions of the present invention. Increased cAMP sensitivity and/or decreased cGMP sensitivity of a mutant channel can be determined by generating dose response curves for cAMP and cGMP, respectively using the methods disclosed herein and in Rich et al. (J. Gen. Physiol., 118: 63–77 [2001]).

As used herein, the term "Δ61-90 mutation" refers to the deletion of residues 61–90 of the amino acid sequence of the rat olfactory cyclic nucleotide-gated ion channel. Other deletion(s), insertion(s) or substitution(s) which decrease the sensitivity of the channel to Ca2+-CaM regulation find use with the methods and compositions of the present invention. Decreased $Ca^{2+}$-CaM sensitivity of a mutant channel can be determined by examining binding of radiolabeled CaM to mutant channels and measuring electric currents through the mutant channel in the presence of $Ca^{2+}$-CaM using published methods (Liu et al., Science, 266:1348–1354 [1994]).

Importantly, channels with mutations in regions outside of those disclosed herein, are also contemplated to find use with the tools and techniques of the present invention The term "stimulus" as used herein refers to any substance or agent which excites or produces a temporary increase of vital action in either in a whole cell or in any of its parts. Preferred "stimuli" are those which directly or indirectly alter cAMP levels in a cell or in a compartment of a cell.

The term "adenylate cyclase activator" as used herein, refers to compounds such as forskolin which are capable of activating the adenylate cyclase system and the biosynthesis of cAMP. "Forskolin" is derived from the plant coleus forskohlii.

The term "prostaglandin" as used herein, refers to any of any of a group of components derived from unsaturated 20 carbon fatty acids, primarily arachidonic acid, via the cyclooxygenase pathway that are extremely potent mediators of a diverse group of physiologic processes. The abbreviation for prostaglandin is PG, specific compounds are designated by adding one of the letters A through I to indicate the type of substituents found on the hydrocarbon skeleton and a subscript (1, 2 or 3) to indicate the number of double bonds in the hydrocarbon skeleton for example, $PGE_2$. The predominant naturally occurring prostaglandins all have two double bonds and are synthesised from arachidonic acid (5, 8, 11, 14 eicosatetraenoic acid). The 1 series and 3 series are produced by the same pathway with fatty acids having one fewer double bond (8, 11, 14 eicosatrienoic acid) or one more double bond (5, 8, 11, 14, 17 eicosapentaenoic acid) than arachidonic acid. All of the prostaglandins act by binding to specific cell surface receptors causing an increase in the level of the intracellular second messenger cAMP (and in some cases cyclic GMP also).

As used herein, the terms "G-protein" and "GTP protein" refer to any one of a group of intracellular membrane associated proteins with a high affinity for guanine nucleotides, and which serve as second messengers or transducers of the receptor-initiated response to intracellular elements such as enzymes to initiate an effect. They are also mediators of activated cell-surface receptors and their enzymes, or of ion channels. G-proteins are responsible for activating a chain of events that alter the concentration of intracellular signaling molecules such as cAMP and calcium. Thus, the term "G-protein activator" refers to compounds such as cholera toxin, which are capable of activating G-proteins.

The term "phosphodiesterase" as used herein refers to an enzyme that cleaves phosphodiesters to give a phosphomonoester and a free hydroxyl group. In preferred embodiments, the term is used to refer to enzymes such as cAMP phosphodiesterase, that convert cyclic nucleotides to the monoester forms. Thus, the term "phosphodiesterase inhibitor" refers to compounds such as rolipram, which inhibit or antagonize the biosynthesis or actions of a phosphodiesterase.

As used herein, the term "dose response curve" refers to a graph depicting the relationship between the dose of a drug or other chemical (e.g., cAMP) and the degree of response it produces (e.g., electric current).

The term "electric current" as used herein refers to the rate of charge flow past a given point in an electric circuit, measured in amperes (coulombs/second).

As used herein, the term "fluorescent Ca2+ indicator" refers to compounds used to probe Ca2+ concentration via their fluorescent spectral changes upon Ca2+ binding. Fluorescent calcium indicators finding use with the methods and compositions of the present invention include but are not limited to Fura-2, Indo-1, Fluo-3 and Rhod-2.

The term "local intracellular cAMP concentration" refers to the cAMP concentration detected at a restricted or limited part of the cell (e.g., membrane localized). In contrast, the term "total intracellular cAMP concentration" refers to the cAMP concentration detected throughout the cell (e.g., entire accumulated amount divided by the accessible volume of the cell).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: C (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); w/v (weight to volume); v/v (volume to volume); $MgCl_2$ (magnesium chloride); NaCl (sodium chloride); NO (nitric oxide); $OD_{280}$ (optical density at 280 nm); $OD_{600}$ (optical density at 600 nm); AC (adenylyl cyclase); AKAP (A-kinase anchoring protein); HEK (human embryonic kidney); NPE-cAMP (1-(2-nitrophenyl)ethyl-cAMP); oCNG channel (olfactory cyclic nucleotide-gated channel); PDE (phosphodiesterase); CaM (calmodulin); IBMX (3-isobutyl-1-methylxanthine); pCPT-cGMP (8-p-chlorophenylthio-cGMP; RO-20-1724 (4-(3-butoxy-4-methoxybenzyl)-2-imidazolidinone); VIP (vasoactive intestinal peptide); WT (wild-type); Tris (tris(hydroxymethyl) aminomethane); SDS (sodium dodecyl sulfate); PAGE (polyacrylamide gel electrophoresis); SDS PAGE (sodium dodecyl sulfate polyacrylamide gel electrophoresis); PBS (phosphate buffered saline [150 mM NaCl, 10 mM sodium phosphate buffer, pH 7.2]); PEG (polyethylene glycol); PMSF (phenylmethylsulfonyl fluoride); PCR (polymerase chain reaction); RT-PCR (reverse transcription PCR); Molecular Probes (Molecular Probes, Eugene, Oreg.); Calbiochem (Calbiochem-Novabiochem Corp., San Diego, Calif.); Amersham (Amersham Pharmacia Biotech, Piscataway, N.J.); ICN (ICN Pharmaceuticals, Inc., Costa Mesa, Calif.); ATCC (American Type Culture Collection, Rockville, Md.); BioRad (BioRad, Richmond, Calif.); Clontech (CLONTECH Laboratories, Palo Alto, Calif.); Life Technologies, GIBCO BRL, and Gibco BRL (Life Technologies, Inc., Gaithersburg, Md.); Invitrogen (Invitrogen Corp., San Diego, Calif.); New England Biolabs (New England Biolabs, Inc., Beverly, Mass.); Novagen (Novagen, Inc., Madison, Wis.); Sigma (Sigma Aldrich, St. Louis, Mo.); Stratagene (Stratagene Cloning Systems, La Jolla, Calif.); Gemini (Gemini Bioproducts, Calabassas, Calif.); and Hi-Tech (Hi-Tech, Salisbury, United Kingdom). Mathworks (Mathworks, Natick, Mass.); Axon Instruments (Axon Instruments, Foster City, Calif.); Perkin-Elmer (Norwalk, Conn.); and Warner Instruments (Warner Instruments (Warner Instruments, Hamden, Conn.).

Data in the accompanying Figures are representative of at least four experiments. Unless otherwise indicated, all experiments were performed at room temperature (19–22° C.). Forskolin and PDE inhibitors were from Calbiochem. Fura-2/AM and pluronic F-127 were from Molecular Probes. [2-$^3$H]Adenine, [$^3$H]cAMP, and [α-$^{32}$P]ATP were from Amersham. All other chemicals were from Sigma.

Example 1

Cell Culture and Channel Expression

Human embryonic kidney (HEK-293) cells were maintained in culture and infected with adenovirus as known in the art (See, Rich et al. [2001], supra). As described in greater detail in Example 2, an adenovirus encoding the ax subunit of the rat olfactory CNG channel (CNG2, CNC3) with mutations C460W and E583M was constructed using the Quik Change Site-Directed Mutagenesis Kit (Stratagene) and a modification of the AdEasy system (He et al., Proc. Natl. Acad. Sci. USA 95:2509–2514 [1998]; and Orlicky and Schaack, J. Lipid Res., 42:460–466 [2001]). All cells used in cAMP assays were treated with this adenovirus.

Briefly, HEK-293 were maintained in MEM (Life Technologies Inc.) supplemented with 26.2 mM $NaHCO_3$, 10% (v/v) fetal bovine serum (Gemini), penicillin (50 μg/mL), and streptomycin (50 μg/mL), pH 7.0, at 37° C. in a humidified atmosphere of 95% air and 5% $CO_2$. Cells were plated at ~60% confluence in 100 mm culture dishes twenty-four hours prior to infection with the CNG-channel-encoding adenovirus constructs (multiplicity of infection=10 plaque forming units per cell). Two hours post-infection, hydroxyurea was added to the cell media at 2 mM final concentration to partially inhibit viral replication. Twenty-four hours post-infection cells were detached with phosphate-buffered saline containing 0.03% EDTA, resuspended in serum-containing medium, and assayed within 12 hours.

GH4C1 rat pituitary cells (ATCC) were maintained in 13 mL Ham's F-10 medium (Life Technologies) supplemented with 14.3 mM $NaHCO_3$, 15% donor horse serum (Gemini), and 2.5% fetal bovine serum, pH 6.8, in 75 $cm^2$ flasks at 37° C. in a humidified atmosphere of 95% air and 5% $CO_2$. Cells were split weekly (1:4) and washed with fresh medium twice weekly. Cells were plated at ~60% confluence in 100 mm culture dishes twenty-four hours prior to infection with the CNG-channel-encoding adenovirus constructs (multiplicity of infection=50 plaque forming units per cell). Forty-eight hours post-infection cells were detached, resuspended in serum-containing medium, and assayed within 12 hours.

Example 2

Construction of CNG-Channel-Encoding Adenoviruses

In this Example, the methods used to construct CNG-channel encoding adenoviruses are described. As indicated above in Example 1, point mutations were introduced into the α subunit of the WT rat olfactory CNG channel (CNG2, CNC3) using the QuikChange Site-Directed Mutagenesis Kit (Stratagene). Overlap extension PCR was used to delete the $Ca^{2+}$-CaM binding site (amino acids 61–90). A replication-defective adenovirus, in which the channel coding sequence containing the E583M mutation replaced the E1 region, was constructed as known in the art and described previously (Fagan et al., J. Biol. Chem., 274:12445–12453 [2000]). Briefly, the cDNA encoding the mutant channel was ligated into the plasmid pACCMV (See, Gomez-Foix et al., J. Biol. Chem., 267:25129–25134[1992]) under the control of the cytomegalovirus major immediate early (CMV) promoter between the BamHI and SalI sites. The plasmid was then digested with SalI and ligated with a BstBI adaptor. The resultant plasmid was then digested with BstBI and XmnI and ligated with BstBI-digested Ad5dl327$_{Bst}$-gal-terminal-protein complex, that had been isolated by banding purified Ad5dl327$_{Bst}$-gal (Schaack et al., J. Virol., 69:3920–3923 [1995]) virions in 2.8 M CsCl, 4 M guanidine-HCl. The ligation products were used to transfect HEK-293 cells using $Ca_3(PO_4)_2$ precipitation (Jordan et al., Nucl. Acids Res., 24:596–601 [1996]).

The transfected cells were incubated for seven days. The cells were frozen and thawed to release virus, and dilutions used to infect HEK-293 plates for plaque purification. The infected HEK-293 plates were overlaid with medium in Noble agar, fed after 4 days, and stained with X-gal (5-bromo-4-chloro-3-indolyl-D-galactopyranoside) and neutral red. Clear plaques, which were derived from viral chromosomes lacking the LacZ gene of the parental virus, were amplified and analyzed by PCR and restriction digestion for the presence of the mutated CNG channel cDNA.

Adenovirus transducing vectors encoding C460W/E583M and Δ61-90/C460W/E583M channels were constructed using the AdEasy system (He et al., Proc. Natl. Acad. Sci. USA 95:2509–2514 [1998]). The cDNA encoding the mutant channel was ligated into pShuttle-CMV between the KpnI and XbaI sites. The resultant plasmid was then linearized by digestion with PmeI and used to transform *E. coli* strain BJ5183 that had been transformed with pAdEasy-1. A plasmid containing the adenovirus chromosome encoding the mutated CNG channel was digested with PacI to release the adenovirus chromosome, and this DNA was used to transfect HEK-293 cells. After incubation for seven days, the virus was released by freezing and thawing, and plaque purified. The purified virus was tested for the presence of the CNG channel cDNA by PCR. A virus containing the channel cDNA was grown in large scale in HEK-293 cells and purified by banding using CsCl step and isopycnic gradients.

Example 3

Assessment of cAMP Sensitivity of CNG Channel Constructs

To assess the cyclic nucleotide sensitivity of different CNG channel constructs, excised, inside-out patch recordings were made at room temperature (20–21° C.) using an Axopatch-200A patch clamp amplifier (Axon Instruments Inc.). Pipettes were pulled from borosilicate glass and heat polished. Pipettes were lowered onto the cells and gigaohm seals were formed. Patches were excised by shearing cells from the pipette with a jet of liquid. Ionic currents were elicited by 250 ms pulses to membrane potentials of +50 and −50 mV from a holding potential of 0 mV. Current records were sampled at five times the filter setting and stored on an IBM compatible computer. Records were corrected for errors due to series resistance (pipette resistance was 4.1±0.1MΩ). Both the pipette and bath solutions contained (mM): 130 NaCl, 2 HEPES, 0.02 EDTA, and 1 EGTA, pH 7.6. Cyclic nucleotide-induced currents were obtained from the difference between currents in the presence and absence of cyclic nucleotides. Dose response curves for cAMP and cGMP were obtained at +50 and −50 mV in the same patch. The effects of the modifications were assessed using the Hill equation, $I/I_{max}=[cNMP]^N/([cNMP]^N+K_{1/2}{}^N)$, where $I/I_{max}$ is the fraction of maximal current, cNMP represents cyclic nucleotide, $K_{1/2}$ is the concentration that gives half-maximal current, and N is the Hill coefficient, an index of cooperativity. $K_{1/2}$ and N for cAMP were 36±5 μM, 10±2 μM, 1.0±0.3 μM, and 11±1 μM for WT, E583M, C460/E583M, and Δ61-90/C460W/E583M channels, respectively (See, Rich et al., J. Gen. Physiol. [2001], supra).

Example 4

Detection of Local cAMP in Cell Populations

Increases in local cAMP concentration activate CNG channels and trigger $Ca^{2+}$ entry. $Ca^{2+}$ influx was monitored in cell populations using the fluorescent indicator fura-2. Cells were loaded with 4 μM fura-2/AM (the membrane permeant form) and 0.02% pluronic F-127 for 30–40 min, in a buffer containing Ham's F-10 medium supplemented with 1 mg/mL BSA and 20 mM HEPES, pH 7.4. In some experiments, HEK-293 cells were loaded with a higher concentration of fura-2/AM (16 μM) for comparison.

Cells were washed twice, resuspended in the buffer described above (3–4×$10^6$ cells/3 mL buffer solution), resuspended in a solution containing (mM): 145 NaCl, 11 D-Glucose, 10 HEPES, 4 KCl, 1 $CaCl_2$, 1 $MgCl_2$, and 1 mg/mL BSA, pH 7.4 (3–4×$10^6$ cells/3 mL solution), and assayed using an LS-50B spectrofluorimeter (Perkin Elmer). Additions were made by pipetting stock solutions into a stirred cuvette. The solutions were then assayed using an LS-50B spectrofluorimeter (Perkin Elmer). Additions were made by pipetting stock solutions into a stirred cuvette (mixing time~5 s).

Fluorescence was measured at an excitation wavelength of 380 nm and an emission wavelength of 510 nm. Under these conditions $Ca^{2+}$ influx was found to cause a decrease in fluorescence (ΔF), which was expressed relative to the pre-stimulus fluorescence ($F_0$) to correct for variations in dye concentration, and to allow for comparison of results on different batches of cells. $\Delta F/F_0$ was plotted with inverted polarity, so that increases in $Ca^{2+}$ influx were represented as positive deflections. Linear fits to the steady-state $Ca^{2+}$ influx rates were used to quantify the results (Rich et al. [2001], supra). The MATLAB software package (MathWorks) was used for curve fitting and simulations.

Data were sampled at 0.5 Hz and filtered at 0.1 Hz (See FIG. 7, Panels A and B) or sampled at 6 Hz and filtered at 1.2 Hz (See, FIG. 7, Panels C and D).

The measurement of absolute $Ca^{2+}$ influx rates using fluorescence requires that fura-2 overwhelm endogenous $Ca^{2+}$ buffers, and that the relation between fluorescence changes and $Ca^{2+}$ entry be known (Schneggenburger et al., [1993]; Frings et al., [1995]). However, in these experiments, the concern was the relative $Ca^{2+}$ influx rates, which report changes in cAMP levels. This requires only that fura-2 detect a fixed proportion of the entering $Ca^{2+}$ in a given experiment. For this to be true, the concentration of unbound fura-2 should not change appreciably upon $Ca^{2+}$ binding, and cellular $Ca^{2+}$ buffers that are not overwhelmed by fura-2 should also not be significantly depleted by $Ca^{2+}$ binding. Under these conditions, the equilibrium concentration of $Ca^{2+}$-bound fura-2 (CaF), monitored by fluorescence at 380 nm, is given by:

$$[CaF]=\frac{[Ca_T]}{1+\frac{K_F}{[F]}+\frac{K_F}{[F]}\cdot\frac{[B]}{K_B}} \qquad \text{(Eq. 6)}$$

where F represents fura-2, $K_F$ the dissociation constant for $Ca^{2+}$ binding to fura-2, B the endogenous buffer, $K_B$ the dissociation constant for $Ca^{2+}$ binding to the endogenous buffer, and $Ca_T$ the total $Ca^{2+}$ concentration that freely exchanges between fura-2 and the endogenous buffer. The equilibrium assumption is reasonable given the time scale of the experiments presented here (tens to hundreds of seconds) and the time scale of binding and unbinding of $Ca^{2+}$ from fura-2 and endogenous buffers (milliseconds). Eq. 6 indicates that with [F] and [B] unchanged by the binding of $Ca^{2+}$, [CaF] will be a constant fraction of $[Ca_T]$, and therefore directly proportional to the amount of entering $Ca^{2+}$. In experiments in which quantitative information was extracted (e.g., the in vivo estimate of $K_I$ for PDE inhibitors), low levels of $Ca^{2+}$ influx were purposely utilized.

Results from a typical experiment are shown in FIG. 12, in which addition of 0.5 μM forskolin (an adenylyl cyclase activator) and 50 nM rolipram (a PDE inhibitor) caused a rise in cAMP and an increase in $Ca^{2+}$ influx. Additional experiments are described in the following Examples.

There are several lines of evidence that free fura-2 levels did not change significantly at these low influx rates, and that depletion of endogenous buffers did not distort the measurements. First, after a brief delay (during which cAMP rose to steady level), the $Ca^{2+}$ influx rate was constant for a substantial period (linear fit in FIG. 12). Second, the changes in fluorescence over which $Ca^{2+}$ influx rates were measured were always a very small fraction of the total change in fluorescence measured when saturating $Ca^{2+}$ was admitted into the cells (by adding 30 μL of 10% Triton to the cuvette). The fluorescence changes used in the linear fits were generally <10% of the saturated fura-2 response, indicating that unbound fura-2 was predominant. At high levels of $Ca^{2+}$ influx, non-linearities in the traces are likely due to depletion of fura-2 and $Ca^{2+}$ pumping mechanisms. Third, increasing the external fura-2/AM concentration from 4 to 16 μM significantly altered the intracellular fura-2 concentration but had no effect on the measurement of relative $Ca^{2+}$ influx rates or estimates of PDE inhibitor $K_I$. The intracellular concentrations of fura-2 were not determined, but a previous study of neuroblastoma cells and isolated pulmonary artery endothelial cells found that 60 min loading with 10 μM fura-2/AM yielded intracellular fura-2 concentrations of about 130 μM (Oakes et al., [1988]). If HEK-293 cells behave similarly, they would be expected to display intracellular concentrations of 35 and 140 μM under the two loading conditions.

Neher and Augustine (Nether and Augustine [1992]) have shown in adrenal chromaffin cells that 98–99% of entering $Ca^{2+}$ binds to endogenous buffers that are present at high concentration (375–750 μM) but have a low affinity for $Ca^{2+}$ ($K_B$~5–10 μM). Thus, the ratio $[B]/K_B$ in Equation 6 was estimated to be 75. $K_F$ for fura-2 was estimated to be 150 nM. Thus, the $[F]/K_F$ values under the two loading conditions were expected to be 233 and 933. At the higher loading condition, fura-2 may be overwhelming the low-affinity cellular buffers. However, as pointed out above, this is not necessary as long as the buffers were not being depleted. It is very likely that low affinity buffers are present at a high enough concentration that they were not depleted by the low amounts of entering $Ca^{2+}$. Two of the lines of evidence cited above indicate that buffers (including any high-affinity buffers that may be present) did not affect the proportion of $Ca^{2+}$ detected by fura-2: the linearity of the influx traces (FIG. 12 and the observation that increasing fura-2 by a factor of four does not alter the measurement of relative $Ca^{2+}$ influx rates. These results strongly suggest that any high-affinity buffers were overwhelmed by the fura-2 concentrations used.

Example 5

In Vivo Identification of PDE Types in HEK-293 Cells Using CNG Channel Constructs There are over 30 known forms of PDE that have been grouped into 11 families. Of these families, PDE types V, VI, and IX are cGMP-specific. Recently, an isoform of PDE type IV, PDE4A, purified from U937 monocytic cells was shown to be inhibited by rolipram with an $IC_{50}$ of 3 nM (MacKenzie and Houslay Biochem. J., 347:571–578 [2000]). It should be noted that it is contemplated that these efficacies may be modulated in vivo. For example, it has been shown that forms of PDE type IVA are approximately 10-fold more sensitive to rolipram when they bind to the SRC family tyrosyl kinase LYN (McPhee et al., [1999]). Data in Table 3 were obtained using heterologously expressed mouse (types VII, VIII, and X) and human (types I, II, IV, V, VII, IX, and XI) PDEs, as well as endogenous PDEs from dog kidney (type IV), rat brain (type IV), bovine heart (types III and IV), human heart (type II), bovine aorta (types I, III, and V), rabbit aorta (types I, IV, and V), and bovine photoreceptor (type VI). Data in Table 3 were compiled from: (1) Ahluawalia and Rhoads Biochem. Pharmacol., 31:665–669 (1982); (2) Ahn et al., Biochem. Pharmacol., 38:3331–3339 (1989); (3) Beavo, Adv. Second Messenger Phosphoprot. Res., 22:1–38 (1988); (4) Bolger et al., Mol. Cell. Biol., 13:6558–6571 (1993); (5) Bolger et al. Biochem. J., 328: 539–548 (1997); (6) Coste and Grondin, Biochem. Pharmacol., 50:1577–1585 (1995); (7) Epstein et al., Arch. Biochem. Biophys., 218:119–133 (1982); (8) Fawcett et al., Proc. Natl. Acad. Sci. USA 97:3702–3707 (2000); (9) Fisher et al., J. Biol. Chem., 273:15559–15564 (1998); (10) Gardner et al., Biochem. Biophys. Res. Commun., 272:186–192 (2000); (11) Harrison et al., Meth. Enzymol., 15:685–702 (1988); (12) Hetman et al., Proc. Natl. Acad. Sci. USA 97:472–476 (2000); (13) Holck et al., J. Cardiovasc. Pharm., 6:520–530 (1984); (14) Lorenz and Wells, Mol. Pharmacol., 23:424–430 (1983); (15) Loughney et al., J. Biol. Chem., 271:796–806 (1996); (16) Loughney et aL,Gene 216:139–147 (1998); (17) Nemoz et al., Biochem. Pharmacol., 15:2997–3000 (1985); (18) Podzuweit et al., Cell Signal 7:733–738 (1995); (19) Rosman et al., Gene 191: 89–95 (1997); (20) Soderling et al., Proc. Natl. Acad. Sci. USA 95:8991–8996 (1998a); (21) Soderling et aL, J. Biol. Chem., 273:15553–15558 (1998b); (22) Soderling et al., Proc. Natl. Acad. Sci., 96:7071–7076 (1999); and (23) Whalin et aL, Mol. Pharmacol., 39:711–717 (1991). References cited for various inhibitors include: IBMX[3,6,8,10-12,15,16,20-22], 8-M-IBBX[2,4,14,15], EHNA[12,16,18,22], Trequinsin[23], Quazinone[13], Etazolate[1], RO-20-1724[7,9,12,20,21,23], Rolipram[5,8,9,15,17,20-23], and Zaprinast[6,8,9,15,16,20-22]. Blank spaces in Table 3 indicate that these data are not available.

The PDE type(s) that regulates cAMP levels near CNG channels in HEK-293 were identified cells using the $Ca^{2+}$ influx assay in cell populations as described in EXAMPLE 3. The C460W/E583M channels were used to monitor forskolin-stimulated cAMP accumulation in the presence and absence of a series of PDE inhibitors. The reported $IC_{50}$ values of inhibitors used in this experiment for each PDE type are given in Table 3. The PDE inhibitor concentrations used were typically at least 5-fold higher than the most potent $IC_{50}$. Either vehicle or PDE inhibitors were added at 0 s and 1 μM forskolin was added at 180 s (See, FIG. 10). In the absence of PDE inhibitors, little or no forskolin-induced $Ca^{2+}$ influx was observed. However, in the presence of IBMX (10 or 100 μM), or the PDE-type-IV specific inhibitor RO-20-1724 (10 μM), significant forskolin-induced $Ca^{2+}$ influx was observed (See, FIG. 10, Panels A,B, and G). Two other PDE type IV inhibitors significantly increased the forskolin-induced $Ca^{2+}$ influx, rolipram (See, FIG. 11, Panel C) and etazolate (data not shown). Inhibitors specific to other PDE families did not affect forskolin-induced $Ca^{2+}$ influx. Similar results were obtained in HEK-293 cells expressing Δ61-90/C460W/E583M channels by stimulating cAMP production with higher forskolin concentrations (10 μM, data not shown), or when $PGE_1$ (1 μM) was used to stimulate AC activity (data not shown). In these experiments, inhibitor concentrations were used at which specific PDE types should be inhibited. However, many PDE inhibitors are not completely specific (See, Table 3).

TABLE 3

Specificity of PDE Inhibitors for Different PDE Families

| Inhibitor | RS (PDE) | I | II | III | IV | V | VI | VII | VIII | IX | X | XI |
|---|---|---|---|---|---|---|---|---|---|---|---|---|
| IBMX | NS | 2–3 | 20–50 | 2 | 5–15 | 4–7 | 10 | 2–8 | >200 | >200 | 2.6 | 49.8 |
| 8-M-IBBX | I | 2–8 | | 69 | >100 | | | | | | | |

TABLE 3-continued

Specificity of PDE Inhibitors for Different PDE Families

| Inhibitor | RS (PDE) | I | II | III | IV | V | VI | VII | VIII | IX | X | XI |
|---|---|---|---|---|---|---|---|---|---|---|---|---|
| EHNA | II | | 0.5–1 | | | >500 | | >100 | >100 | >100 | 69 | |
| Trequinsin | III | | 0.5–2 | 0.0003 | | | | | | | | |
| Quazinone | III | | | 0.6 | | | | | | | | |
| Etazolate | IV | | | | | | | | | | | |
| RO-20-1724 | IV | 200 | >100 | 52 | | 250 | | >200 | >200 | | | |
| Rolipram | IV | >150 | >100 | | | >100 | | >100 | >200 | >200 | 47 | >100 |
| Zaprinast | V-VI | 3-10 | 70 | 10 | 0.2–0.5 | 0.15 | >50 | >100 | 29–35 | 11 | 12 | |

NS = Non-selective

Example 6

In Vivo Assessment of PDE Inhibitor $K_I$ Using Modified CNG Channels

To further establish that PDE type IV is responsible for the observed IBMX-sensitive PDE activity, the $K_I$'s (inhibition constants) of IBMX and two PDE type IV inhibitors, RO-20-1724 and rolipram were estimated in vivo. This required developing a quantitative framework to assess the relationship between cAMP synthesis, hydrolysis, and redistribution throughout the cell. Thus, the following formalism was adopted:

$$\frac{d[cAMP]}{dt} = C - \frac{V_{max} \cdot [cAMP]}{K_m \cdot \left(1 + \frac{[I]}{K_I}\right) + [cAMP]} - k_f \cdot [cAMP] \quad \text{(Eq. 4)}$$

where C is the steady-state rate of cAMP synthesis by AC, $V_{max}$ is the maximal rate of cAMP hydrolysis, $K_m$ is the Michaelis constant for PDE, and $k_f$ is the rate constant of cAMP flux out of the microdomain. In order to estimate $K_I$ for the PDE inhibitors, two assumptions were made. First, it was assumed that at low levels of AC stimulation and PDE inhibition, the concentration of local cAMP is low and diffusion of cAMP out of the microdomain is negligible. Second, it was assumed that cAMP levels reach steady-state shortly after AC stimulation (i.e., equal rates of synthesis and hydrolysis). With these assumptions, Equation 4 can be simplified to:

$$[cAMP] = \frac{C \cdot K_m}{V_{max} - C} \cdot \left(1 + \frac{[I]}{K_I}\right) \quad \text{(Eq. 5)}$$

Interestingly, this equation reveals that when the inhibitor concentration is equal to $K_I$ the cAMP concentration is twice that in the absence of inhibitor. At low cAMP concentrations ($<K_{1/2}$ for the channel), the cAMP concentration is proportional to the square root of the $Ca^{2+}$ influx rate (the Hill coefficient for channel activation is approximately 2). Thus, $K_I$ can be estimated using a linear fit to the square root of the slopes of the fluorescence traces as a function of inhibitor concentration (See, FIG. 11).

The high cAMP affinity C460W/E583M channels were used to detect changes in cAMP concentration following pretreatment with PDE inhibitors (added at 0 s) and modest forskolin stimulation (0.5 μM added at 180 s). IBMX, RO-20-1724, and rolipram were completely equilibrated across the plasma membrane of HEK-293 cells in <180 s (data not shown). The assumption that cAMP levels reach steady-state is supported by the long-lasting linear rise in $Ca^{2+}$ concentration following forskolin stimulation (a steady $Ca^{2+}$ influx rate reflects a constant cAMP level; See, FIG. 12). Dose response relations for the three PDE inhibitors are shown in FIG. 11. Based upon fits to this data with Equation 8 (see insets in FIG. 11, Panels A–C), the $K_I$ values were estimated to be 11±2 μM (IBMX), 0.13±0.02 μM (RO-20-1724), and 0.07±0.02 μM (rolipram), n=4, which are consistent with published $IC_{50}$ values from in vitro experiments (See, Table 3). To ensure that the results were independent of channel construct the $K_I$ for RO-20-1724 was also estimated using the lower cAMP affinity Δ61-90/C460W/E583M channels. The $K_I$ (0.15±0.02 μM, n=3) was indistinguishable from that estimated using C460W/E583M channels. These data strongly suggest that PDE type IV is primarily responsible for the IBMX-sensitive component of PDE activity monitored using CNG channels and, thus, for regulating localized cAMP concentration in HEK-293 cells.

Example 7

Measurement of $PGE_1$-Induced cAMP Responses in HEK-293 Cell Populations

In this Example, experiments conducted to detect cAMP levels in cells are described. Changes in cyclic AMP concentrations in response to $PGE_1$ stimulation were monitored in HEK-293 cells by measuring $Ca^{2+}$ influx through C460W/E583M CNG channels (See, Rich et al. [2001], supra). HEK-293 cells express a variety of extracellular receptors including prostanoid receptors (Thomas and Hoffman, Mol. Pharmacol., 49:907–914 [1996]), and the cAMP-specific PDE type IV (Rich et al [2001], supra; and Hoffman et al., EMBO J., 18:893–903 [1999]). Based on PCR analysis, these cells also appear to express AC types II, III, VI, and VII, (Hellevuo et al., Biochem. Biophys. Res. Commun., 192:311–318 [1993]). C460W/E583M channels were expressed heterologously using an adenovirus construct (See, Rich et al. [2001], supra). The $Ca^{2+}$ permeability of the channel was used to detect changes in local cAMP concentration; the fluorescent indicator fura-2 was used to monitor $Ca^{2+}$ entry. With this approach, incremental changes in cAMP concentration are readily detected as changes in relative $Ca^{2+}$ influx rates through C460W/E583M channels (See, Rich et al., [2001], supra).

FIG. 16 provides a comparison of membrane-localized (A) and total cAMP (B) levels in cell populations. FIG. 16, Panel A, shows that sustained application of 10 μM $PGE_1$ in the absence of PDE inhibitor caused an increase in $Ca^{2+}$ influx, followed by a decline in $Ca^{2+}$. Little or no increase in $Ca^{2+}$ was observed in cells not expressing the channel. The initial interpretation was that $PGE_1$ triggered a rise and fall in local cAMP concentration: the rise caused an increase in $Ca^{2+}$ influx through CNG channels; the subsequent fall in cAMP led to reduced $Ca^{2+}$ influx; and, $Ca^{2+}$ pumping mechanisms caused the decline in $Ca^{2+}$ levels. In support of this interpretation, $PGE_1$ in the presence of the PDE inhibitor IBMX caused $Ca^{2+}$ to rise along a similar time-course, but the decay phase was abolished. These results indicate that the underlying cause of the decay phase was hydrolysis of cAMP. In populations of cells expressing C460W/E583M channels, $PGE_1$ caused total cellular cAMP accumulation, assessed as the conversion of [$^3$H]ATP to [$^3$H]cAMP, to rise to a plateau in the absence of IBMX (See, FIG. 16, Panel B). This is in marked contrast to the transient increase in cAMP inferred from FIG. 16, Panel A.

The basis for the transient response was investigated further, as shown in FIG. 17. Transient responses were observed over a large range of $PGE_1$ concentrations, from 0.01 to 10 μM (FIG. 17, Panel A). Forskolin, an activator of AC, also triggered dose-dependent rises in $Ca^{2+}$ influx, as shown in FIG. 17, Panel B. However, these responses, unlike the $PGE_1$-induced responses, did not decline. Similarly, using the same assay, the responses of rat glioma C6-2B cells to isoproterenol and rat pituitary-derived GH4C1 cells to vasoactive intestinal peptide did not decline on a similar time-scale (See, Rich et al., J. Gen. Physiol., 118:63–77 [2001]; and Fagan et al., FEBS Lett., 500:85–90 [2001]). Thus, the activation of AC alone does not necessarily cause transient $Ca^{2+}$ responses. Taken together, these results indicate that the decline was due to a reduction in AC activity and/or an increase in PDE activity. The decline was unlikely to result primarily from a reduction in AC activity (e.g., receptor desensitization), because of the sustained accumulation of total cellular cAMP in the presence of IBMX (See, FIG. 16, Panel B). To verify this, 100 μM IBMX was added at various times after $PGE_1$ application. Even 50 min after the addition of $PGE_1$, IBMX triggered a rapid $Ca^{2+}$ influx, as shown in FIG. 17, Panel C, indicative of a sharp rise in cAMP level. The type-IV-specific PDE inhibitor RO-20-1724 (10 μM) also caused sharp increases in cAMP (the maximal slopes were indistinguishable from those induced by IBMX).

In the absence of $PGE_1$, PDE inhibitors caused no measurable $Ca^{2+}$ influx. These experiments suggest that AC activity did not decrease appreciably, but instead that PDE activity was up-regulated. To test whether $PGE_1$ did indeed increase the total PDE activity, 100 nM $PGE_1$ were added at various times after the initial application of 100 nM $PGE_1$ (a subsaturating concentration). There was a negligible response to the subsequent addition of $PGE_1$, even after 50 min (FIG. 17, Panel D). Taken together, the results of the experiments shown in FIG. 17, Panels C and D argue that the cAMP transient is due to an initial increase in AC activity, followed by a more profound increase in PDE activity. These results are consistent with previous studies showing that neurotransmitters and hormones, including $PGE_1$, regulate PDE activity as well as cyclase activity (Trivedi and Kramer, Neuron 21:895–906 [1998]; Alvarez et al., Mol. Phannacol., 20:302–309; Macphee et al., J. Biol. Chem., 263:10353–10358 [1988]; Conti et al., Endocrine Rev., 16:370–389 [1995]; and Houslay et al., Adv. Pharmacol., 44:225–342 [1998]). As indicated herein, these processes are crucial for the generation of spatially and temporally distinct cAMP signals.

Example 8

Measurement of Forskolin- and VIP-Induced Responses in GH4C1 Cells

In this Example, experiments conducted to examine the response of excitable GH4C1 pituitary cells to stimulation by either forskolin or the hormone vasoactive intestinal peptide (VIP), in the presence of absence of PDE inhibitors are described. In the experiments described, 1 μM nimodipine was added at time zero to block $Ca^{2+}$ influx though voltage-gated $Ca^{2+}$ channels (triggered by membrane depolarization due to $Ca^{2+}$ and $Na^+$ influx through CNG channels). This concentration of nimodipine was sufficient to block $Ca^{2+}$ influx through voltage-gated $Ca^{2+}$ channels activated by membrane depolarization in 24 mM external KCl, and did not alter forskolin or pCPT-cGMP induced $Ca^{2+}$ influx through CNG channels expressed in HEK-293 cells (data not shown).

FIG. 13, Panel A, shows the forskolin-induced responses of cells expressing WT channels. Either vehicle or 100 μM IBMX was added at 0 s and 50 μM forskolin was added at 180 s. After the addition of forskolin, there was a short delay followed by an increased $Ca^{2+}$ influx. The slope of the $Ca^{2+}$ influx was greater in the presence of IBMX, indicating higher cAMP levels. In control cells (i.e., cells not expressing CNG channel constructs), no forskolin-induced $Ca^{2+}$ influx was observed in either the presence or absence of IBMX (See, FIG. 13, Panel B). This was true of controls done for all experimental protocols.

Next, forskolin-induced responses and the effects of IBMX in cells expressing the high cAMP affinity construct, C460W/E583M were examined. In these experiments either vehicle or 100 μM IBMX was added at 60 s (See, FIG. 13, Panels C and D). Interestingly, the addition of IBMX triggered $Ca^{2+}$ influx that was not observed in either control cells or cells expressing the WT channel. Subsequent addition of 10 μM forskolin (See, FIG. 13, Panel C) or 100 nM VIP (See, FIG. 13, Panel D) caused additional cAMP accumulation and $Ca^{2+}$ influx. A comparison of responses measured with the WT and C460W/E583M channels indicated that the IBMX-induced response was not due to an increase in local cGMP concentration. Moreover, 100 μM IBMX did not alter CNG channel activity monitored in excised patches (data not shown). Thus, these data indicate that the IBMX-induced $Ca^{2+}$ influx was due primarily to an increase in cAMP arising from basal AC activity.

Example 9

Measurement of Local cAMP in Single Cells

Single-cell cAMP measurements were made using either the perforated patch or whole cell patch clamp technique (Rich et al. [2000], supra). In the perforated patch configuration, the pore forming antibiotic nystatin was added to the pipette solution to gain electrical access to the cell's interior while retaining divalent cations and larger molecules like cAMP in the cell. Recordings were made using an Axopatch-200A patch clamp amplifier (Axon Instruments). Pipette resistance was limited to 5 ΩM and averaged 3.4±0.5 ΩM (measurements provided herein are expressed as mean±standard deviation). In the perforated patch configuration, a steady access resistance was obtained 5–15 minutes following seal formation. Capacitive transients were elicited by applying −30 mV steps from the holding potential of −20 mV for calculation of access resistance (100±40 MΩ). These quantities were monitored throughout the experiments to ensure stable electrical access was maintained. Current records were typically sampled at five times the filter setting. Records were digitally filtered at 12 Hz, resampled at 60 Hz, and corrected for errors due to series resistance. The control bath solution contained (mM): 140 NaCl, 4 KCl, 11 glucose, 10 HEPES, and either 0.1 or 10 $MgCl_2$, pH 7.4. Solutions were applied using the SF-77B fast-step solution switcher (Warner Instruments). The mechanical switch time was 1 ms. The time to exchange the extracellular solution was measured by applying a 140 mM KCl solution to a depolarized cell (+50 mV), and monitoring changes in current through endogenous voltage-gated $K^+$ channels; for each experiment, it was less than 60 ms. The pipette solution in perforated patch experiments contained 70 mM KCl, 70 mM potassium gluconate, 4 mM NaCl, 0.5 mM $MgCl_2$, 10 mM HEPES, pH 7.4, and 50–200 μg/ml nystatin. In most of these experiments, the pipette solution also contained 1 mM cAMP; at the end of the experiment the maximal cAMP-induced current could be measured by rupturing the cell membrane at the tip of the pipette with suction, allowing saturating cAMP to diffuse to the channels (See, Rich et al. [2000], supra). In whole cell experiments, 5 mM $K_2ATP$ and 0.1 mM $Na_2GTP$ were added to the pipette solution, and nystatin was not included.

The cyclic nucleotide sensitivity of the C460W/E583M CNG channel was assessed in excised, inside-out patches as known in the art (See, Rich et al. [2001], supra). $K_{1/2}$ and N were 1.1±0.3 μM and 2.1±0.4 at +50 mV; and 1.0±0.3 μM and 2.0±0.3 at −50 mV (n=11). With these values, the cAMP concentration could be calculated from currents measured in perforated patch experiments (Rich et al. Proc. Natl. Acad. Sci. [2001], supra). For example, if $I/I_{max}$ was found to be 0.6, the estimated cAMP concentration would be 1.2 μM. It should be noted that the low concentration of channels expressed in these cells (~1 nM) did not significantly buffer the measured cAMP signals.

The response to $PGE_1$ in single cells was examined by directly measuring ionic currents through C460W/E583M channels with the perforated patch clamp technique. This approach has higher temporal resolution and dynamic range than the $Ca^{2+}$ influx assay, and the response can be calibrated, allowing for accurate measurement of cAMP concentration. These experiments were done in nominally $Ca^{2+}$-free solutions, which increased currents through the channels ($Ca^{2+}$ is a permeant blocker), and removed the possibility that $Ca^{2+}$ entry inhibited the channels (See, Finn et al., Ann. Rev. Physiol., 58:395–426 [1996]). The responses of two different cells to rapid application of 1 μM $PGE_1$ are shown in FIG. 15, Panels A and B. Inward currents were measured at a holding potential of −20 mV. The currents were converted to cAMP concentration based on the channel's dose-response relation determined in excised membrane patches. The cAMP signals were transient, rising more sharply than they decayed, in general agreement with the cAMP changes inferred from $Ca^{2+}$ influx experiments in cell populations. The absence of extracellular $Ca^{2+}$ in these experiments, and, as noted earlier, the lack of a $PGE_1$-stimulated rise in intracellular $Ca^{2+}$ in control cells, indicate that the transient cAMP responses were not caused by $Ca^{2+}$ feedback mechanisms. Additional controls are indicated above, in the Description of the Drawings. The shapes of the responses were similar across six cells, but the kinetics varied (width at half height 87±53 s). The time-course in shown in FIG. 15, Panel A was about average for the single cell measurements, while the time-course shown in FIG. 15, Panel B (from a different cell) was considerably faster. The average amplitude of the cAMP signal in five cells was 0.7±0.4 μM. When 100 μM IBMX was added after 100 nM $PGE_1$ (See, FIG. 15, Panel C), the current rose to a plateau (n=4). This demonstrates the persistent activation of AC by $PGE_1$, as observed in cell populations (See, FIG. 17, Panel C).

All publications and patents mentioned in the above Specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, and/or related fields are intended to be within the scope of the present invention.

We claim:

1. An isolated nucleic acid encoding a modified mammalian olfactory cyclic nucleotide-gated ion channel alpha subunit, wherein said channel comprises a mutation, wherein said mutation comprises a substitution at a residue corresponding to position 583 of SEQ ID NO:8, and wherein said channel has increased cAMP sensitivity, and decreased cGMP sensitivity as compared to a wild type channel.

2. The nucleic acid of claim 1, wherein said substitution at a residue corresponding to position 583 of SEQ ID NO:8 is selected from the group consisting of E583M, E583V, E583L and E583I.

3. The nucleic acid of claim 1, wherein said cGMP-induced current is 40% or less than said cAMP-induced current.

4. The nucleic acid of claim 1, wherein said increased cAMP sensitivity comprises a $K_{1/2}$ at least ten-fold lower than that observed for a nucleic acid encoding a wild type channel.

5. The nucleic acid of claim 1, wherein said decreased cGMP sensitivity comprises a $K_{1/2}$ at least ten-fold higher than that observed for a nucleic acid encoding a wild type channel.

6. The nucleic acid of claim 1, wherein said mutation further comprises a substitution at a residue corresponding to position 460 of SEQ ID NO:8.

7. The nucleic acid of claim 6, wherein said substitution at a residue corresponding to position 460 of SEQ ID NO:8 is selected from the group consisting of C460W, C460F and C460Y.

8. The nucleic acid of claim 6, wherein said mutation further comprises a 61–90 deletion at residues corresponding to positions 61–90 of SEQ ID NO:8.

9. An isolated nucleic acid encoding a modified rat olfactory cyclic nucleotide-gated ion channel alpha subunit, wherein said channel alpha subunit comprises a glutamic acid (E) to methionine (M) substitution at a residue corresponding to position 583 of SEQ ID NO:8.

10. The isolated nucleic acid of claim 9, wherein said channel alpha subunit further comprises a cysteine (C) to tryptophan (W) substitution at a residue corresponding to position 460 of SEQ ID NO:8.

11. The isolated nucleic acid of claim 10, wherein said channel alpha subunit further comprises a 61–90 deletion at residues corresponding to positions 61–90 of SEQ ID NO:8.

12. The isolated nucleic acid of claim 9, wherein said channel comprises an amino acid sequence selected from the group consisting of SEQ ID NO:5, SEQ ID NO:6, and SEQ ID NO:7.

13. An expression vector comprising the nucleic acid of claim 9.

14. The expression vector of claim 13, wherein said vector is a recombinant adenovirus vector.

15. An isolated host cell comprising the expression vector of claim 13, wherein said host cell is selected from the group consisting of a prokaryotic cell and a eukaryotic cell.

16. The host cell of claim 15, wherein said eukaryotic cell is selected from the group consisting of a human embryonic kidney-293 cell and a rat GH4C1 pituitary cell.

17. An isolated polypeptide of a modified mammalian olfactory cyclic nucleotide-gated ion channel alpha subunit, wherein said channel comprises a mutation, wherein said mutation comprises a substitution at a residue corresponding to position 583 of SEQ ID NO:8, and wherein said channel has increased cAMP sensitivity, and decreased cGMP sensitivity as compared to a wild type channel.

* * * * *

SEQUENCE LISTING

```
<160> NUMBER OF SEQ ID NOS: 8

<210> SEQ ID NO 1
<211> LENGTH: 3027
<212> TYPE: DNA
<213> ORGANISM: Rattus norvegicus

<400> SEQUENCE: 1

aattccaaca ttgaagatgg cttctccagg ggccggggca ccctgatagg ctctcaagct     60

cacctagctg tgttatgtgc tccattgggc ctctgtcagc tgctatcaga cagcgtgggc    120

tagatctctg attgggaagc tgctgctgtt tgttggggtc tcagagaacc ttccctggct    180

ggacaacaga agaaacagga aatctcttca gctttcagtg ctcatgagct cccaagagct    240

tctctttgat tggagctggt gtggacagaa caacagatgt tgactgtgac ctcaggactc    300

tgaaaccatc tgactggtga gagccctgga tttacatgga tgatgaccga aaaatccaat    360
```

-continued

```
ggtgtgaaaa gctctccagc taataaccat aaccatcatc ctcctccttc tatcaaggcc    420

aatggcaaag atgaccacag ggcaggaagc agaccacagt ctgtggcagc tgatgatgac    480

acttctccag aactacaaag gctggcagag atggataccc ctcggagggg gaggggtggc    540

ttccaaagga ttgttcgcct ggtgggggtc atcagggact gggccaacaa gaatttccgt    600

gaagaggaac caaggcctga ctccttccta gagcgtttcc gtgggccaga actccagact    660

gtgacaaccc atcaggggga tgacaaaggc ggcaaggacg gcgagggaaa gggcaccaaa    720

aagaaatttg aactgtttgt tttggaccca gccggagact ggtattaccg ttggttgttt    780

gtcattgcca tgcctgttct ttacaactgg tgcctgttgg tggccagagc ctgcttcagt    840

gatctacaga gaaactattt tgtggtatgg ctggtgctgg actacttctc agacactgtc    900

tatatcgcag acctcatcat tcggctgcgc acaggcttcc tagaacaggg gctcttggtc    960

aaagatccca agaaattgcg agacaactat attcacactt tgcagttcaa attggatgtg   1020

gcttctatca ttcccactga ccttatctat tttgctgtgg gtatccacag ccctgaggta   1080

cgcttcaacc gtctattaca ctttgcccgt atgtttgagt tctttgaccg cactgagaca   1140

cgcaccagct accccaacat cttccgaatc agcaatctgg tcctttacat cttggtcatc   1200

atccactgga atgcttgtat ttattatgtt atttctaagt ccattggctt tggagttgac   1260

acctgggttt accccaacat tactgaccct gaatatggct acctggctag agagtacatt   1320

tactgtcttt actggtccac actgaccctc accaccattg gagagacacc accccctgta   1380

aaggatgagg agtacctatt tgtcatcttt gacttcttga ttggtgtcct catctttgcc   1440

actattgtgg gaaatgtggg ctccatgatc tccaacatga atgccacacg agcagagttc   1500

caggccaaga ttgatgctgt caaacactac atgcagttcc gaaaggtcag caaagacatg   1560

gaagccaagg tcatcaaatg gtttgactac ttgtggacca ataagaagac agtagatgaa   1620

cgagaagtcc tcaagaacct gccagcaaag ctcagggctg agatagccat taatgttcac   1680

ttgtccactc tgaagaaagt gcgcatattc caggattgtg aagctggcct actggtggaa   1740

ctggtactga agcttcgtcc tcaggtcttt agtcctggag attatatttg ccgtaagggg   1800

gacattggca aggaaatgta catcatcaag gagggcaagt tggcagtggt agctgatgat   1860

ggcgtgactc agtatgcctt gctctcagct gggagctgct ttggtgagat tagtatcctt   1920

aacattaagg gtagcaaaat gggcaatcga cgtactgcta atatccgtag cctgggctac   1980

tcagatctct tctgcttgtc caaggacgat cttatggaag ctgtaactga gtatcctgat   2040

gccaagaagg tcctggagga acggggtagg gagatcctga tgaagatggg tctactggat   2100

gagaatgaag tggcagctag tatggaggta gatgttcagg agaagctgga acagttggag   2160

acaaacatgg ataccttgta cactcgcttt gcccgcctgc tggctgagta cactggggcc   2220

cagcagaagc tcaagcaacg catcacagtg ctagagacca agatgaaaca gaaccatgag   2280

gatgattatc tatcagatgg gataaacact cctgagccaa ctgctgctga ataaccataa   2340

gtgactatcc agccttggtc tgactccagg agttagaagt gctgtataga actttacatt   2400

tacacacatt atgctcatgt ccctctgaac tctccccaaa gccatgctga ggcttaaggt   2460

tttgactaca tcttgaagtc cccctctaag tccagctaac agtcaagctt gtggacaatg   2520

cagatcatgt gggttgaatt tccaagagct tgacctccta tgtctgaaaa gggatcagag   2580

actagctaaa ttgtccttcc tggggctttt ctggtactag atacctagac agtgttctct   2640

gaagaacact gtgcacaatg cctgactccc tttagtttct ttatatctag tcactcccta   2700

ctgtattctg ccccaaatac ctttttttaat gtgttctcta agcagcctgt ttccatgtac   2760
```

```
atgtataaat ttaagaattg gctgcaaaca ctgggccccc taaactgtct cccaaggcat   2820
gcaagggccg tgaggggagt ggtagggtgg gtttgagtgt gtgtgctcag ggtcatactt   2880
ccttgtcaga caatgtcact atgagaagag gtggctggca gctttggcca tcacaccttt   2940
atgcacacaa gttctgaaga gtttgtgaat gctgagatac tgtgaattag agccacttaa   3000
aagttaataa attcttttca gctaaaa                                       3027
```

```
<210> SEQ ID NO 2
<211> LENGTH: 3027
<212> TYPE: DNA
<213> ORGANISM: Rattus norvegicus

<400> SEQUENCE: 2

aattccaaca ttgaagatgg cttctccagg ggccggggca ccctgatagg ctctcaagct     60
cacctagctg tgttatgtgc tccattgggc ctctgtcagc tgctatcaga cagcgtgggc    120
tagatctctg attgggaagc tgctgctgtt tgttggggtc tcagagaacc ttccctggct    180
ggacaacaga agaaacagga aatctcttca gctttcagtg ctcatgagct cccaagagct    240
tctctttgat tggagctggt gtggacagaa caacagatgt tgactgtgac ctcaggactc    300
tgaaaccatc tgactggtga gagccctgga tttacatgga tgatgaccga aaaatccaat    360
ggtgtgaaaa gctctccagc taataaccat aaccatcatc ctcctccttc tatcaaggcc    420
aatggcaaag atgaccacag ggcaggaagc agaccacagt ctgtggcagc tgatgatgac    480
acttctccag aactacaaag gctggcagag atggataccc ctcggagggg gaggggtggc    540
ttccaaagga ttgttcgcct ggtgggggtc atcagggact gggccaacaa gaatttccgt    600
gaagaggaac caaggcctga ctccttccta gagcgtttcc gtgggccaga actccagact    660
gtgacaaccc atcaggggga tgacaaaggc ggcaaggacg gcgagggaaa gggcaccaaa    720
aagaaatttg aactgtttgt tttggaccca gccggagact ggtattaccg ttggttgttt    780
gtcattgcca tgcctgttct ttacaactgg tgcctgttgg tggccagagc ctgcttcagt    840
gatctacaga gaaactattt tgtggtatgg ctggtgctgg actacttctc agacactgtc    900
tatatcgcag acctcatcat tcggctgcgc acaggcttcc tagaacaggg gctcttggtc    960
aaagatccca agaaattgcg agacaactat attcacactt tgcagttcaa attggatgtg   1020
gcttctatca ttcccactga ccttatctat tttgctgtgg gtatccacag ccctgaggta   1080
cgcttcaacc gtctattaca ctttgcccgt atgtttgagt tctttgaccg cactgagaca   1140
cgcaccagct accccaacat cttccgaatc agcaatctgg tcctttacat cttggtcatc   1200
atccactgga atgcttgtat ttattatgtt atttctaagt ccattggctt tggagttgac   1260
acctgggttt accccaacat tactgaccct gaatatggct acctggctag agagtacatt   1320
tactgtcttt actggtccac actgaccctc accaccattg gagagacacc acccccctgta   1380
aaggatgagg agtacctatt tgtcatcttt gacttcttga ttggtgtcct catctttgcc   1440
actattgtgg gaaatgtggg ctccatgatc tccaacatga atgccacacg agcagagttc   1500
caggccaaga ttgatgctgt caaacactac atgcagttcc gaaaggtcag caaagacatg   1560
gaagccaagg tcatcaaatg gtttgactac ttgtggacca ataagaagac agtagatgaa   1620
cgagaagtcc tcaagaacct gccagcaaag ctcagggctg agatagccat taatgttcac   1680
ttgtccactc tgaagaaagt gcgcatattc caggattggg aagctggcct actggtggaa   1740
ctggtactga agcttcgtcc tcaggtcttt agtcctggag attatatttg ccgtaagggg   1800
```

-continued

```
gacattggca aggaaatgta catcatcaag gagggcaagt tggcagtggt agctgatgat   1860
ggcgtgactc agtatgcctt gctctcagct gggagctgct ttggtgagat tagtatcctt   1920
aacattaagg gtagcaaaat gggcaatcga cgtactgcta atatccgtag cctgggctac   1980
tcagatctct tctgcttgtc caaggacgat cttatggaag ctgtaactga gtatcctgat   2040
gccaagaagg tcctggagga acggggtagg gagatcctga tgaagatggg tctactggat   2100
gagaatgaag tggcagctag tatggaggta gatgttcagg agaagctgga acagttggag   2160
acaaacatgg ataccttgta cactcgcttt gcccgcctgc tggctgagta cactggggcc   2220
cagcagaagc tcaagcaacg catcacagtg ctagagacca agatgaaaca gaaccatgag   2280
gatgattatc tatcagatgg gataaacact cctgagccaa ctgctgctga ataaccataa   2340
gtgactatcc agccttggtc tgactccagg agttagaagt gctgtataga actttacatt   2400
tacacacatt atgctcatgt ccctctgaac tctccccaaa gccatgctga ggcttaaggt   2460
tttgactaca tcttgaagtc cccctctaag tccagctaac agtcaagctt gtggacaatg   2520
cagatcatgt gggttgaatt tccaagagct tgacctccta tgtctgaaaa gggatcagag   2580
actagctaaa ttgtccttcc tggggctttt ctggtactag atacctagac agtgttctct   2640
gaagaacact gtgcacaatg cctgactccc tttagtttct ttatatctag tcactcccta   2700
ctgtattctg ccccaaatac ctttttttaat gtgttctcta agcagcctgt ttccatgtac   2760
atgtataaat ttaagaattg gctgcaaaca ctgggccccc taaactgtct cccaaggcat   2820
gcaagggccg tgaggggagt ggtagggtgg gtttgagtgt gtgtgctcag ggtcatactt   2880
ccttgtcaga caatgtcact atgagaagag gtggctggca gctttggcca tcacaccttt   2940
atgcacacaa gttctgaaga gtttgtgaat gctgagatac tgtgaattag agccacttaa   3000
aagttaataa attcttttca gctaaaa                                       3027
```

```
<210> SEQ ID NO 3
<211> LENGTH: 2877
<212> TYPE: DNA
<213> ORGANISM: Rattus norvegicus

<400> SEQUENCE: 3
```

```
aattccaaca ttgaagatgg cttctccagg ggccggggca ccctgatagg ctctcaagct     60
cacctagctg tgttatgtgc tccattgggc ctctgtcagc tgctatcaga cagcgtgggc    120
tagatctctg attgggaagc tgctgctgtt tgttggggtc tcagagaacc ttccctggct    180
ggacaacaga agaaacagga aatctcttca gctttcagtg ctcatgagct cccaagagct    240
tctctttgat tggagctggt gtggacagaa caacagatgt tgactgtgac ctcaggactc    300
tgaaaccatc tgactggtga gagccctgga tttacatgga tgatgaccga aaaatccaat    360
ggtgtgaaaa gctctccagc taataaccat aaccatcatc ctcctccttc tatcaaggcc    420
aatggcaaag atgaccacag ggcaggaagc agaccacagt ctgtggcagc tgatgatgac    480
acttctccag aactacaaag gctggcagag atggataccc ctaggcctga ctccttccta    540
gagcgtttcc gtgggccaga actccagact gtgacaaccc atcaggggga tgacaaaggc    600
ggcaaggacg gcgagggaaa gggcaccaaa gtcattgcca tgcctgttct ttacaactgg    660
tgcctgttgg tggccagagc ctgcttcagt gatctacaga gaaactattt tgtggtatgg    720
ctggtgctgg actacttctc agacactgtc tatatcgcag acctcatcat tcggctgcgc    780
acaggcttcc tagaacaggg gctcttggtc aaagatccca agaaattgcg agacaactat    840
attcacactt tgcagttcaa attggatgtg gcttctatca ttcccactga ccttatctat    900
```

-continued

```
tttgctgtgg gtatccacag ccctgaggta cgcttcaacc gtctattaca ctttgcccgt    960
atgtttgagt tctttgaccg cactgagaca cgcaccagct accccaacat cttccgaatc   1020
agcaatctgg tcctttacat cttggtcatc atccactgga atgcttgtat ttattatgtt   1080
atttctaagt ccattggctt tggagttgac acctgggttt accccaacat tactgaccct   1140
gaatatggct acctggctag agagtacatt tactgtcttt actggtccac actgaccctc   1200
accaccattg gagagacacc accccctgta aaggatgagg agtacctatt tgtcatcttt   1260
gacttcttga ttggtgtcct catctttgcc actattgtgg gaaatgtggg ctccatgatc   1320
tccaacatga atgccacacg agcagagttc caggccaaga ttgatgctgt caaacactac   1380
atgcagttcc gaaaggtcag caaagacatg gaagccaagg tcatcaaatg gtttgactac   1440
ttgtggacca ataagaagac agtagatgaa cgagaagtcc tcaagaacct gccagcaaag   1500
ctcagggctg agatagccat taatgttcac ttgtccactc tgaagaaagt gcgcatattc   1560
caggattggg aagctggcct actggtggaa ctggtactga agcttcgtcc tcaggtcttt   1620
agtcctggag attatatttg ccgtaagggg gacattggca aggaaatgta catcatcaag   1680
gagggcaagt tggcagtggt agctgatgat ggcgtgactc agtatgcctt gctctcagct   1740
gggagctgct ttggtgagat tagtatcctt aacattaagg gtagcaaaat gggcaatcga   1800
cgtactgcta atatccgtag cctgggctac tcagatctct tctgcttgtc caaggacgat   1860
cttatggaag ctgtaactga gtatcctgat gccaagaagg tcctggagga acggggtagg   1920
gagatcctga tgaagatggg tctactggat gagaatgaag tggcagctag tatggaggta   1980
gatgttcagg agaagctgga acagttggag acaaacatgg ataccttgta cactcgcttt   2040
gcccgcctgc tggctgagta cactggggcc cagcagaagc tcaagcaacg catcacagtg   2100
ctagagacca agatgaaaca gaaccatgag gatgattatc tatcagatgg gataaacact   2160
cctgagccaa ctgctgctga ataaccataa gtgactatcc agccttggtc tgactccagg   2220
agttagaagt gctgtataga actttacatt tacacacatt atgctcatgt ccctctgaac   2280
tctccccaaa gccatgctga ggcttaaggt tttgactaca tcttgaagtc cccctctaag   2340
tccagctaac agtcaagctt gtggacaatg cagatcatgt gggttgaatt tccaagagct   2400
tgacctccta tgtctgaaaa gggatcagag actagctaaa ttgtccttcc tggggctttt   2460
ctggtactag atacctagac agtgttctct gaagaacact gtgcacaatg cctgactccc   2520
tttagtttct ttatatctag tcactcccta ctgtattctg ccccaaatac ctttttttaat   2580
gtgttctcta agcagcctgt ttccatgtac atgtataaat ttaagaattg gctgcaaaca   2640
ctgggccccc taaactgtct cccaaggcat gcaagggccg tgaggggagt ggtagggtgg   2700
gtttgagtgt gtgtgctcag ggtcatactt ccttgtcaga caatgtcact atgagaagag   2760
gtggctggca gctttggcca tcacaccttt atgcacacaa gttctgaaga gtttgtgaat   2820
gctgagatac tgtgaattag agccacttaa aagttaataa attcttttca gctaaaa      2877
```

<210> SEQ ID NO 4
<211> LENGTH: 3027
<212> TYPE: DNA
<213> ORGANISM: Rattus norvegicus

<400> SEQUENCE: 4

```
aattccaaca ttgaagatgg cttctccagg ggccggggca ccctgatagg ctctcaagct     60
cacctagctg tgttatgtgc tccattgggc ctctgtcagc tgctatcaga cagcgtgggc    120
```

-continued

```
tagatctctg attgggaagc tgctgctgtt tgttggggtc tcagagaacc ttccctggct    180
ggacaacaga agaaacagga aatctcttca gctttcagtg ctcatgagct cccaagagct    240
tctctttgat tggagctggt gtggacagaa caacagatgt tgactgtgac ctcaggactc    300
tgaaaccatc tgactggtga gagccctgga tttacatgga tgatgaccga aaaatccaat    360
ggtgtgaaaa gctctccagc taataaccat aaccatcatc ctcctccttc tatcaaggcc    420
aatggcaaag atgaccacag ggcaggaagc agaccacagt ctgtggcagc tgatgatgac    480
acttctccag aactacaaag gctggcagag atggataccc ctcggagggg gaggggtggc    540
ttccaaagga ttgttcgcct ggtgggggtc atcagggact gggccaacaa gaatttccgt    600
gaagaggaac caaggcctga ctccttccta gagcgtttcc gtgggccaga actccagact    660
gtgacaaccc atcaggggga tgacaaaggc ggcaaggacg gcgagggaaa gggcaccaaa    720
aagaaatttg aactgtttgt tttggaccca gccggagact ggtattaccg ttggttgttt    780
gtcattgcca tgcctgttct ttacaactgg tgcctgttgg tggccagagc ctgcttcagt    840
gatctacaga gaaactattt tgtggtatgg ctggtgctgg actacttctc agacactgtc    900
tatatcgcag acctcatcat tcggctgcgc acaggcttcc tagaacaggg gctcttggtc    960
aaagatccca agaaattgcg agacaactat attcacactt tgcagttcaa attggatgtg   1020
gcttctatca ttcccactga ccttatctat tttgctgtgg gtatccacag ccctgaggta   1080
cgcttcaacc gtctattaca ctttgcccgt atgtttgagt tctttgaccg cactgagaca   1140
cgcaccagct accccaacat cttccgaatc agcaatctgg tcctttacat cttggtcatc   1200
atccactgga atgcttgtat ttattatgtt atttctaagt ccattggctt tggagttgac   1260
acctgggttt accccaacat tactgaccct gaatatggct acctggctag agagtacatt   1320
tactgtcttt actggtccac actgaccctc accaccattg gagagacacc accccctgta   1380
aaggatgagg agtacctatt tgtcatcttt gacttcttga ttggtgtcct catctttgcc   1440
actattgtgg gaaatgtggg ctccatgatc tccaacatga atgccacacg agcagagttc   1500
caggccaaga ttgatgctgt caaacactac atgcagttcc gaaaggtcag caaagacatg   1560
gaagccaagg tcatcaaatg gtttgactac ttgtggacca ataagaagac agtagatgaa   1620
cgagaagtcc tcaagaacct gccagcaaag ctcagggctg agatagccat taatgttcac   1680
ttgtccactc tgaagaaagt gcgcatattc caggattgtg aagctggcct actggtggaa   1740
ctggtactga agcttcgtcc tcaggtcttt agtcctggag attatatttg ccgtaagggg   1800
gacattggca aggaaatgta catcatcaag gagggcaagt tggcagtggt agctgatgat   1860
ggcgtgactc agtatgcctt gctctcagct gggagctgct ttggtgagat tagtatcctt   1920
aacattaagg gtagcaaaat gggcaatcga cgtactgcta atatccgtag cctgggctac   1980
tcagatctct tctgcttgtc caaggacgat cttatggaag ctgtaactga gtatcctgat   2040
gccaagaagg tcctggagga acggggtagg gagatcctga tgaaggaagg tctactggat   2100
gagaatgaag tggcagctag tatggaggta gatgttcagg agaagctgga acagttggag   2160
acaaacatgg ataccttgta cactcgcttt gcccgcctgc tggctgagta cactggggcc   2220
cagcagaagc tcaagcaacg catcacagtg ctagagacca agatgaaaca gaaccatgag   2280
gatgattatc tatcagatgg gataaacact cctgagccaa ctgctgctga ataaccataa   2340
gtgactatcc agccttggtc tgactccagg agttagaagt gctgtataga actttacatt   2400
tacacacatt atgctcatgt ccctctgaac tctccccaaa gccatgctga ggcttaaggt   2460
tttgactaca tcttgaagtc cccctctaag tccagctaac agtcaagctt gtggacaatg   2520
```

-continued

```
cagatcatgt gggttgaatt tccaagagct tgacctccta tgtctgaaaa gggatcagag   2580

actagctaaa ttgtccttcc tggggctttt ctggtactag atacctagac agtgttctct   2640

gaagaacact gtgcacaatg cctgactccc tttagtttct ttatatctag tcactcccta   2700

ctgtattctg ccccaaatac ctttttttaat gtgttctcta agcagcctgt ttccatgtac   2760

atgtataaat ttaagaattg gctgcaaaca ctgggccccc taaactgtct cccaaggcat   2820

gcaagggccg tgaggggagt ggtagggtgg gtttgagtgt gtgtgctcag ggtcatactt   2880

ccttgtcaga caatgtcact atgagaagag gtggctggca gctttggcca tcacaccttt   2940

atgcacacaa gttctgaaga gtttgtgaat gctgagatac tgtgaattag agccacttaa   3000

aagttaataa attcttttca gctaaaa                                        3027
```

```
<210> SEQ ID NO 5
<211> LENGTH: 664
<212> TYPE: PRT
<213> ORGANISM: Rattus norvegicus

<400> SEQUENCE: 5

Met Met Thr Glu Lys Ser Asn Gly Val Lys Ser Ser Pro Ala Asn Asn
1               5                   10                  15

His Asn His His Pro Pro Pro Ser Ile Lys Ala Asn Gly Lys Asp Asp
            20                  25                  30

His Arg Ala Gly Ser Arg Pro Gln Ser Val Ala Ala Asp Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys
        115                 120                 125

Lys Phe Glu Leu Phe Val Leu Asp Pro Ala Gly Asp Trp Tyr Tyr Arg
    130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
        195                 200                 205

Asp Pro Lys Lys Leu Arg Asp Asn Tyr Ile His Thr Leu Gln Phe Lys
    210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
            260                 265                 270

Asn Ile Phe Arg Ile Ser Asn Leu Val Leu Tyr Ile Leu Val Ile Ile
```

-continued

```
        275                 280                 285

His Trp Asn Ala Cys Ile Tyr Tyr Val Ile Ser Lys Ser Ile Gly Phe
    290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
        355                 360                 365

Ile Val Gly Asn Val Gly Ser Met Ile Ser Asn Met Asn Ala Thr Arg
    370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
        435                 440                 445

Ser Thr Leu Lys Lys Val Arg Ile Phe Gln Asp Cys Glu Ala Gly Leu
    450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Ala Asn Ile Arg Ser
    530                 535                 540

Leu Gly Tyr Ser Asp Leu Phe Cys Leu Ser Lys Asp Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Met Gly Leu Leu Asp Glu Asn Glu Val Ala
            580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
            660
```

<210> SEQ ID NO 6
<211> LENGTH: 664
<212> TYPE: PRT
<213> ORGANISM: Rattus norvegicus

<400> SEQUENCE: 6

```
Met Met Thr Glu Lys Ser Asn Gly Val Lys Ser Ser Pro Ala Asn Asn
1               5                   10                  15

His Asn His His Pro Pro Pro Ser Ile Lys Ala Asn Gly Lys Asp Asp
            20                  25                  30

His Arg Ala Gly Ser Arg Pro Gln Ser Val Ala Ala Asp Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys
        115                 120                 125

Lys Phe Glu Leu Phe Val Leu Asp Pro Ala Gly Asp Trp Tyr Tyr Arg
    130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
        195                 200                 205

Asp Pro Lys Lys Leu Arg Asp Asn Tyr Ile His Thr Leu Gln Phe Lys
    210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
            260                 265                 270

Asn Ile Phe Arg Ile Ser Asn Leu Val Leu Tyr Ile Leu Val Ile Ile
        275                 280                 285

His Trp Asn Ala Cys Ile Tyr Tyr Val Ile Ser Lys Ser Ile Gly Phe
    290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
        355                 360                 365

Ile Val Gly Asn Val Gly Ser Met Ile Ser Asn Met Asn Ala Thr Arg
    370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
```

```
            405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
        435                 440                 445

Ser Thr Leu Lys Lys Val Arg Ile Phe Gln Asp Trp Glu Ala Gly Leu
    450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Ala Asn Ile Arg Ser
    530                 535                 540

Leu Gly Tyr Ser Asp Leu Phe Cys Leu Ser Lys Asp Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Met Gly Leu Leu Asp Glu Asn Glu Val Ala
            580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
            660


<210> SEQ ID NO 7
<211> LENGTH: 634
<212> TYPE: PRT
<213> ORGANISM: Rattus norvegicus

<400> SEQUENCE: 7

Met Met Thr Glu Lys Ser Asn Gly Val Lys Ser Ser Pro Ala Asn Asn
1               5                   10                  15

His Asn His His Pro Pro Pro Ser Ile Lys Ala Asn Gly Lys Asp Asp
            20                  25                  30

His Arg Ala Gly Ser Arg Pro Gln Ser Val Ala Ala Asp Asp Asp Thr
        35                  40                  45

Ser Pro Glu Leu Gln Arg Leu Ala Glu Met Asp Thr Pro Arg Pro Asp
    50                  55                  60

Ser Phe Leu Glu Arg Phe Arg Gly Pro Glu Leu Gln Thr Val Thr Thr
65                  70                  75                  80

His Gln Gly Asp Asp Lys Gly Gly Lys Asp Gly Glu Gly Lys Gly Thr
                85                  90                  95

Lys Lys Lys Phe Glu Leu Phe Val Leu Asp Pro Ala Gly Asp Trp Tyr
            100                 105                 110
```

-continued

```
Tyr Arg Trp Leu Phe Val Ile Ala Met Pro Val Leu Tyr Asn Trp Cys
        115                 120                 125

Leu Leu Val Ala Arg Ala Cys Phe Ser Asp Leu Gln Arg Asn Tyr Phe
    130                 135                 140

Val Val Trp Leu Val Leu Asp Tyr Phe Ser Asp Thr Val Tyr Ile Ala
145                 150                 155                 160

Asp Leu Ile Ile Arg Leu Arg Thr Gly Phe Leu Glu Gln Gly Leu Leu
                165                 170                 175

Val Lys Asp Pro Lys Lys Leu Arg Asp Asn Tyr Ile His Thr Leu Gln
            180                 185                 190

Phe Lys Leu Asp Val Ala Ser Ile Ile Pro Thr Asp Leu Ile Tyr Phe
        195                 200                 205

Ala Val Gly Ile His Ser Pro Glu Val Arg Phe Asn Arg Leu Leu His
    210                 215                 220

Phe Ala Arg Met Phe Glu Phe Phe Asp Arg Thr Glu Thr Arg Thr Ser
225                 230                 235                 240

Tyr Pro Asn Ile Phe Arg Ile Ser Asn Leu Val Leu Tyr Ile Leu Val
                245                 250                 255

Ile Ile His Trp Asn Ala Cys Ile Tyr Tyr Val Ile Ser Lys Ser Ile
            260                 265                 270

Gly Phe Gly Val Asp Thr Trp Val Tyr Pro Asn Ile Thr Asp Pro Glu
        275                 280                 285

Tyr Gly Tyr Leu Ala Arg Glu Tyr Ile Tyr Cys Leu Tyr Trp Ser Thr
    290                 295                 300

Leu Thr Leu Thr Thr Ile Gly Glu Thr Pro Pro Pro Val Lys Asp Glu
305                 310                 315                 320

Glu Tyr Leu Phe Val Ile Phe Asp Phe Leu Ile Gly Val Leu Ile Phe
                325                 330                 335

Ala Thr Ile Val Gly Asn Val Gly Ser Met Ile Ser Asn Met Asn Ala
            340                 345                 350

Thr Arg Ala Glu Phe Gln Ala Lys Ile Asp Ala Val Lys His Tyr Met
        355                 360                 365

Gln Phe Arg Lys Val Ser Lys Asp Met Glu Ala Lys Val Ile Lys Trp
    370                 375                 380

Phe Asp Tyr Leu Trp Thr Asn Lys Lys Thr Val Asp Glu Arg Glu Val
385                 390                 395                 400

Leu Lys Asn Leu Pro Ala Lys Leu Arg Ala Glu Ile Ala Ile Asn Val
                405                 410                 415

His Leu Ser Thr Leu Lys Lys Val Arg Ile Phe Gln Asp Trp Glu Ala
            420                 425                 430

Gly Leu Leu Val Glu Leu Val Leu Lys Leu Arg Pro Gln Val Phe Ser
        435                 440                 445

Pro Gly Asp Tyr Ile Cys Arg Lys Gly Asp Ile Gly Lys Glu Met Tyr
    450                 455                 460

Ile Ile Lys Glu Gly Lys Leu Ala Val Val Ala Asp Asp Gly Val Thr
465                 470                 475                 480

Gln Tyr Ala Leu Leu Ser Ala Gly Ser Cys Phe Gly Glu Ile Ser Ile
                485                 490                 495

Leu Asn Ile Lys Gly Ser Lys Met Gly Asn Arg Arg Thr Ala Asn Ile
            500                 505                 510

Arg Ser Leu Gly Tyr Ser Asp Leu Phe Cys Leu Ser Lys Asp Asp Leu
        515                 520                 525

Met Glu Ala Val Thr Glu Tyr Pro Asp Ala Lys Lys Val Leu Glu Glu
```

-continued

```
    530                 535                 540

Arg Gly Arg Glu Ile Leu Met Lys Met Gly Leu Leu Asp Glu Asn Glu
545                 550                 555                 560

Val Ala Ala Ser Met Glu Val Asp Val Gln Glu Lys Leu Glu Gln Leu
                565                 570                 575

Glu Thr Asn Met Asp Thr Leu Tyr Thr Arg Phe Ala Arg Leu Leu Ala
            580                 585                 590

Glu Tyr Thr Gly Ala Gln Gln Lys Leu Lys Gln Arg Ile Thr Val Leu
        595                 600                 605

Glu Thr Lys Met Lys Gln Asn His Glu Asp Asp Tyr Leu Ser Asp Gly
    610                 615                 620

Ile Asn Thr Pro Glu Pro Thr Ala Ala Glu
625                 630


<210> SEQ ID NO 8
<211> LENGTH: 664
<212> TYPE: PRT
<213> ORGANISM: Rattus norvegicus

<400> SEQUENCE: 8

Met Met Thr Glu Lys Ser Asn Gly Val Lys Ser Ser Pro Ala Asn Asn
1               5                   10                  15

His Asn His His Pro Pro Pro Ser Ile Lys Ala Asn Gly Lys Asp Asp
            20                  25                  30

His Arg Ala Gly Ser Arg Pro Gln Ser Val Ala Ala Asp Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys
        115                 120                 125

Lys Phe Glu Leu Phe Val Leu Asp Pro Ala Gly Asp Trp Tyr Tyr Arg
    130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
        195                 200                 205

Asp Pro Lys Lys Leu Arg Asp Asn Tyr Ile His Thr Leu Gln Phe Lys
    210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
            260                 265                 270
```

-continued

```
Asn Ile Phe Arg Ile Ser Asn Leu Val Leu Tyr Ile Leu Val Ile Ile
        275                 280                 285

His Trp Asn Ala Cys Ile Tyr Tyr Val Ile Ser Lys Ser Ile Gly Phe
    290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
        355                 360                 365

Ile Val Gly Asn Val Gly Ser Met Ile Ser Asn Met Asn Ala Thr Arg
    370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
        435                 440                 445

Ser Thr Leu Lys Lys Val Arg Ile Phe Gln Asp Cys Glu Ala Gly Leu
    450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Ala Asn Ile Arg Ser
    530                 535                 540

Leu Gly Tyr Ser Asp Leu Phe Cys Leu Ser Lys Asp Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Glu Gly Leu Leu Asp Glu Asn Glu Val Ala
            580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
            660
```